United States Patent
Orr (12)

(10) Patent No.: US 10,578,098 B2
(45) Date of Patent: Mar. 3, 2020

(54) MEDICAL FLUID DELIVERY DEVICE ACTUATED VIA MOTIVE FLUID

(71) Applicant: Baxter International Inc., Deerfield, IL (US)

(72) Inventor: Troy J. Orr, Draper, UT (US)

(73) Assignees: Baxter International Inc., Deerfield, IL (US); Baxter Healthcare SA, Glattpark (Opfikon)

( * ) Notice: Subject to any disclaimer, the term of this patent is extended or adjusted under 35 U.S.C. 154(b) by 0 days.

(21) Appl. No.: 16/355,101

(22) Filed: Mar. 15, 2019

(65) Prior Publication Data

US 2019/0209768 A1   Jul. 11, 2019

Related U.S. Application Data

(63) Continuation of application No. 14/558,021, filed on Dec. 2, 2014, which is a continuation of application
(Continued)

(51) Int. Cl.
*F04B 45/053* (2006.01)
*F04B 43/073* (2006.01)
(Continued)

(52) U.S. Cl.
CPC .......... *F04B 45/053* (2013.01); *F04B 43/025* (2013.01); *F04B 43/06* (2013.01);
(Continued)

(58) Field of Classification Search
CPC ...... F04B 43/06; F04B 43/073; F04B 45/053; F04B 45/0536; F04B 43/026;
(Continued)

(56) References Cited

U.S. PATENT DOCUMENTS 329,773 A   11/1885   Perry
862,867 A   8/1907   Eggleston
(Continued)

FOREIGN PATENT DOCUMENTS

CN   1099103   2/1995
CN   L099L03   2/1995
(Continued)

OTHER PUBLICATIONS

Laser et al. Topical Review of micropumps, Institute of Physics Publishing, J. Micromech. Microeng. 14 (2004), PII: SO960-1317(04)06813-5, R35-R64.
(Continued)

*Primary Examiner* — Bryan M Lettman
(74) *Attorney, Agent, or Firm* — K&L Gates LLP

(57) ABSTRACT

A medical fluid delivery device includes a process fluid body including first and second sides defining a first process fluid inlet valve seat and a first process fluid outlet valve seat and a second process fluid inlet valve seat and a second process fluid outlet valve seat; a first motive fluid plate defining a first aligned motive fluid inlet valve actuation area and a first aligned motive fluid outlet valve actuation area; and a second motive fluid plate defining a second aligned motive fluid inlet valve actuation area and a second aligned motive fluid outlet valve actuation area. The device further includes a first inlet valve diaphragm disposed between the first motive fluid inlet valve actuation area and the first process fluid inlet valve seat; and a first outlet valve diaphragm disposed between the first motive fluid outlet valve actuation area and the first process fluid outlet valve seat.

26 Claims, 25 Drawing Sheets

Related U.S. Application Data

No. 13/472,099, filed on May 15, 2012, now Pat. No. 8,932,032, which is a continuation of application No. 11/945,177, filed on Nov. 26, 2007, now Pat. No. 8,197,231, which is a continuation-in-part of application No. 11/484,061, filed on Jul. 11, 2006, now Pat. No. 7,717,682.

(60) Provisional application No. 60/699,262, filed on Jul. 13, 2005.

(51) Int. Cl.
    *F04B 43/02*     (2006.01)
    *F04B 45/04*     (2006.01)
    *F04B 43/06*     (2006.01)

(52) U.S. Cl.
    CPC ...... *F04B 43/0733* (2013.01); *F04B 43/0736* (2013.01); *F04B 45/043* (2013.01)

(58) Field of Classification Search
    CPC .. F04B 43/025; F04B 45/043; F04B 43/0733; F04B 43/0736
    See application file for complete search history.

(56) References Cited

U.S. PATENT DOCUMENTS

| | | | |
|---|---|---|---|
| 1,029,232 | A | 6/1912 | Schaefer et al. |
| 1,946,343 | A | 2/1934 | Wicha |
| 2,308,974 | A | 1/1943 | Harper |
| 2,311,229 | A | 2/1943 | Herbert |
| 2,356,738 | A | 8/1944 | Brugger |
| 2,383,193 | A | 8/1945 | Herbert |
| 2,529,028 | A | 11/1950 | Landon |
| 2,658,526 | A | 11/1953 | Porter |
| 2,711,134 | A | 6/1955 | Hughes |
| 2,726,019 | A | 12/1955 | Moran |
| 2,732,807 | A | 1/1956 | Parsegian |
| 2,740,259 | A | 4/1956 | Westlund |
| 2,755,745 | A | 7/1956 | Lewis |
| 2,821,930 | A | 2/1958 | Smith |
| 2,836,121 | A | 5/1958 | Browne |
| 2,843,050 | A | 7/1958 | Harper |
| 2,855,144 | A | 10/1958 | Andreasen |
| 2,861,596 | A | 11/1958 | Ipsen |
| 2,871,795 | A | 2/1959 | Smith |
| 2,886,281 | A | 5/1959 | Canalizo |
| 2,895,653 | A | 7/1959 | Giepen |
| 2,920,573 | A | 1/1960 | Schuarte |
| 2,980,032 | A | 4/1961 | Schneider |
| 3,013,575 | A | 12/1961 | Persson |
| 3,036,526 | A | 5/1962 | Hise |
| 3,039,399 | A | 6/1962 | Everett |
| 3,045,601 | A | 6/1962 | Rippingille |
| 3,083,943 | A | 4/1963 | Stewart et al. |
| 3,148,624 | A | 9/1964 | Baldwin |
| 3,151,783 | A | 10/1964 | Shaw et al. |
| 3,208,721 | A | 9/1965 | McHugh |
| 3,216,415 | A | 11/1965 | Littleton |
| 3,252,623 | A | 5/1966 | Corbin et al. |
| 3,256,825 | A | 6/1966 | Limpert et al. |
| 3,240,152 | A | 9/1966 | Bower |
| 3,285,182 | A | 11/1966 | Pinkerton |
| 3,286,577 | A | 11/1966 | Weidner, Jr. |
| 3,307,481 | A | 3/1967 | DeCoyeDeCastelet |
| 3,310,281 | A | 3/1967 | Boteler |
| 3,314,371 | A | 4/1967 | Hopkinson |
| 3,318,324 | A | 5/1967 | Ruth |
| 3,323,786 | A | 6/1967 | Boschi |
| 3,379,216 | A | 4/1968 | Mercier |
| 3,386,388 | A | 6/1968 | Rosenberg |
| 3,387,566 | A | 6/1968 | Temple |
| 3,397,216 | A | 8/1968 | Welch et al. |
| 3,461,808 | A | 8/1969 | Nelson et al. |
| 3,491,675 | A | 1/1970 | Gold |
| 3,508,848 | A | 4/1970 | Schmidlin |
| 3,514,227 | A | 5/1970 | Rupp |
| 3,533,387 | A | 10/1970 | Kaneko |
| 3,556,465 | A | 1/1971 | Little |
| 3,645,992 | A | 2/1972 | Elston |
| 3,652,187 | A | 3/1972 | Loeffler et al. |
| 3,654,953 | A | 4/1972 | Hagdorn |
| 3,655,603 | A | 4/1972 | Morton et al. |
| 3,656,873 | A | 4/1972 | Schiff |
| 3,661,060 | A | 5/1972 | Bowen |
| 3,666,379 | A | 5/1972 | Mitchell et al. |
| 3,668,978 | A | 6/1972 | Bowen |
| 3,685,789 | A | 8/1972 | Puster et al. |
| 3,689,025 | A | 9/1972 | Kiser |
| 3,693,611 | A | 9/1972 | Ploss |
| 3,697,197 | A | 10/1972 | Berglund et al. |
| 3,718,552 | A | 2/1973 | Mortell |
| 3,727,623 | A | 4/1973 | Robbins |
| 3,741,687 | A | 6/1973 | Nystoem |
| 3,743,245 | A | 7/1973 | Demler, Sr. |
| 3,776,107 | A | 12/1973 | Molus |
| 3,781,141 | A | 12/1973 | Schall |
| 3,785,378 | A | 1/1974 | Stewart |
| 3,800,794 | A | 4/1974 | Georgi |
| 3,807,406 | A | 4/1974 | Rafferty et al. |
| 3,807,906 | A | 4/1974 | Breit |
| 3,814,548 | A | 6/1974 | Rupp |
| 3,816,034 | A | 6/1974 | Rosenquest, Jr. |
| 3,838,946 | A | 10/1974 | Schall |
| 3,927,955 | A | 12/1975 | Spinosa et al. |
| 3,955,901 | A | 5/1976 | Hamilton |
| 3,966,358 | A | 6/1976 | Heimes et al. |
| 3,985,133 | A | 10/1976 | Jenkins et al. |
| 3,985,135 | A | 10/1976 | Carpenter et al. |
| 3,995,774 | A | 12/1976 | Cooprider et al. |
| 4,008,710 | A | 2/1977 | Chmiel |
| 4,021,149 | A | 5/1977 | Rutenberg et al. |
| 4,021,164 | A | 5/1977 | Tell |
| 4,026,669 | A | 5/1977 | Leonard et al. |
| 4,042,311 | A | 8/1977 | Yonezawa |
| 4,046,610 | A | 9/1977 | Lilja |
| 4,047,844 | A | 9/1977 | Robinson |
| 4,089,342 | A | 5/1978 | Stradella et al. |
| 4,093,406 | A | 6/1978 | Miller |
| 4,104,008 | A | 8/1978 | Hoffmann et al. |
| 4,121,236 | A | 10/1978 | Welp et al. |
| 4,121,584 | A | 10/1978 | Turner et al. |
| 4,123,204 | A | 10/1978 | Scholle |
| 4,135,496 | A | 1/1979 | Chazov et al. |
| 4,142,523 | A | 3/1979 | Stegeman |
| 4,142,524 | A | 3/1979 | Jassawalla et al. |
| 4,150,922 | A | 4/1979 | Cuenoud et al. |
| 4,151,184 | A | 4/1979 | Smith |
| 4,152,098 | A | 5/1979 | Moody et al. |
| 4,158,530 | A | 6/1979 | Bernstein |
| 4,162,876 | A | 7/1979 | Kolfertz |
| 4,178,940 | A | 12/1979 | Au |
| 4,181,245 | A | 1/1980 | Garrett et al. |
| 4,185,759 | A | 1/1980 | Zissimopoulos |
| 4,199,307 | A | 4/1980 | Jassawalla |
| 4,204,538 | A | 5/1980 | Cannon |
| 4,205,238 | A | 5/1980 | Shim et al. |
| 4,214,237 | A | 7/1980 | Zissimopoulos |
| 4,222,127 | A | 9/1980 | Donachy et al. |
| 4,222,813 | A | 9/1980 | Jodrey |
| 4,230,844 | A | 10/1980 | Chang et al. |
| 4,236,880 | A | 12/1980 | Archibald |
| 4,261,356 | A | 4/1981 | Turner et al. |
| 4,262,668 | A | 4/1981 | Schmidt |
| 4,262,824 | A | 4/1981 | Hrynewycz |
| 4,264,020 | A | 4/1981 | Loiseau |
| 4,265,506 | A | 5/1981 | Hollyday |
| 4,265,600 | A | 5/1981 | Mandroian |
| 4,265,601 | A | 5/1981 | Mandroian |
| 4,266,657 | A | 5/1981 | Frost et al. |
| 4,273,121 | A | 6/1981 | Jassawalla |
| 4,276,004 | A | 6/1981 | Hahn et al. |
| 4,277,226 | A | 7/1981 | Archibald |

(56) References Cited

U.S. PATENT DOCUMENTS

| | | |
|---|---|---|
| 4,303,376 A | 12/1981 | Siekmann |
| 4,304,260 A | 12/1981 | Turner et al. |
| 4,308,978 A | 1/1982 | Bayly et al. |
| 4,321,939 A | 3/1982 | Fenwick |
| 4,322,201 A | 3/1982 | Archibald |
| 4,332,254 A | 6/1982 | Lundquist |
| 4,333,452 A | 6/1982 | Au |
| 4,364,386 A | 12/1982 | Jenkins et al. |
| 4,370,983 A | 2/1983 | Lichtenstein |
| 4,381,180 A | 4/1983 | Sell |
| 4,382,753 A | 5/1983 | Archibald |
| 4,410,322 A | 10/1983 | Archibald |
| 4,411,603 A | 10/1983 | Kell |
| 4,411,651 A | 10/1983 | Schulman |
| 4,412,553 A | 11/1983 | Kopp et al. |
| 4,421,506 A | 12/1983 | Danby et al. |
| 4,430,048 A | 2/1984 | Fritsch |
| 4,431,019 A | 2/1984 | Kopp et al. |
| 4,436,620 A | 3/1984 | Bellotti et al. |
| 4,453,931 A | 6/1984 | Pastrone |
| 4,453,932 A | 6/1984 | Pastrone |
| 4,468,177 A | 8/1984 | Strimling |
| 4,479,760 A | 10/1984 | Bilstad et al. |
| 4,479,761 A | 10/1984 | Bilstad et al. |
| 4,479,762 A | 10/1984 | Bilstad et al. |
| 4,483,665 A | 11/1984 | Hauser |
| 4,490,621 A | 12/1984 | Watabe et al. |
| 4,493,709 A | 1/1985 | Smith |
| 4,496,294 A | 1/1985 | Frikker |
| 4,497,760 A | 2/1985 | Sorlien |
| 4,501,300 A | 2/1985 | Murphy |
| 4,511,616 A | 4/1985 | Pitts et al. |
| 4,514,295 A | 4/1985 | Mathieu et al. |
| 4,515,017 A | 5/1985 | McConaghy |
| 4,515,792 A | 5/1985 | Watthey |
| 4,519,792 A | 5/1985 | Dawe |
| 4,523,598 A | 6/1985 | Weiss et al. |
| 4,527,411 A | 7/1985 | Shinosaki et al. |
| 4,536,201 A | 8/1985 | Brorsson et al. |
| 4,538,638 A | 9/1985 | Stack |
| 4,542,735 A | 9/1985 | Smith et al. |
| 4,543,044 A | 9/1985 | Simmons |
| 4,550,066 A | 10/1985 | Alexander et al. |
| 4,550,134 A | 10/1985 | Isogai et al. |
| 4,552,552 A | 11/1985 | Polaschegg et al. |
| 4,553,910 A | 11/1985 | Gosschalk |
| 4,558,715 A | 12/1985 | Walton et al. |
| 4,559,044 A | 12/1985 | Robinson et al. |
| 4,569,378 A | 2/1986 | Bergandy |
| 4,573,883 A | 3/1986 | Noon et al. |
| 4,583,920 A | 4/1986 | Lindner |
| 4,586,738 A | 5/1986 | Butler et al. |
| 4,597,412 A | 7/1986 | Stark |
| 4,605,396 A | 8/1986 | Tseo et al. |
| 4,606,374 A | 8/1986 | Kolenc et al. |
| 4,611,578 A | 9/1986 | Heimes |
| 4,623,328 A | 11/1986 | Hartranft |
| 4,624,625 A | 11/1986 | Schrenker |
| 4,627,419 A | 12/1986 | Hills |
| 4,627,837 A | 12/1986 | Gonzalo |
| 4,628,499 A | 12/1986 | Hammett |
| 4,634,430 A | 1/1987 | Polaschegg |
| 4,636,149 A | 1/1987 | Brown |
| 4,639,245 A | 1/1987 | Pastrone et al. |
| 4,643,713 A | 2/1987 | Viitala |
| 4,644,897 A | 2/1987 | Fender |
| 4,646,781 A | 3/1987 | McIntyre et al. |
| 4,657,490 A | 4/1987 | Abbott |
| 4,662,598 A | 5/1987 | Weingarten |
| 4,662,906 A | 5/1987 | Matkovich et al. |
| 4,676,467 A | 6/1987 | Palsulich |
| 4,684,106 A | 8/1987 | Kolenc et al. |
| 4,690,621 A | 9/1987 | Swain |
| 4,703,913 A | 11/1987 | Hunkapiller |
| 4,705,259 A | 11/1987 | Dolhen et al. |
| 4,710,166 A | 12/1987 | Thompson et al. |
| 4,735,558 A | 4/1988 | Kleinholz et al. |
| 4,741,678 A | 5/1988 | Nehring |
| 4,746,436 A | 5/1988 | Kopp et al. |
| 4,755,111 A | 7/1988 | Cocchi et al. |
| 4,755,228 A | 7/1988 | Sakurai et al. |
| 4,758,238 A | 7/1988 | Sundblom et al. |
| 4,759,264 A | 7/1988 | Danby et al. |
| 4,763,051 A | 8/1988 | Ruppert |
| 4,768,547 A | 9/1988 | Danby et al. |
| 4,773,218 A | 9/1988 | Wakita et al. |
| 4,778,451 A | 10/1988 | Kamen |
| 4,781,715 A | 11/1988 | Wurzel |
| 4,787,825 A | 11/1988 | Mantell |
| 4,808,161 A | 2/1989 | Kamen |
| 4,817,503 A | 4/1989 | Yamada |
| 4,818,186 A | 4/1989 | Pastrone et al. |
| 4,818,190 A | 4/1989 | Pelmulder et al. |
| 4,821,761 A | 4/1989 | Aid et al. |
| 4,826,482 A | 5/1989 | Kamen |
| 4,830,586 A | 5/1989 | Herter et al. |
| 4,840,542 A | 6/1989 | Abbott |
| 4,842,584 A | 6/1989 | Pastrone |
| 4,846,636 A | 7/1989 | Danby et al. |
| 4,850,817 A | 7/1989 | Nason et al. |
| 4,850,980 A | 7/1989 | Lentz et al. |
| 4,854,832 A | 8/1989 | Gardner et al. |
| 4,856,335 A | 8/1989 | Tornberg |
| 4,856,340 A | 8/1989 | Garrison |
| 4,857,048 A | 8/1989 | Simons et al. |
| 4,858,883 A | 8/1989 | Webster |
| 4,869,282 A | 9/1989 | Sittler et al. |
| 4,872,813 A | 10/1989 | Gorton et al. |
| 4,874,297 A | 10/1989 | Collins et al. |
| 4,882,346 A | 11/1989 | Driscoll et al. |
| 4,888,011 A | 12/1989 | King et al. |
| 4,894,164 A | 1/1990 | Polaschegg |
| 4,896,215 A | 1/1990 | Morcom |
| 4,900,305 A | 2/1990 | Smith et al. |
| 4,902,282 A | 2/1990 | Bellotti et al. |
| 4,906,260 A | 3/1990 | Emheiser et al. |
| 4,917,348 A | 4/1990 | Phallen et al. |
| 4,927,411 A | 5/1990 | Pastrone et al. |
| 4,928,605 A | 5/1990 | Suwa et al. |
| 4,935,125 A | 6/1990 | Era et al. |
| 4,938,742 A | 7/1990 | Smits |
| 4,944,487 A | 7/1990 | Holtermann |
| 4,950,134 A | 8/1990 | Bailey et al. |
| 4,969,866 A | 11/1990 | Inagaki |
| 4,974,754 A | 12/1990 | Wirz |
| 4,974,774 A | 12/1990 | Nakagawa et al. |
| 4,976,162 A | 12/1990 | Kamen |
| 4,981,418 A | 1/1991 | Kingsford et al. |
| 4,995,864 A | 2/1991 | Bartholomew et al. |
| 4,997,464 A | 3/1991 | Kopf |
| 5,002,471 A | 3/1991 | Perlov |
| 5,006,050 A | 4/1991 | Cooke et al. |
| 5,011,368 A | 4/1991 | Frindel et al. |
| 5,024,644 A | 6/1991 | Bunch, III |
| 5,036,886 A | 8/1991 | Olsen et al. |
| 5,038,640 A | 8/1991 | Sullivan et al. |
| 5,044,901 A | 9/1991 | Fumero et al. |
| 5,061,236 A | 10/1991 | Sutherland et al. |
| 5,062,770 A | 11/1991 | Story et al. |
| 5,062,774 A | 11/1991 | Kramer et al. |
| 5,088,515 A * | 2/1992 | Kamen ............ A61M 39/22 137/15.17 |
| 5,092,377 A | 3/1992 | Krumberger |
| 5,092,414 A | 3/1992 | Blezard |
| 5,095,141 A | 3/1992 | Schammel et al. |
| 5,098,262 A | 3/1992 | Wecker et al. |
| 5,098,377 A | 3/1992 | Borsanyi et al. |
| 5,100,380 A | 3/1992 | Epstein et al. |
| 5,100,699 A | 3/1992 | Roeser |
| 5,108,367 A | 4/1992 | Epstein et al. |
| 5,116,021 A | 5/1992 | Faust et al. |
| 5,116,316 A | 5/1992 | Sertic et al. |
| 5,145,331 A | 9/1992 | Goes et al. |
| 5,146,713 A | 9/1992 | Grafius |

(56) References Cited

U.S. PATENT DOCUMENTS

| | | |
|---|---|---|
| 5,151,019 A | 9/1992 | Danby et al. |
| 5,158,210 A | 10/1992 | Du |
| 5,158,529 A | 10/1992 | Kanai |
| 5,167,387 A | 12/1992 | Hartwich |
| 5,167,837 A | 12/1992 | Snodgrass et al. |
| 5,171,029 A | 12/1992 | Maxwell et al. |
| 5,178,182 A | 1/1993 | Kamen |
| 5,193,977 A | 3/1993 | Dame |
| 5,193,990 A | 3/1993 | Kamen et al. |
| 5,201,636 A | 4/1993 | Mikulski |
| 5,205,722 A | 4/1993 | Hammond |
| 5,211,201 A | 5/1993 | Kamen et al. |
| 5,213,485 A | 5/1993 | Wilden |
| 5,232,434 A | 8/1993 | Inagaki et al. |
| 5,241,985 A | 9/1993 | Faust et al. |
| 5,242,384 A | 9/1993 | Robinson et al. |
| 5,247,434 A | 9/1993 | Peterson et al. |
| 5,249,932 A | 10/1993 | Van Bork |
| 5,252,041 A | 10/1993 | Schumack |
| 5,252,044 A | 10/1993 | Raines et al. |
| 5,259,352 A | 11/1993 | Gerhardy et al. |
| 5,261,798 A | 11/1993 | Budde |
| 5,262,068 A | 11/1993 | Browers et al. |
| 5,269,811 A | 12/1993 | Hayes et al. |
| 5,279,504 A | 1/1994 | Williams |
| 5,279,556 A | 1/1994 | Goi et al. |
| 5,292,384 A | 3/1994 | Klueh et al. |
| 5,302,093 A | 4/1994 | Owens et al. |
| 5,304,126 A | 4/1994 | Epstein et al. |
| 5,324,422 A | 6/1994 | Colleran et al. |
| 5,330,425 A | 7/1994 | Utterberg |
| 5,332,372 A | 7/1994 | Reynolds |
| 5,342,182 A | 8/1994 | Montoya et al. |
| 5,344,292 A * | 9/1994 | Rabenau .............. F04B 43/02 417/360 |
| 5,350,357 A | 9/1994 | Kamen et al. |
| D351,470 S | 10/1994 | Scherer et al. |
| 5,353,837 A | 10/1994 | Faust |
| 5,368,452 A | 11/1994 | Johnson et al. |
| 5,378,126 A | 1/1995 | Abrahamson et al. |
| 5,391,060 A | 2/1995 | Kozumplik et al. |
| 5,395,351 A | 3/1995 | Munsch |
| 5,401,963 A | 3/1995 | Sittler |
| 5,413,626 A | 5/1995 | Bartsch |
| 5,415,528 A | 5/1995 | Ogden et al. |
| 5,421,208 A | 6/1995 | Packard et al. |
| 5,421,823 A | 6/1995 | Kamen et al. |
| 5,423,738 A | 6/1995 | Robinson et al. |
| 5,427,509 A | 6/1995 | Chapman et al. |
| 5,429,485 A | 7/1995 | Dodge |
| 5,431,626 A | 7/1995 | Bryant et al. |
| 5,431,627 A | 7/1995 | Pastrone et al. |
| 5,431,634 A | 7/1995 | Brown |
| 5,437,542 A | 8/1995 | Ewing |
| 5,438,510 A | 8/1995 | Bryant et al. |
| 5,441,392 A | 8/1995 | Lundback |
| 5,441,636 A | 8/1995 | Chevallet et al. |
| 5,445,506 A | 8/1995 | Afflerbaugh et al. |
| 5,447,286 A | 9/1995 | Kamen et al. |
| 5,462,416 A | 10/1995 | Dennehey et al. |
| 5,462,417 A | 10/1995 | Chapman |
| 5,464,352 A | 11/1995 | Van Emmerick |
| 5,474,683 A | 12/1995 | Bryant et al. |
| 5,476,368 A | 12/1995 | Rabenau et al. |
| 5,476,378 A | 12/1995 | Zagoroff et al. |
| 5,478,211 A | 12/1995 | Dominiak et al. |
| 5,480,294 A | 1/1996 | DiPerna et al. |
| 5,482,438 A | 1/1996 | Anderson et al. |
| 5,482,440 A | 1/1996 | Dennehey et al. |
| 5,482,446 A | 1/1996 | Williamson et al. |
| 5,484,239 A | 1/1996 | Chapman et al. |
| 5,486,286 A | 1/1996 | Peterson et al. |
| 5,490,765 A | 2/1996 | Bailey et al. |
| 5,499,906 A | 3/1996 | O'Leary |
| 5,499,909 A | 3/1996 | Yamada et al. |
| 5,502,096 A | 3/1996 | Kimura et al. |
| 5,503,538 A | 4/1996 | Wiernicki et al. |
| 5,514,069 A | 5/1996 | Brown et al. |
| 5,520,523 A | 5/1996 | Yorita et al. |
| 5,522,998 A | 6/1996 | Polaschegg |
| 5,524,865 A | 6/1996 | Uchisawa et al. |
| 5,527,161 A | 6/1996 | Bailey et al. |
| 5,538,405 A | 7/1996 | Patno et al. |
| 5,540,568 A | 7/1996 | Rosen et al. |
| 5,547,453 A | 8/1996 | DiPerna |
| 5,551,850 A | 9/1996 | Williamson et al. |
| 5,551,941 A | 9/1996 | Howell |
| 5,551,942 A | 9/1996 | Brown et al. |
| 5,554,011 A | 9/1996 | Bales et al. |
| 5,554,013 A | 9/1996 | Owens et al. |
| 5,554,108 A | 9/1996 | Browning et al. |
| 5,558,506 A | 9/1996 | Simmons et al. |
| 5,567,118 A | 10/1996 | Grgurich et al. |
| 5,570,716 A | 11/1996 | Kamen et al. |
| 5,573,385 A | 11/1996 | Chevallier |
| 5,578,070 A | 11/1996 | Utterberg |
| 5,588,816 A | 12/1996 | Abbott et al. |
| 5,593,290 A * | 1/1997 | Greisch ............... F04B 19/006 417/478 |
| 5,601,420 A | 2/1997 | Warner et al. |
| 5,609,572 A | 3/1997 | Lang |
| 5,614,677 A | 3/1997 | Wamsiedler et al. |
| 5,624,409 A | 4/1997 | Seale |
| 5,628,908 A | 5/1997 | Kamen et al. |
| 5,630,710 A | 5/1997 | Tune et al. |
| 5,634,896 A | 6/1997 | Bryant et al. |
| 5,640,995 A | 6/1997 | Packard et al. |
| 5,641,405 A | 6/1997 | Keshaviah et al. |
| 5,641,892 A | 6/1997 | Larkins et al. |
| 5,643,205 A | 7/1997 | Utterberg |
| 5,645,531 A | 7/1997 | Thompson et al. |
| 5,647,733 A | 7/1997 | Augustyn et al. |
| 5,653,251 A | 8/1997 | Handler |
| 5,656,032 A | 8/1997 | Kriesel |
| 5,658,133 A | 8/1997 | Anderson et al. |
| 5,660,722 A | 8/1997 | Nederlof |
| 5,667,368 A | 9/1997 | Augustyn et al. |
| 5,669,724 A | 9/1997 | Kato |
| 5,669,764 A | 9/1997 | Behringer et al. |
| 5,687,633 A | 11/1997 | Eady |
| 5,690,602 A | 11/1997 | Brown et al. |
| 5,698,262 A | 12/1997 | Soubeyrand et al. |
| 5,709,534 A | 1/1998 | O'Leary |
| D390,654 S | 2/1998 | Alsberg et al. |
| 5,713,865 A | 2/1998 | Manning et al. |
| 5,713,888 A | 2/1998 | Neuenfeldt et al. |
| 5,718,565 A | 2/1998 | Kuhn et al. |
| 5,718,567 A | 2/1998 | Rapp et al. |
| 5,725,363 A | 3/1998 | Bustgens et al. |
| 5,741,121 A | 4/1998 | O'Leary |
| 5,741,125 A | 4/1998 | Neftel et al. |
| 5,743,170 A | 4/1998 | Pascual et al. |
| 5,746,708 A | 5/1998 | Giesler et al. |
| 5,755,683 A | 5/1998 | Houle et al. |
| 5,764,034 A | 6/1998 | Bowman et al. |
| 5,769,387 A | 6/1998 | Perez |
| 5,771,914 A | 6/1998 | Ling et al. |
| 5,772,635 A | 6/1998 | Dastur et al. |
| 5,772,637 A | 6/1998 | Heinzmann et al. |
| 5,775,371 A | 7/1998 | Pan et al. |
| 5,782,575 A | 7/1998 | Vincent et al. |
| 5,782,805 A | 7/1998 | Meinzer et al. |
| 5,788,215 A | 8/1998 | Ryan |
| 5,799,207 A | 8/1998 | Wang et al. |
| 5,816,775 A | 10/1998 | Imai et al. |
| 5,816,779 A | 10/1998 | Lawless et al. |
| 5,836,750 A | 11/1998 | Cabuz |
| 5,840,151 A | 11/1998 | Munsch |
| 5,842,841 A | 12/1998 | Danby et al. |
| 5,843,035 A | 12/1998 | Bowman et al. |
| 5,848,881 A | 12/1998 | Frezza |
| 5,863,184 A | 1/1999 | Juterbock et al. |
| 5,868,696 A | 2/1999 | Giesler et al. |
| 5,873,853 A | 2/1999 | Keilman et al. |

(56) References Cited

U.S. PATENT DOCUMENTS

| | | |
|---|---|---|
| 5,902,096 A | 5/1999 | Behringer et al. |
| 5,906,598 A | 5/1999 | Giesler et al. |
| 5,921,951 A | 7/1999 | Morris |
| 5,924,448 A | 7/1999 | West |
| 5,925,011 A | 7/1999 | Faict et al. |
| 5,932,987 A | 8/1999 | McLoughlin |
| 5,934,885 A | 8/1999 | Farrell et al. |
| 5,935,099 A | 8/1999 | Peterson et al. |
| 5,938,634 A | 8/1999 | Packard |
| 5,989,423 A | 11/1999 | Kamen et al. |
| 5,993,174 A | 11/1999 | Konishi |
| 5,996,634 A | 12/1999 | Dennehey et al. |
| 6,003,835 A | 12/1999 | Moller |
| 6,013,057 A | 1/2000 | Danby et al. |
| 6,036,668 A | 3/2000 | Mathis |
| 6,036,680 A | 3/2000 | Horne et al. |
| 6,041,801 A | 3/2000 | Gray et al. |
| 6,042,784 A | 3/2000 | Wamsiedler et al. |
| 6,053,191 A | 4/2000 | Hussey |
| 6,065,389 A | 5/2000 | Riedlinger |
| 6,065,941 A | 5/2000 | Gray et al. |
| 6,068,612 A | 5/2000 | Bowman et al. |
| 6,071,090 A | 6/2000 | Miki et al. |
| 6,074,359 A | 6/2000 | Keshaviah et al. |
| 6,079,959 A | 6/2000 | Kingsford et al. |
| 6,099,492 A | 8/2000 | Le Boeuf |
| 6,105,829 A | 8/2000 | Snodgrass et al. |
| 6,106,246 A | 8/2000 | Steck et al. |
| 6,109,881 A | 8/2000 | Snodgrass et al. |
| 6,110,410 A | 8/2000 | Owens et al. |
| 6,118,207 A | 9/2000 | Ormerod et al. |
| 6,126,403 A | 10/2000 | Yamada |
| 6,129,517 A | 10/2000 | Danby et al. |
| 6,132,187 A | 10/2000 | Ericson |
| 6,136,565 A | 10/2000 | Best et al. |
| 6,152,705 A | 11/2000 | Kennedy et al. |
| 6,154,605 A | 11/2000 | Aonuma |
| 6,158,966 A | 12/2000 | Guespin et al. |
| 6,158,972 A | 12/2000 | Ruth |
| 6,164,621 A | 12/2000 | Bouchard et al. |
| 6,165,154 A | 12/2000 | Gray et al. |
| 6,168,394 B1 | 1/2001 | Forman et al. |
| 6,173,959 B1 | 1/2001 | Oikawa et al. |
| 6,178,996 B1 | 1/2001 | Suzuki |
| 6,179,801 B1 | 1/2001 | Holmes et al. |
| 6,184,356 B1 | 2/2001 | Anderson et al. |
| 6,189,857 B1 | 2/2001 | Zeger et al. |
| 6,190,136 B1 | 2/2001 | Meloche et al. |
| 6,192,745 B1 | 2/2001 | Tang et al. |
| 6,196,987 B1 | 3/2001 | Holmes et al. |
| 6,200,287 B1 | 3/2001 | Keller et al. |
| 6,206,644 B1 | 3/2001 | Pereira et al. |
| 6,208,107 B1 | 3/2001 | Maske et al. |
| 6,210,361 B1 | 4/2001 | Kamen et al. |
| 6,220,295 B1 | 4/2001 | Bouchard et al. |
| 6,223,130 B1 | 4/2001 | Gray et al. |
| 6,227,807 B1 | 5/2001 | Chase |
| 6,227,824 B1 | 5/2001 | Stehr |
| 6,228,047 B1 | 5/2001 | Dadson |
| 6,229,753 B1 | 5/2001 | Kono et al. |
| 6,231,537 B1 | 5/2001 | Holmes et al. |
| 6,234,773 B1 | 5/2001 | Hill et al. |
| 6,234,919 B1 | 5/2001 | Mizeracki et al. |
| 6,234,989 B1 | 5/2001 | Brierton et al. |
| 6,238,576 B1 | 5/2001 | Yajima |
| 6,250,502 B1 | 6/2001 | Cote et al. |
| 6,261,065 B1 | 7/2001 | Nayak et al. |
| 6,267,242 B1 | 7/2001 | Nagata et al. |
| 6,270,673 B1 | 8/2001 | Belt et al. |
| 6,280,406 B1 | 8/2001 | Dolecek et al. |
| 6,281,145 B1 | 8/2001 | Deguchi et al. |
| 6,284,142 B1 | 9/2001 | Muller |
| 6,285,155 B1 | 9/2001 | Maske et al. |
| 6,286,566 B1 | 9/2001 | Cline et al. |
| 6,293,926 B1 | 9/2001 | Sorensen et al. |
| 6,294,094 B1 | 9/2001 | Muller et al. |
| 6,296,450 B1 | 10/2001 | Westberg et al. |
| 6,297,322 B1 | 10/2001 | Ding et al. |
| 6,299,029 B1 | 10/2001 | Bonningue |
| 6,305,793 B1 | 10/2001 | Haines |
| 6,315,707 B1 | 11/2001 | Smith et al. |
| 6,315,754 B1 | 11/2001 | Daoud et al. |
| 6,316,864 B1 | 11/2001 | Ormerod |
| 6,322,488 B1 | 11/2001 | Westberg et al. |
| 6,325,775 B1 | 12/2001 | Thom et al. |
| 6,337,049 B1 | 1/2002 | Tamari |
| RE37,553 E | 2/2002 | Ciavarini et al. |
| 6,343,539 B1 | 2/2002 | Du |
| 6,343,614 B1 | 2/2002 | Gray et al. |
| 6,345,962 B1 | 2/2002 | Sutter |
| 6,348,156 B1 | 2/2002 | Vishnoi et al. |
| 6,350,110 B1 | 2/2002 | Martin |
| 6,361,518 B1 | 3/2002 | Brierton et al. |
| 6,364,857 B1 | 4/2002 | Gray et al. |
| 6,367,669 B1 | 4/2002 | Au et al. |
| 6,382,923 B1 | 5/2002 | Gray |
| 6,382,934 B2 | 5/2002 | Budde |
| 6,383,158 B1 | 5/2002 | Utterberg et al. |
| 6,402,486 B1 | 6/2002 | Steck et al. |
| 6,406,276 B1 | 6/2002 | Normand et al. |
| 6,409,696 B1 | 6/2002 | Toavs et al. |
| 6,416,293 B1 | 7/2002 | Bouchard et al. |
| 6,416,295 B1 | 7/2002 | Nagai et al. |
| 6,419,822 B2 | 7/2002 | Muller et al. |
| 6,446,611 B2 | 9/2002 | Ishikawa |
| 6,455,676 B1 | 9/2002 | Weickert et al. |
| 6,464,474 B2 | 10/2002 | Schuecker |
| 6,471,855 B1 | 10/2002 | Odak et al. |
| 6,481,980 B1 * | 11/2002 | Vandlik ................. A61M 1/30 417/313 |
| 6,484,383 B1 | 11/2002 | Herklotz |
| 6,489,896 B1 | 12/2002 | Platt et al. |
| 6,491,656 B1 | 12/2002 | Morris |
| 6,494,694 B2 | 12/2002 | Lawless et al. |
| 6,497,674 B1 | 12/2002 | Steele et al. |
| 6,497,676 B1 | 12/2002 | Childers et al. |
| 6,503,062 B1 | 1/2003 | Gray et al. |
| 6,514,225 B1 | 2/2003 | Utterberg et al. |
| 6,519,569 B1 | 2/2003 | White et al. |
| 6,520,747 B2 | 2/2003 | Gray et al. |
| 6,524,231 B1 | 2/2003 | Westberg et al. |
| 6,529,573 B2 | 3/2003 | Olsher et al. |
| 6,537,445 B2 | 3/2003 | Muller |
| 6,542,761 B1 | 4/2003 | Jahn et al. |
| 6,554,587 B2 | 4/2003 | Paolini et al. |
| 6,558,343 B1 | 5/2003 | Neftel |
| 6,572,604 B1 | 6/2003 | Platt et al. |
| 6,575,599 B1 | 6/2003 | Imamura et al. |
| 6,579,253 B1 | 6/2003 | Burbank et al. |
| 6,589,028 B1 | 7/2003 | Eckerbom et al. |
| 6,592,542 B2 | 7/2003 | Childers et al. |
| 6,595,948 B2 | 7/2003 | Suzuki et al. |
| 6,603,229 B1 | 8/2003 | Toye |
| 6,604,908 B1 | 8/2003 | Bryant et al. |
| 6,644,930 B1 | 11/2003 | Kuismanen |
| 6,645,166 B2 | 11/2003 | Scheunert et al. |
| 6,645,177 B1 | 11/2003 | Sheam |
| 6,648,861 B2 | 11/2003 | Platt et al. |
| 6,663,355 B2 | 12/2003 | Kubo et al. |
| 6,663,359 B2 | 12/2003 | Gray |
| 6,670,323 B1 | 12/2003 | Looker et al. |
| 6,672,841 B1 | 1/2004 | Herkoltz et al. |
| 6,695,593 B1 | 2/2004 | Steck et al. |
| 6,695,803 B1 | 2/2004 | Robinson et al. |
| 6,709,417 B1 | 3/2004 | Houle et al. |
| 6,716,004 B2 | 4/2004 | Vandlik et al. |
| 6,723,062 B1 | 4/2004 | Westberg et al. |
| 6,725,726 B1 | 4/2004 | Adolfs et al. |
| 6,726,656 B2 | 4/2004 | Kamen et al. |
| 6,730,055 B2 | 5/2004 | Bainbridge et al. |
| 6,743,201 B1 | 6/2004 | Dönig et al. |
| 6,746,514 B2 | 6/2004 | Bedingfield et al. |
| 6,749,403 B2 | 6/2004 | Bryant et al. |
| 6,752,172 B2 | 6/2004 | Lauer |

(56) References Cited

U.S. PATENT DOCUMENTS

| | | |
|---|---|---|
| 6,752,599 B2 * | 6/2004 | Park .................... F04B 43/06 417/395 |
| 6,755,801 B2 | 6/2004 | Utterberg et al. |
| 6,758,975 B2 | 7/2004 | Peabody et al. |
| 6,759,007 B1 | 7/2004 | Westberg et al. |
| 6,759,014 B2 | 7/2004 | Dales et al. |
| 6,764,460 B2 | 7/2004 | Dolecek et al. |
| 6,764,761 B2 | 7/2004 | Eu et al. |
| 6,768,425 B2 | 7/2004 | Flaherty et al. |
| 6,774,517 B2 | 8/2004 | Kowalski et al. |
| 6,790,014 B2 | 9/2004 | Bowen |
| 6,790,195 B2 | 9/2004 | Steele et al. |
| 6,790,198 B1 | 9/2004 | White et al. |
| 6,796,215 B1 | 9/2004 | Hauser et al. |
| 6,800,054 B2 | 10/2004 | Westberg et al. |
| 6,808,369 B2 | 10/2004 | Gray et al. |
| 6,814,547 B2 | 11/2004 | Childers et al. |
| 6,821,432 B2 | 11/2004 | Metzner |
| 6,824,354 B2 | 11/2004 | Laing |
| 6,828,125 B1 | 12/2004 | Hoffman et al. |
| 6,830,553 B1 | 12/2004 | Burbank et al. |
| 6,846,161 B2 | 1/2005 | Kline et al. |
| 6,852,090 B2 | 2/2005 | Burbank et al. |
| 6,865,981 B2 | 3/2005 | Wiechers et al. |
| 6,869,538 B2 | 3/2005 | Yu et al. |
| 6,872,315 B2 | 3/2005 | Effenhauser et al. |
| 6,877,713 B1 | 4/2005 | Gray et al. |
| 6,889,765 B1 | 5/2005 | Traylor |
| 6,905,479 B1 | 6/2005 | Bouchard et al. |
| 6,929,751 B2 | 8/2005 | Bowman et al. |
| 6,935,617 B2 | 8/2005 | Mead et al. |
| 6,939,111 B2 | 9/2005 | Huitt et al. |
| 6,948,918 B2 | 9/2005 | Hansen |
| 6,949,079 B1 | 9/2005 | Westberg et al. |
| 6,953,323 B2 | 10/2005 | Childers et al. |
| 6,957,952 B1 | 10/2005 | Steck et al. |
| 6,971,859 B2 | 12/2005 | Yamamoto et al. |
| 6,973,922 B2 | 12/2005 | Yamada et al. |
| 6,978,798 B2 | 12/2005 | Baarda |
| 6,984,218 B2 | 1/2006 | Nayak et al. |
| 6,998,993 B2 | 2/2006 | Wang et al. |
| 7,008,153 B2 | 3/2006 | Rehn et al. |
| 7,014,605 B2 | 3/2006 | Weatherbee |
| 7,021,148 B2 | 4/2006 | Kuhn et al. |
| 7,029,245 B2 | 4/2006 | Maianti et al. |
| 7,033,539 B2 | 4/2006 | Krensky et al. |
| 7,041,076 B1 | 5/2006 | Westberg et al. |
| 7,044,432 B2 | 5/2006 | Beden et al. |
| 7,049,406 B2 | 5/2006 | Weickert et al. |
| 7,083,719 B2 | 8/2006 | Bowman et al. |
| 7,087,036 B2 | 8/2006 | Busby et al. |
| 7,107,837 B2 | 9/2006 | Lauman et al. |
| 7,114,531 B2 | 10/2006 | Silva |
| 7,115,107 B2 | 10/2006 | Delnevo et al. |
| 7,115,228 B2 | 10/2006 | Lundtveit et al. |
| 7,134,849 B1 | 11/2006 | Steck et al. |
| 7,147,613 B2 | 12/2006 | Burbank et al. |
| 7,153,286 B2 | 12/2006 | Busby et al. |
| 7,160,087 B2 | 1/2007 | Fathallah et al. |
| 7,166,231 B2 | 1/2007 | Westberg et al. |
| 7,175,606 B2 | 2/2007 | Bowman et al. |
| 7,195,607 B2 | 3/2007 | Westberg et al. |
| 7,198,072 B2 | 4/2007 | Silva |
| 7,211,560 B2 | 5/2007 | Looker et al. |
| 7,232,435 B2 | 6/2007 | Hildebrand et al. |
| 7,236,936 B2 | 6/2007 | White et al. |
| 7,238,164 B2 | 7/2007 | Childers et al. |
| 7,255,680 B1 | 8/2007 | Gharib |
| 7,258,534 B2 | 8/2007 | Fathallah et al. |
| 7,261,559 B2 | 8/2007 | Smith et al. |
| 7,267,661 B2 | 9/2007 | Susi |
| 7,273,465 B2 | 9/2007 | Ash |
| 7,284,966 B2 | 10/2007 | Xu et al. |
| 7,306,578 B2 | 12/2007 | Gray et al. |
| 7,318,819 B2 | 1/2008 | Lee et al. |
| 7,331,935 B2 | 2/2008 | Barere |
| 7,338,469 B2 | 3/2008 | Barker et al. |
| 7,338,472 B2 | 3/2008 | Shearn |
| 7,345,025 B2 | 3/2008 | Symonds et al. |
| 7,347,836 B2 | 3/2008 | Peterson et al. |
| 7,390,311 B2 | 6/2008 | Hildebrand et al. |
| 7,398,183 B2 | 7/2008 | Holland et al. |
| 7,399,637 B2 | 7/2008 | Wright et al. |
| 7,404,809 B2 | 7/2008 | Susi |
| 7,410,475 B2 | 8/2008 | Krensky et al. |
| 7,422,905 B2 | 9/2008 | Clague et al. |
| 7,454,314 B2 | 11/2008 | Holland et al. |
| 7,461,968 B2 | 12/2008 | Demers et al. |
| 7,479,522 B2 | 1/2009 | Zhu |
| 7,481,628 B2 | 1/2009 | Yamamoto et al. |
| 7,490,021 B2 | 2/2009 | Holland et al. |
| 7,500,962 B2 | 3/2009 | Childers et al. |
| 7,517,199 B2 | 4/2009 | Reed et al. |
| 7,517,387 B2 | 4/2009 | Chevallet et al. |
| 7,527,483 B1 | 5/2009 | Glauber |
| 7,553,295 B2 | 6/2009 | Susi |
| 7,554,179 B2 | 6/2009 | Shim et al. |
| 7,556,616 B2 | 7/2009 | Fathallah et al. |
| 7,575,564 B2 | 8/2009 | Childers |
| 7,594,801 B2 | 9/2009 | Udagawa |
| 7,618,948 B2 | 11/2009 | Kaemmerer |
| 7,632,080 B2 | 12/2009 | Tracey et al. |
| 7,645,258 B2 | 1/2010 | White et al. |
| 7,648,627 B2 | 1/2010 | Beden et al. |
| 7,654,976 B2 | 2/2010 | Peterson et al. |
| 7,658,598 B2 | 2/2010 | Reed et al. |
| 7,658,958 B2 | 2/2010 | Hansen |
| 7,662,286 B2 | 2/2010 | Childers et al. |
| 7,699,966 B2 | 4/2010 | Qin et al. |
| 7,705,880 B2 | 4/2010 | Dvir et al. |
| 7,717,682 B2 * | 5/2010 | Orr ........................ F04B 7/02 417/395 |
| 7,766,055 B2 | 8/2010 | Unger et al. |
| 7,776,006 B2 | 8/2010 | Childers et al. |
| 7,789,849 B2 | 9/2010 | Busby et al. |
| 7,794,141 B2 | 9/2010 | Perry et al. |
| 7,801,097 B2 | 9/2010 | Bahr et al. |
| 7,811,067 B2 | 10/2010 | Dietzsch et al. |
| 7,815,595 B2 | 10/2010 | Busby et al. |
| 7,901,376 B2 | 3/2011 | Steck et al. |
| 7,909,795 B2 | 3/2011 | Childers et al. |
| 7,935,074 B2 | 5/2011 | Plahey et al. |
| 7,981,280 B2 | 7/2011 | Carr et al. |
| 7,998,101 B2 | 8/2011 | Ash |
| 8,038,640 B2 | 10/2011 | Orr |
| 8,047,815 B2 | 11/2011 | Sarvard et al. |
| 8,066,671 B2 | 11/2011 | Busby et al. |
| 8,075,526 B2 | 12/2011 | Busby et al. |
| 8,142,397 B2 | 3/2012 | Patzer |
| 8,197,231 B2 | 6/2012 | Orr |
| 8,197,439 B2 | 6/2012 | Wang et al. |
| 8,206,338 B2 | 6/2012 | Childers et al. |
| 8,292,594 B2 | 10/2012 | Tracey et al. |
| 8,292,600 B2 | 10/2012 | Reed et al. |
| 8,317,492 B2 | 10/2012 | Demers et al. |
| 8,360,750 B2 | 1/2013 | Ferk et al. |
| 8,366,921 B2 | 2/2013 | Beden et al. |
| 8,409,441 B2 | 4/2013 | Wilt |
| 8,454,324 B2 | 6/2013 | Grapes |
| 8,512,553 B2 | 8/2013 | Cicchello et al. |
| 8,556,225 B2 | 10/2013 | Gray |
| 8,562,834 B2 | 10/2013 | Kamen et al. |
| 8,721,879 B2 | 5/2014 | van der Merwe et al. |
| 2001/0034502 A1 | 10/2001 | Moberg et al. |
| 2001/0037763 A1 | 11/2001 | Deguchi et al. |
| 2001/0038796 A1 | 11/2001 | Schluecker |
| 2002/0045851 A1 | 4/2002 | Suzuki et al. |
| 2002/0062109 A1 | 5/2002 | Lauer |
| 2002/0072718 A1 | 6/2002 | Brugger et al. |
| 2002/0107474 A1 | 8/2002 | Noack |
| 2002/0147423 A1 | 10/2002 | Burbank et al. |
| 2003/0018395 A1 | 1/2003 | Crnkovich et al. |
| 2003/0028144 A1 | 2/2003 | Duchon et al. |
| 2003/0029451 A1 | 2/2003 | Blair et al. |

(56) References Cited

U.S. PATENT DOCUMENTS

| | | |
|---|---|---|
| 2003/0042181 A1 | 3/2003 | Metzner |
| 2003/0045772 A1 | 3/2003 | Reich et al. |
| 2003/0100882 A1 | 5/2003 | Beden et al. |
| 2003/0136189 A1 | 7/2003 | Lauman et al. |
| 2003/0194332 A1* | 10/2003 | Jahn .............. F04B 43/0733 417/395 |
| 2003/0200812 A1 | 10/2003 | Kuhn et al. |
| 2003/0204162 A1 | 10/2003 | Childers et al. |
| 2003/0217957 A1 | 11/2003 | Bowman et al. |
| 2003/0217961 A1 | 11/2003 | Hopping |
| 2003/0217975 A1 | 11/2003 | Yu et al. |
| 2003/0218623 A1 | 11/2003 | Krensky et al. |
| 2003/0220599 A1 | 11/2003 | Lundtveit et al. |
| 2003/0220605 A1 | 11/2003 | Bowman et al. |
| 2003/0220607 A1 | 11/2003 | Busby et al. |
| 2003/0220608 A1 | 11/2003 | Huitt et al. |
| 2003/0220609 A1 | 11/2003 | Childers et al. |
| 2003/0220627 A1 | 11/2003 | Distler et al. |
| 2004/0001766 A1 | 1/2004 | Maianti et al. |
| 2004/0010223 A1 | 1/2004 | Busby et al. |
| 2004/0019313 A1 | 1/2004 | Childers et al. |
| 2004/0019320 A1 | 1/2004 | Childers et al. |
| 2004/0031756 A1 | 2/2004 | Suzuki et al. |
| 2004/0064080 A1 | 4/2004 | Cruz et al. |
| 2004/0067161 A1 | 4/2004 | Axelsson |
| 2004/0082903 A1 | 4/2004 | Micheli |
| 2004/0084647 A1 | 5/2004 | Beden et al. |
| 2004/0109769 A1 | 6/2004 | Jahn et al. |
| 2004/0115068 A1 | 6/2004 | Hansen et al. |
| 2004/0135078 A1 | 7/2004 | Mandro et al. |
| 2004/0136843 A1* | 7/2004 | Jahn .............. F04B 43/0733 417/395 |
| 2004/0156745 A1 | 8/2004 | Vandlik et al. |
| 2004/0195190 A1 | 10/2004 | Min et al. |
| 2004/0238416 A1 | 12/2004 | Burbank et al. |
| 2005/0054968 A1 | 3/2005 | Giannella |
| 2005/0074340 A1 | 4/2005 | Xu et al. |
| 2005/0100450 A1 | 5/2005 | Bryant et al. |
| 2005/0118041 A1 | 6/2005 | Yamamoto et al. |
| 2005/0126998 A1 | 6/2005 | Childers |
| 2005/0139002 A1 | 6/2005 | Onishi |
| 2005/0197612 A1 | 9/2005 | Levin et al. |
| 2005/0230292 A1 | 10/2005 | Beden et al. |
| 2005/0234384 A1 | 10/2005 | Westberg et al. |
| 2006/0002823 A1 | 1/2006 | Feldstein |
| 2006/0045766 A1 | 3/2006 | Harttig |
| 2006/0079826 A1 | 4/2006 | Beden et al. |
| 2006/0161092 A1 | 7/2006 | Westberg et al. |
| 2006/0195064 A1 | 8/2006 | Plahey et al. |
| 2006/0261526 A1 | 11/2006 | Bantle et al. |
| 2007/0100873 A1 | 5/2007 | Yako et al. |
| 2007/0112297 A1 | 5/2007 | Plahey et al. |
| 2007/0122291 A1 | 5/2007 | Okumura et al. |
| 2007/0140873 A1 | 6/2007 | Grapes |
| 2007/0149913 A1 | 6/2007 | Busby et al. |
| 2007/0193940 A1 | 8/2007 | Duchamp et al. |
| 2007/0201993 A1 | 8/2007 | Terentiev et al. |
| 2007/0213651 A1 | 9/2007 | Busby et al. |
| 2007/0213653 A1 | 9/2007 | Childers et al. |
| 2007/0269340 A1 | 11/2007 | Dannenmaier et al. |
| 2008/0015493 A1 | 1/2008 | Childers et al. |
| 2008/0033346 A1 | 2/2008 | Childers et al. |
| 2008/0063543 A1 | 3/2008 | Xu et al. |
| 2008/0077068 A1 | 3/2008 | Orr |
| 2008/0103429 A1 | 5/2008 | Shang et al. |
| 2008/0125693 A1 | 5/2008 | Gavin et al. |
| 2008/0138223 A1 | 6/2008 | Lanigan et al. |
| 2008/0208103 A1 | 8/2008 | Demers et al. |
| 2008/0216898 A1 | 9/2008 | Grant et al. |
| 2008/0240929 A1 | 10/2008 | Kamen et al. |
| 2008/0253912 A1 | 10/2008 | Demers et al. |
| 2009/0004033 A1 | 1/2009 | Demers et al. |
| 2009/0095679 A1 | 4/2009 | Demers et al. |
| 2009/0099498 A1 | 4/2009 | Demers et al. |
| 2009/0137940 A1 | 5/2009 | Orr |
| 2009/0169402 A1 | 7/2009 | Stenberg |
| 2009/0212248 A1 | 8/2009 | Kozak |
| 2010/0104458 A1 | 4/2010 | Grapes |
| 2010/0211044 A1 | 8/2010 | Dacquay et al. |
| 2010/0241062 A1 | 9/2010 | Morris et al. |
| 2010/0286614 A1 | 11/2010 | Ring |
| 2011/0015610 A1 | 1/2011 | Plahey et al. |
| 2011/0041935 A1 | 2/2011 | Zhou et al. |
| 2011/0092895 A1 | 4/2011 | Yardimci et al. |
| 2011/0125085 A1 | 5/2011 | McGill et al. |
| 2011/0137237 A1 | 6/2011 | Prisco et al. |
| 2011/0293450 A1 | 12/2011 | Grimes et al. |
| 2011/0303598 A1 | 12/2011 | Lo et al. |
| 2012/0065581 A1 | 3/2012 | Childers et al. |
| 2012/0123322 A1 | 5/2012 | Scarpaci et al. |
| 2012/0209169 A1 | 8/2012 | Morris et al. |
| 2012/0224984 A1 | 9/2012 | Orr |
| 2012/0230844 A1 | 9/2012 | Farrell et al. |
| 2012/0232469 A1 | 9/2012 | Medina |
| 2012/0271226 A1 | 10/2012 | Farrell et al. |
| 2012/0308412 A1 | 12/2012 | Rochat |
| 2013/0118961 A1 | 5/2013 | Beden et al. |
| 2013/0118970 A1 | 5/2013 | Beden et al. |
| 2013/0155105 A1 | 6/2013 | Boldyrev et al. |
| 2013/0184638 A1 | 7/2013 | Scarpaci et al. |
| 2013/0330208 A1 | 12/2013 | Ly et al. |
| 2013/0331774 A1 | 12/2013 | Farrell et al. |

FOREIGN PATENT DOCUMENTS

| | | |
|---|---|---|
| CN | 200943571 | 9/2007 |
| DE | 2628238 | 1/1978 |
| DE | 2827648 | 1/1979 |
| DE | 3441054 | 5/1985 |
| DE | 4006785 | 9/1990 |
| DE | 4336336 | 5/1994 |
| DE | 19837667 | 3/2000 |
| DE | 19919572 | 11/2000 |
| DE | 19919572 A1 | 11/2000 |
| DE | 10042324 | 2/2002 |
| DE | 10046651 | 4/2002 |
| DE | 19919572 | 4/2002 |
| DE | 19919572 C2 | 4/2002 |
| DE | 10053441 | 5/2002 |
| DE | 69618766 | 8/2002 |
| DE | 10143137 | 4/2003 |
| DE | 10157924 | 6/2003 |
| DE | 102007059239 | 6/2009 |
| EP | 257279 | 3/1988 |
| EP | 257279 A1 | 3/1988 |
| EP | 0432146 | 6/1991 |
| EP | 0314379 | 8/1991 |
| EP | 0484575 | 5/1992 |
| EP | 0086731 | 8/1993 |
| EP | 0410125 | 8/1993 |
| EP | 0410125 B1 | 8/1993 |
| EP | 0728509 | 8/1996 |
| EP | 0848193 | 6/1998 |
| EP | 0856321 | 8/1998 |
| EP | 0947814 | 10/1999 |
| EP | 0947814 B2 | 10/1999 |
| EP | 0956876 | 11/1999 |
| EP | 0956876 A1 | 11/1999 |
| EP | 1055853 | 11/2000 |
| EP | 1072868 | 1/2001 |
| EP | L072868 | 1/2001 |
| EP | 1126895 | 8/2001 |
| EP | 1353069 | 10/2003 |
| EP | 1529545 | 5/2005 |
| GB | 2036168 A | 6/1980 |
| GB | 2101232 | 1/1983 |
| GB | 2101232 A | 1/1983 |
| GB | 1483702 | 8/1997 |
| GB | 2331796 | 6/1999 |
| JP | S5551977 | 4/1980 |
| JP | 0396850 | 4/1991 |
| JP | 0396850 A | 4/1991 |
| JP | H0388978 | 4/1991 |
| JP | 04191755 | 7/1992 |

(56) References Cited

FOREIGN PATENT DOCUMENTS

| | | |
|---|---|---|
| JP | H053118 | 1/1993 |
| JP | 06154314 | 6/1994 |
| JP | 06002650 | 11/1994 |
| JP | 08028722 | 3/1996 |
| JP | H11324923 | 11/1999 |
| JP | 11347115 | 12/1999 |
| JP | 2000070358 | 3/2000 |
| JP | 2000346214 | 12/2000 |
| JP | 2005526575 | 9/2005 |
| JP | 2007120446 | 5/2007 |
| RU | 2L05194 | 2/1998 |
| RU | 2105194 | 2/1998 |
| WO | 8402473 | 7/1984 |
| WO | WO1984/002473 | 7/1984 |
| WO | 8601115 | 2/1986 |
| WO | W01986001115 | 2/1986 |
| WO | WO1986001115 | 2/1986 |
| WO | W08703065 | 5/1987 |
| WO | WO8703065 | 5/1987 |
| WO | W01992019868 | 11/1992 |
| WO | WO1992019868 | 11/1992 |
| WO | WO1994015660 | 7/1994 |
| WO | WO1994015660 A1 | 7/1994 |
| WO | 9420155 | 9/1994 |
| WO | 9625064 | 8/1996 |
| WO | 9625064 A2 | 8/1996 |
| WO | 1997016214 | 5/1997 |
| WO | 1997037703 | 10/1997 |
| WO | 9822165 | 5/1998 |
| WO | W01998022167 | 5/1998 |
| WO | WO1998022167 A1 | 5/1998 |
| WO | 0023140 | 4/2000 |
| WO | 0033898 | 6/2000 |
| WO | WO0104584 | 1/2001 |
| WO | WOOL04584 | 1/2001 |
| WO | 0117605 | 3/2001 |
| WO | W00117607 | 3/2001 |
| WO | WO0117607 | 3/2001 |
| WO | W0200 L/090334 | 11/2001 |
| WO | WO2001/090334 | 11/2001 |
| WO | 0225146 | 3/2002 |
| WO | 0225225 | 3/2002 |
| WO | W02007013049 | 2/2007 |
| WO | WO2007013049 | 2/2007 |
| WO | W02007006030 | 6/2007 |
| WO | WO2007006030 A3 | 6/2007 |
| WO | 2009071069 | 6/2009 |
| WO | WO2011045167 A1 | 4/2011 |
| WO | WO20110451167 | 4/2011 |

OTHER PUBLICATIONS

Olsson et al., "A valve-less planar fluid pump with two pumps chambers," Sensors and Actuators A 46-47, pp. 549-556.
Air Operated Double Diaphragm Pumps 1/2" Model, Operations and Maintenance Instructions, Graymills, www.graymills.com—pp. 1-20.
Operator's Manual—66610X-X-C, 1" Diaphragm Pump 1.1 Ratio (Metallic), pp. 1-8.
Double Diaphragm Pumps—Concept and Theory Training—Graco, Inc. 1996 Graco Inc. Form No. 321-048 1/96, pp. 1-40.
Cervino et al., Novel Left Ventricular Assist Systems I and II for Cardiac Recovery, The Driver, Cardivasvular Devices. Texas Heart Institute Journal, Novel LVAS I and II: The Driver, vol. 32, No. 4 (2005), pp. 535-540.
Taylor et al., "Simulation of microfluidic pumping in a genomic DNA blood-processing cassette," Journal of Micromechanics and Microengineering, Ph: S0960 1317(03)39447.1, 13 (2013), pp. 201 208.
Hoerstrup, S. MD, "Functional Living Trileaflet Heart Valves Grown In Vitro," Circulation http://www.circulationaha.org, Nov. 7, 2000, III-44-49.
Reexamination Control No. 90/013,241, Request for Ex Parte Reexamination dated May 14, 2014.
Reexamination Control No. 90/013,241, Order Granting Ex Parte Reexamination mailing date Jun. 3, 2014.
Reexamination Control No. 90/013,241, Office Action in Ex Parte Reexamination dated Aug. 6, 2014.
Reexamination Control No. 90/013,241, Final Office Action in Ex Parte Reexamination dated Nov. 7, 2014.
Reexamination Control No. 90/020,070, Request for Ex Parte Reexamination dated May 14, 2014.
Reexamination Control No. 90/020,070, Order Granting Ex Parte Reexamination mailing date Jun. 11, 2014.
Reexamination Control No. 90/020,070, Office Action in Ex Parte Reexamination dated Sep. 9, 2014.
Reexamination Control No. 90/020,070, Final Office Action in Ex Parte Reexamination dated Mar. 3, 2015.
Reexamination Control No. 90/020,070, Advisory Action in Ex Parte Reexamination dated Jun. 23, 2015.
Reexamination Control No. 90/020,069, Request for Ex Parte Reexamination May 14, 2014.
Reexamination Control No. 90/020,069, Order Granting Ex Parte Reexamination mailing date Jul. 3, 2014.
Reexamination Control No. 90/020,069, Office Action in Ex Parte Reexamination dated Sep. 26, 2014.
Reexamination Control No. 90/020,069, Office Action in Ex Parte Reexamination dated May 27, 2015.
Reexamination Control No. 90/020,069, Advisory Action in Ex Parte Reexamination dated Aug. 12, 2015.
Reexamination Control No. 90/020,069, Advisory Action in Ex Parte Reexamination dated Sep. 11, 2015.
Bolegoh, Gordon, "Pumps: Reference Guide", p. 24, 3rd edition, 2001.
Ronco et al., "Evolution of Machines for Automated Peritoneal Dialysis", in Automated Peritoneal Dialysis, Contributions to Nephrology, vol. 129, pp. 142-161, 1999.
Sleep Safe Operating Instructions, Software Version 0.5, Apr. 1999.
Sleep Safe Operating Instructions, Software Version 1.0, Oct. 2000.
Sleep Safe Technical Manual, Dec. 2001.
Sleep Safe Operating Instructions, Jan. 2002.
Sleep Safe Communicating Therapy, Mar. 1998.
Sleep Safe Kommunizierte Therapie, May 1998.
Innovative Technologies in Peritoneal Dialysis, Sleep Safe Concept, Oct. 13, 1999 (4 attachments).
TL™ Pump Brochure, TL Systems Corporation, Apr. 1975.
Avolio, Glenn, "Principles of Rotary Optical Encoders," Sensors Journal of Machine Perception, vol. 10, No. 4, pp. 10-18, 1993.
Gambro®, "DEHP-free cartridge blood sets," © Nov. 2004, Gambro, Inc., Lakewood, Co, 4 pp.
Gambro®, "Prisma® HF 1000, For Increased Filtration Capacity", © Aug. 2001, Gambro Renal Products, Inc., Lakewood, CO, 2 pp.
Gambro®, "Prisma® M60 and M100 Pre-Pump Infusion Sets—Introducing: The unique solution that enables Physicians to choose a predilution method that meets the needs of their patients", © 2004, Gambro Inc., Lakewood, CO, 4 pp.
Gambro®, "Prismaflex™ anticipating critical care needs and taking our innovative response . . . to new heights," © 2004, Gambro Inc., Lakewood, CO, 8 pp.
Liberty Cycler Operator's Manual, 2003-2004.
Manns et al., "The acu-men: A new device for continuous renal replacement therapy in acute renal failure," Kidney International, vol. 54, pp. 268-274, 1998.
Newton IQ Cycler Operator Manual, Part No. 470203 Rev. F, 2000-2006.
Operator's Instructions, Fresenius 90/2 Peritoneal Therapy Cycler, Part No. 470016, Rev. B, 1991.
Operator's Manual, Serena, Program Version 3.xx—English, 2002.
Sleep Safe Operating Instructions, Software Version 0.9, Part No. 677 805 1; Aug. 2000.
Sleep Safe Technical Manual, Part No. 677 807 1; Aug. 2000.
Laser et al. Topical Review of micropumps, Institute of Physics Publishing, J. Mieromech. Microeng. 14 (2004), Pll: S0960-1317(04)06813-5, R35-R64.

(56) References Cited

OTHER PUBLICATIONS

Olsson, et al., "A valve-less planar Huid pump with two pumps chambers," Sensors and Actuators A 46-47, pp. 549-556.
Double Diaphragm Pumps—Concept and 111cory Training—Graco, Inc. 1996 Graco Inc. Form No. 321-048 1/96, pp. 1-40.
Hoerstrup, S. MD, "Functional Living Trileatlet Heart Valves Grown In Vitro," Circulation http://www.circulationaha.org, Nov. 7, 2000, III-44-49.
Reexamination Control No. 90/013,241, Order Gnmling Ex Parle Reexamination mailing date Jun. 3, 2004.
Reexamination Control No. 90/020,070, Final Otlice Action in Ex Parte Reexamination dated Mar. 3, 2015.
Reexamination Control No. 90/020,069, Office Action 111 Ex Parte Reexamination dated Sep. 26, 2014.
Reexamination Control No. 90/020,069, Office Action m Ex Parte Reexamination dated May 27, 2015.

* cited by examiner

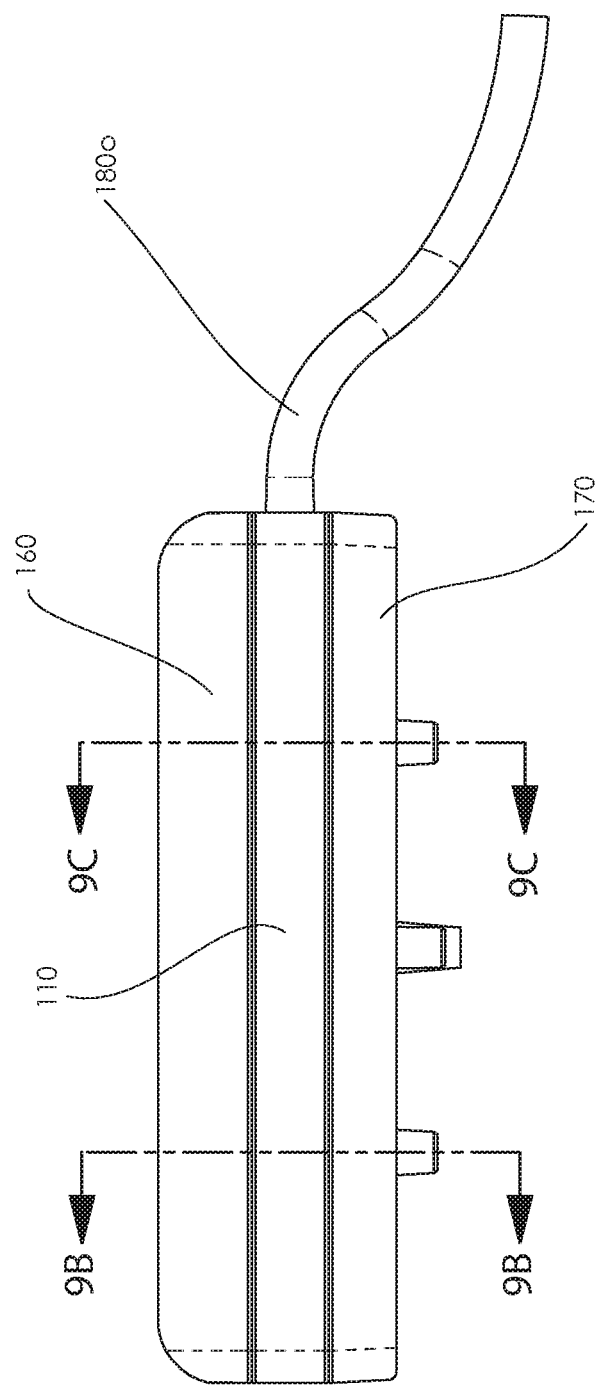

MEDICAL FLUID DELIVERY DEVICE
ACTUATED VIA MOTIVE FLUID

PRIORITY CLAIM

This application claims priority to and the benefit as a continuation of U.S. patent application Ser. No. 14/558,021, filed Dec. 2, 2014, entitled DIAPHRAGM PUMPS AND PUMPING SYSTEMS, which is a continuation of U.S. patent application Ser. No. 13/472,099, filed May 15, 2012, entitled DIAPHRAGM PUMP AND PUMPING SYSTEMS, now U.S. Pat. No. 8,932,032 issued Jan. 13, 2015, which is a continuation of U.S. patent application Ser. No. 11/945,177, filed Nov. 26, 2007, entitled DIAPHRAGM PUMP AND RELATED METHODS, now U.S. Pat. No. 8,197,231 issued Jun. 12, 2012, which is a continuation-in-part of U.S. patent application Ser. No. 11/484,061, filed Jul. 11, 2006, entitled DOUBLE DIAPHRAGM PUMP AND RELATED METHODS, now U.S. Pat. No. 7,717,682 issued on May 18, 2010, which claims priority to U.S. Provisional Application No. 60/699,262, filed Jul. 13, 2005, entitled DOUBLE DIAPHRAGM PUMP AND RELATED METHODS, the entire contents of each of which are incorporated herein by reference and relied upon. In particular, FIGS. 2 and 4A to 4C and associated disclosure of U.S. Pat. No. 7,717,682 teaching, among other structure, (i) left pump chamber 103*l* and right pump chamber 103*r* provided respectively on left and right (opposite) sides of process fluid body 110, and (ii) first inlet and outlet valve chambers 101*i*, 101*o* and second inlet and outlet chambers 102*i*, 102*o* provided respectively on opposite sides of process fluid body 110, are relied upon to support the present claims.

TECHNICAL FIELD

Certain embodiments described herein relate generally to the field of fluid transfer. More particularly, some embodiments described herein relate to fluid transfer having a relatively small amount or no amount of impurities introduced to the fluid being transferred and/or relatively little or no damage to the fluid being transferred.

BRIEF DESCRIPTION OF THE DRAWINGS

Understanding that drawings depict only typical embodiments of the invention and are not therefore to be considered to be limiting of its scope, the invention will be described and explained with additional specificity and detail through the use of the accompanying drawings. The drawings are listed below.

FIG. 9A is a side view of the double diaphragm pump of FIG. 1 which shows cutting lines 9B-9B and 9C-9C.

INDEX OF ELEMENTS IDENTIFIED IN THE DRAWINGS

Figure 1:
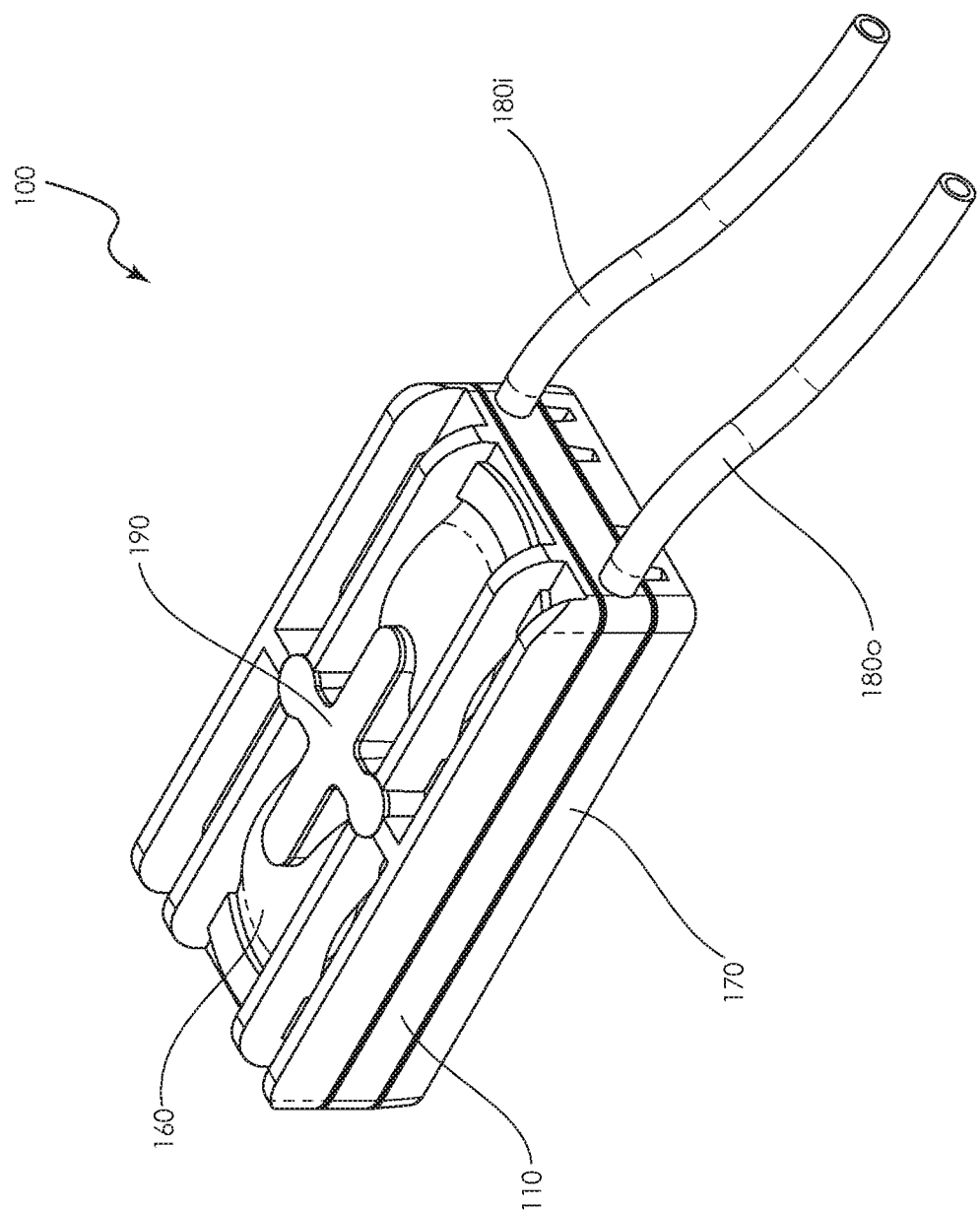
FIG. 1 is a perspective view of an embodiment of a double diaphragm blood pump.

Elements numbered in the drawings include:
100 double diaphragm pump
100a-h double diaphragm pumps
101i first inlet valve chamber
101o first outlet valve chamber
102i second inlet valve chamber
102o second outlet valve chamber
103a first pump chamber
103b second pump chamber
110 pump body
110' pump body with valve bypass channels
111i first inlet valve seat
111o first outlet valve seat
112i second inlet valve seat
112o second outlet valve seat
113a first chamber cavity
113b second chamber cavity
114a surface of first chamber cavity 113a
114b surface of second chamber cavity 113b
115a inclined region of first pump chamber 113a
115b inclined region of second pump chamber cavity 113b
116a rim of first pump chamber 113a
116b rim of second pump chamber cavity 113b
117a perimeter of first pump chamber cavity 113a
117b perimeter of second pump chamber cavity 113b
118i perimeter of first inlet valve seat 111i
118o perimeter of first outlet valve seat 111o
119i perimeter of second inlet valve seat 112i
119o perimeter of second outlet valve seat 112o
121i groove of first inlet valve seat 111i
121o groove of first outlet valve seat 111o
122i groove of second inlet valve seat 112i
122o groove of second outlet valve seat 112o
131i first inlet valve portal for fluid communication between inlet channel 138i and first inlet valve seat 111i
131o first outlet valve portal for fluid communication between first outlet valve seat 111o and outlet channel 138o
132i second inlet valve portal for fluid communication between inlet channel 138i and second inlet valve seat 112i
132o second outlet valve portal for fluid communication between second outlet valve seat 112o and outlet channel 138o
133i chamber channel for fluid communication between first chamber cavity 113a and first inlet valve seat 111i
133o chamber channel for fluid communication between first chamber cavity 113a and first outlet valve seat 111o
134i chamber channel for fluid communication between second chamber cavity 113b and second inlet valve seat 112i
134o chamber channel for fluid communication between second chamber cavity 113b and second outlet valve seat 112o
135i seat rim of first inlet valve seat 111i
135o seat rim of first outlet valve seat 111o
136i seat rim of second inlet valve seat 112i
136o seat rim of second outlet valve seat 112o
138i inlet channel
138o outlet channel
139i bypass channel between inlet channel 138i and first pump chamber 103a
139o bypass channel between first pump chamber 103a and outlet channel 138o
140a&b chamber diaphragms
141a first pump chamber diaphragm region of chamber diaphragms 140a, b
141b second pump chamber diaphragm region of chamber diaphragms 140a, b
142a-f holes in chamber diaphragm for assembly
150a&b valve diaphragms
151i first inlet valve region of valve diaphragms 150a&b
151o first outlet valve region of valve diaphragms 150a&b
152i second inlet valve region of valve diaphragms 150a&b
152o second outlet valve region of valve diaphragms 150a&b
160 chamber plate
161a first chamber actuation cavity
161b second chamber actuation cavity
162a&b air transfer bosses
163a passage between opening 164a and boss 162a
163b passage between opening 164b and boss 162b
164a opening between first chamber cavity 161a and passage 163a
164b opening between second chamber cavity 161b and passage 163b
165a&b cavity surface 166a&b
166a&b recess
166c&d inclined regions
167a&b rims
168a&b perimeters
169a-d assembly posts
170 valve plate
171i actuation cavity of first inlet valve 101i
171o actuation cavity of first outlet valve 101o
172i actuation cavity of second inlet valve 102i
172o actuation cavity of second outlet valve 102o
173i passage between actuation cavity 171i of first inlet valve 101i and boss 176a
173o passage between actuation cavity 171o of first outlet valve 101o and boss 176b
174i passage between actuation cavity 172i of second inlet valve 102i and boss 176c
174o passage between actuation cavity 172o of second outlet valve 102o and boss 176d
175 mounting hook
175a opening defined by mounting hook
176a-d air transfer bosses
177i groove for o-ring 192a
177o groove for o-ring 192b
178i groove for o-ring 192c
178o groove for o-ring 192d
179a-f assembly holes
180i inlet line
180o outlet line
190 manifold cover plate
192a-d valve o-rings
193a&b chamber o-rings
210 motive fluid valve
212 valve controller
220 pressure source
230 vacuum source
238 fluid source or blood uptake
239 fluid return, receiver, or destination
300 forming fixture 310 first plate
311a&b chamber region recess
312a&b o-ring groove
313a&b openings between forming recess 311a, b and vacuum port 318
314a&b surface of recess
318 vacuum port or passage
320 second plate
321a&b heating windows or portals
330 heater
331 heater surface
400 manifold mounting assembly
402a&b manifold covers
403a&b mounting latches
406 catch
407 motive fluid transfer boss
410 manifold base
411 motive fluid transfer boss
412 motive fluid transfer boss
413 motive fluid transfer boss
414 motive fluid transfer boss
415 motive fluid transfer boss
416 motive fluid transfer boss
417 transfer passage of manifold between air transfer bosses 412, 413, 414 and portal B
418 transfer passage of manifold between air transfer bosses 411, 415, 416 and portal A
421 flow restriction between air transfer boss 412 and transfer passage 418
422 flow restriction between air transfer boss 415 and transfer passage 417
431a-f o-rings
432a&b screws
433a&b washers
434a-d screws
435a&b brackets
436a-d fasteners
450 pump assembly
451 pump control system
452 processor
453 user control interface
454 enclosure
700 cardiopulmonary by-pass system
701 oxygenator
702 arterial tubing segment
703 arterial cannula
704 venous return catheter
705 venous tubing segment
706 reservoir
709 cardioplegia cannula
711 medical fluid bag
712 vent catheter
713 suction device
750 heart-assist system
753 cannula or attachment to vascular system on venous side
754 cannula or attachment to vascular system on arterial side
800 extracorporeal circuit
802 tubing segment on blood uptake from patient vascular system
803 drip chamber
804a&b pressure transducers
805 tubing segment
807 tubing segment
808 heparin pump
810 dialyzer
811 tubing segment
812 drip chamber
814 tubing segment on blood return to patient vascular system
820 dialyzing liquid system
825 air detector
1100 pump
1101i first inlet valve
1101o first outlet valve
1103a first pump chamber
1110 pump body
1133i chamber channel between first inlet valve and first pump chamber
1133o chamber channel between first pump chamber and first outlet valve
1135i rim of first inlet valve
1135o rim of first outlet valve
1138i inlet channel
1138o outlet channel
1140 one or more diaphragms
1141a diaphragm actuation region of first pump chamber
1151i diaphragm actuation region of first inlet valve
1151o diaphragm actuation region of first outlet valve
1160 chamber plate
1162a motive fluid transfer boss
1163a motive fluid passage
1173i motive fluid passage
1173o motive fluid passage
1176a motive fluid transfer boss
1176b motive fluid transfer boss
1180i inlet line
1180o outlet line
A first supply port connection between air valve 210 and manifold plate 400
B second supply port connection between air valve 210 and manifold plate 400
P patient

DETAILED DESCRIPTION

Figure 6A:
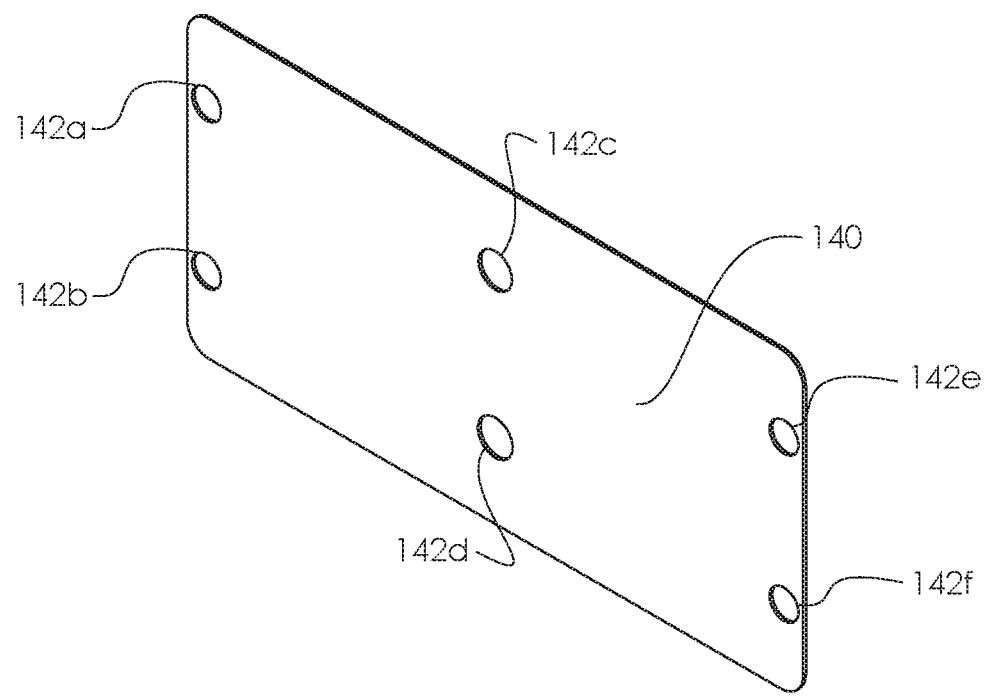
FIG. 6A is a perspective view of an embodiment of diaphragm media before regions have been formed.
Figure 16:
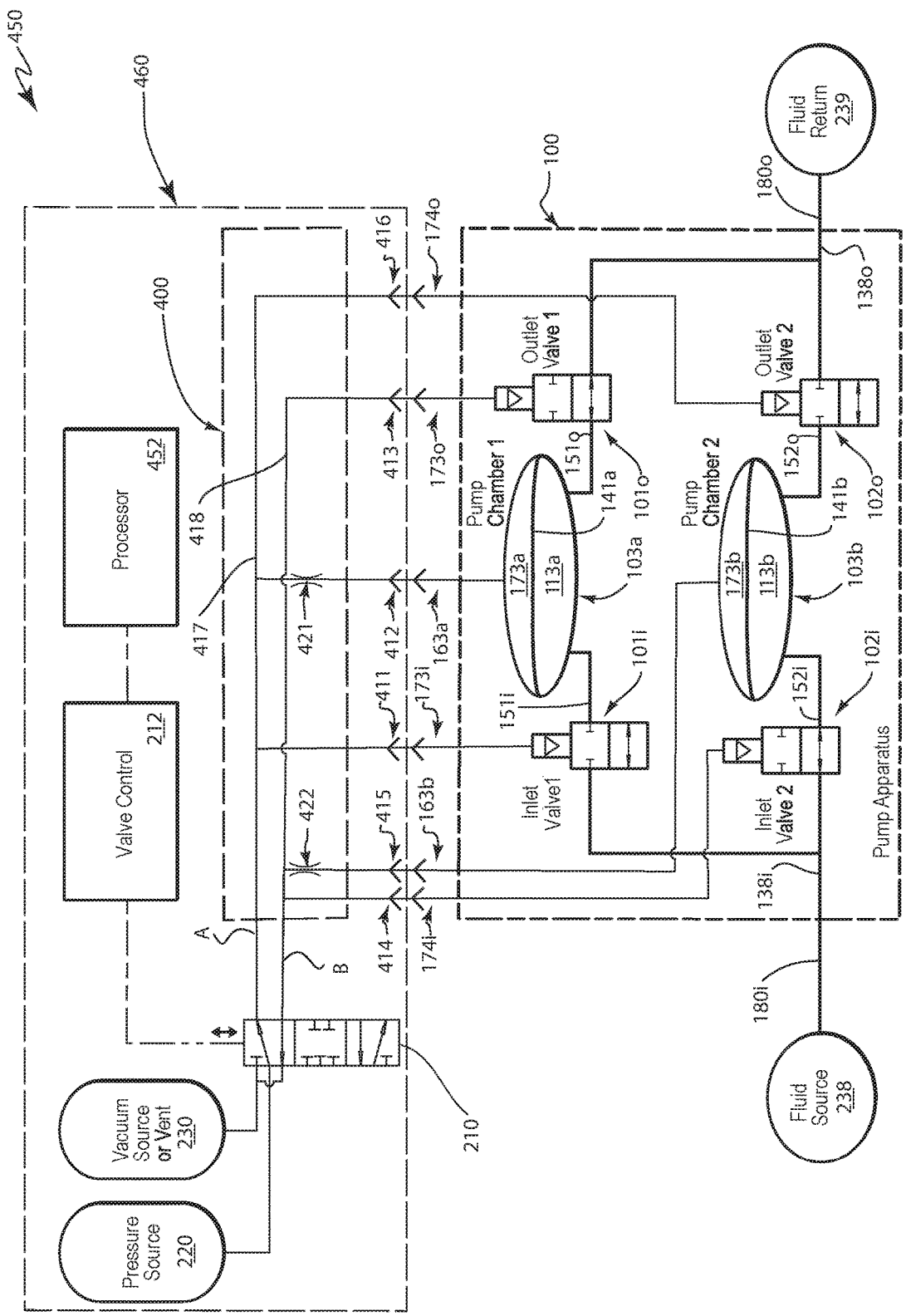
FIG. 16 is a schematic view of an embodiment of a double diaphragm pump as used in a method and system for transferring fluid.
Figure 17:
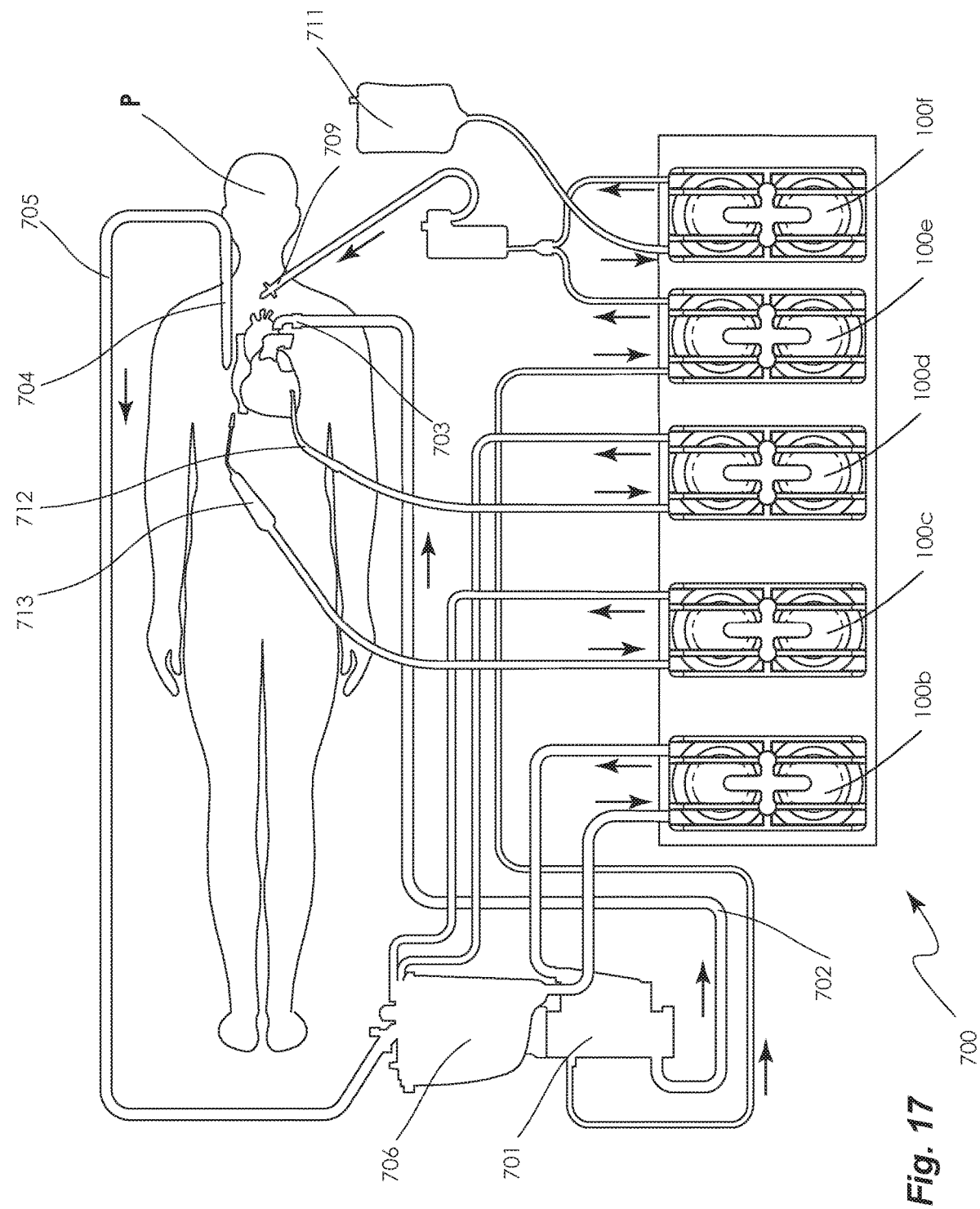
FIG. 17 is a schematic view of an embodiment of a cardiopulmonary by-pass system that includes multiple double diaphragm pumps.
Figure 18:
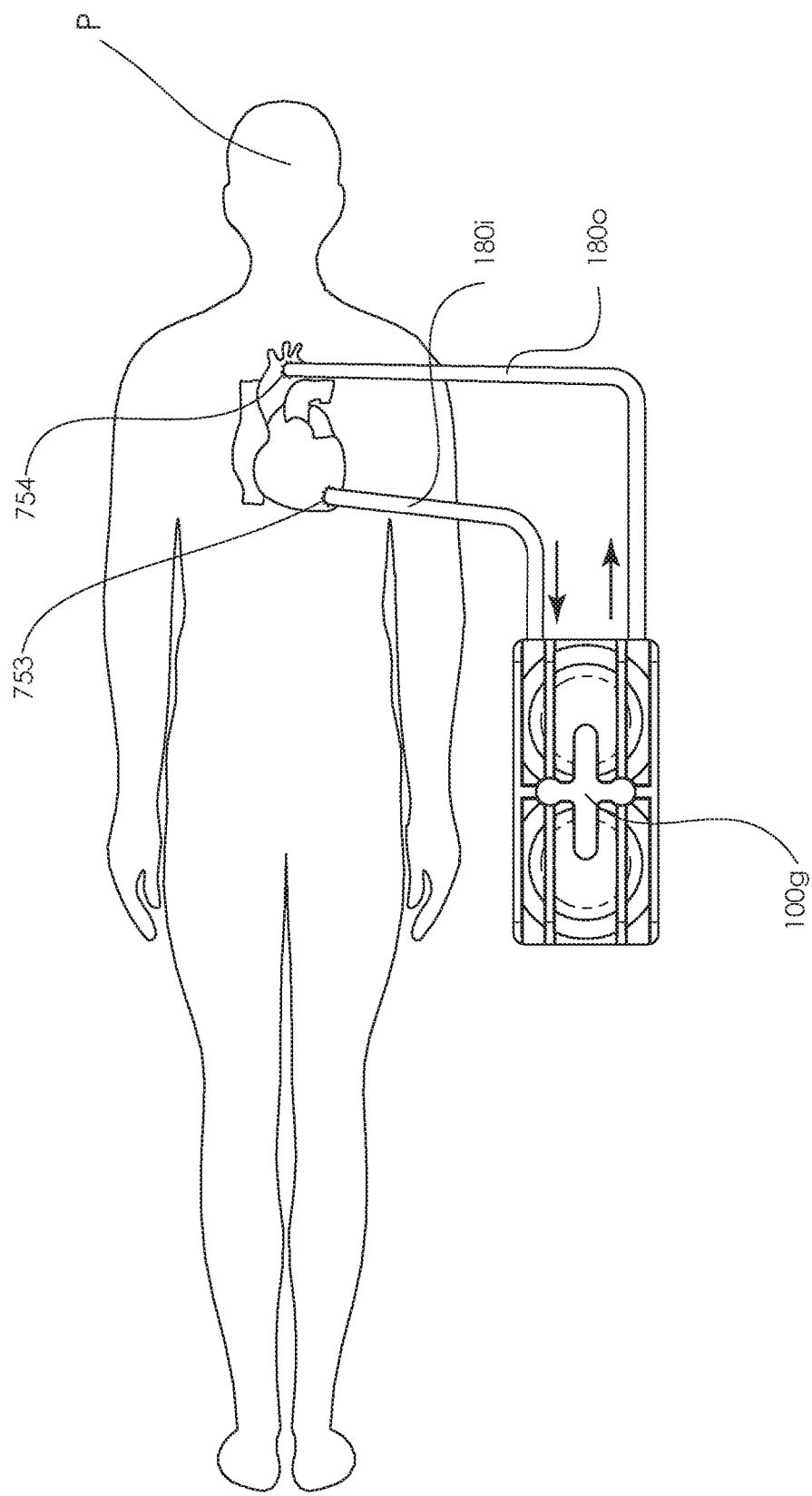
FIG. 18 is a schematic view of an embodiment of a heart-assist system using an embodiment of the double diaphragm pump.
Figure 19:
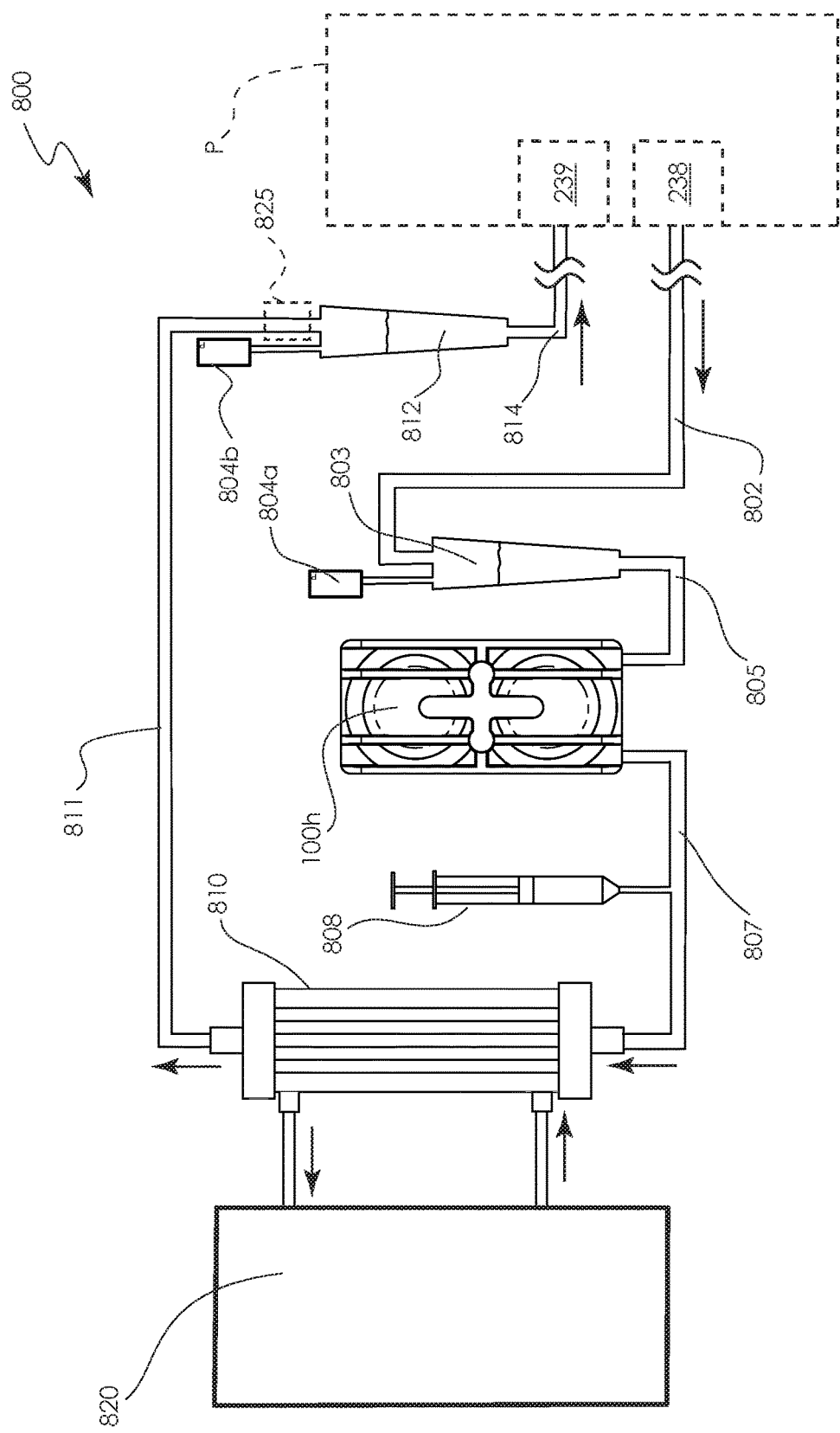
FIG. 19 is a schematic view of an embodiment of a hemodialysis system using an embodiment of the double diaphragm pump to effect flow through the system.

This disclosure relates to a pump apparatus and related methods and systems. Various views of an illustrative embodiment of a pump are provided in FIGS. 1-6B and 9A-11. FIGS. 7-8B relate to an embodiment of a forming fixture used to shape regions of a chamber diaphragm which can be used in a pump. An embodiment of pumping system utilizing a double diaphragm pump is shown in FIGS. 12-15. FIG. 16 provides a schematic view of an embodiment of a system utilizing a double diaphragm pump. The schematic views provided in FIGS. 17-19 illustrate various applications of embodiments of double diaphragm pumps in medical applications in which blood is pumped.

It is noted that similar or duplicate features are referred to with a unique alphanumeric designation. Certain features common to various embodiments may be designated with a primed numeral in some figures. In either case, duplicate elements will not be described in further detail to the extent their performance is similar to the embodiments previously described. For example, the chamber diaphragms illustrated in FIG. 2 will be referred to as 140a and 140b, and various diaphragm blood pumps are referred to in FIG. 17 as 100b, 100c, 100d, etc. A pump body in one embodiment is referred to in FIG. 9C as 110 and a pump body in another embodiment is referred to in FIG. 10 as 110'.

Certain diaphragm pumps can have application as a single use disposable medical blood pump. For example, a pump can be used to move blood through an extracorporeal circuit.

An advantage of pumping blood with certain pumps as described herein is that, in various embodiments, a relatively small amount, a minimal amount, a negligible amount, or even no amount of synthetic pump material particles is released into the flow of blood that is caused by rubbing, sliding, or straining of materials typically used in other types of pump mechanisms to energize fluid flow. Synthetic particulates generated by certain pumps that move fluids to and from a patient have the potential to create adverse health effects including embolisms or microembolisms in the vascular system. Further, the toxicity of materials introduced or generated by such pumps can be delivered to the patient and can be left residing in the vascular system of the patient.

Certain embodiments of a pneumatically actuated diaphragm pump can be advantageous because of the inherent control that may be achieved for delivering fluids within physiologically acceptable pressure ranges. For example, if a blockage occurs in the process fluid lines connected to an embodiment of a pump, some embodiments of the pump may only generate pressure in the process fluid at a level that is at or near those of the motive fluid pressures that are driving the pump. In the case of pumping blood, such a pump can reduce or eliminate excessive pressures or high vacuums in the fluid lines that can potentially damage blood or cause air embolisms by out-gassing the blood under high suction levels.

Some embodiments of pumping systems that may be used in single-use disposable medical applications can advantageously be comprised of a removable and/or separable disposable pumping component and a reusable pump control system. The disposable pumping component can be packaged and pre-sterilized for use in a medical application related to an individual patient. In some embodiments, the disposable pumping component can be coupled in operative association with the reusable pump control system for a single patient during a medical application, and then removed and disposed.

In some embodiments, the reusable pump control system can be isolated from the flow of biological fluids and may selectively control and operate a plurality of disposable pumping components-one or more for each of a multiple number of patients or applications, in some instances-without being sterilized between uses. The removable/disposable pumping component may include pump chambers, inlet and outlet valves, inlet and outlet lines, and other components which are in contact with the blood or biological fluid. In some embodiments, the removable/disposable pumping component comprises a double diaphragm pump. As discussed below, in some embodiments, the double diaphragm pump can be configured and designed with a plurality of pump chambers, flow paths, valves, etc. that are specifically designed for a particular application. For example, some embodiments of double diaphragm pumps can be configured for use in such medical applications as cardiopulmonary bypass, surgical perfusion support, heart assist, and hemodialysis, as further described below.

Various embodiments of double diaphragm pumps also enable fluids to be transferred in a wide variety of other fields. For example, such pumps can be used in the transfer of high purity process fluids. Some embodiments of double diaphragm pumps can be advantageous in transferring high purity process fluids, as the pump avoids, minimizes, or otherwise reduces the introduction or generation of contaminants or particulate matter that can be transferred downstream by reducing or eliminating rubbing and sliding components within the pump. Downstream transfer of contaminants or particulate matter may effect the desired outcome of using the high purity process fluid. Also for shear sensitive fluids, some pumps can be operated to gently move fluid from a source to a destination.

Figure 2:
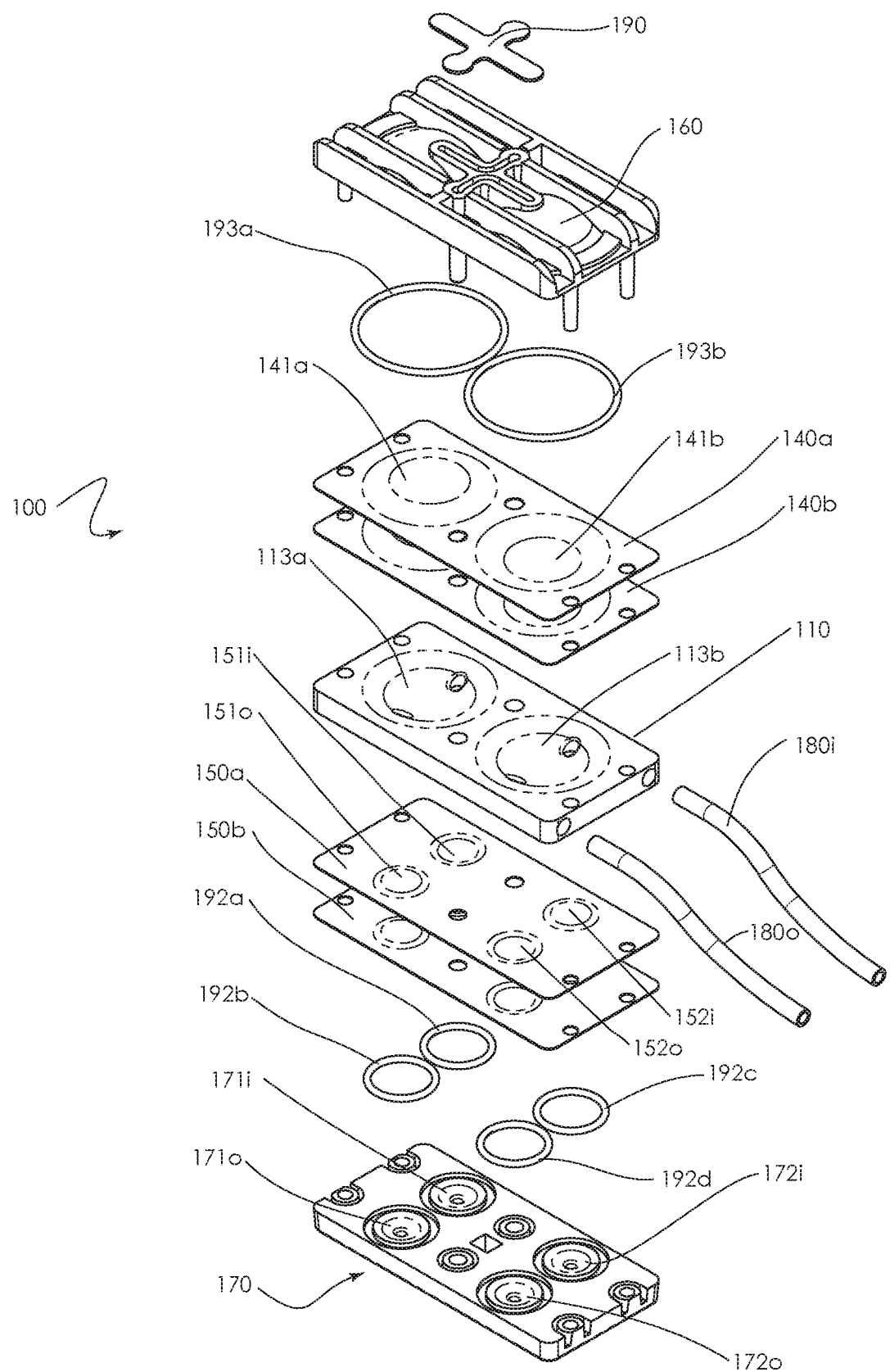
FIG. 2 is an exploded perspective view of the double diaphragm blood pump of FIG. 1.
Figure 9B:
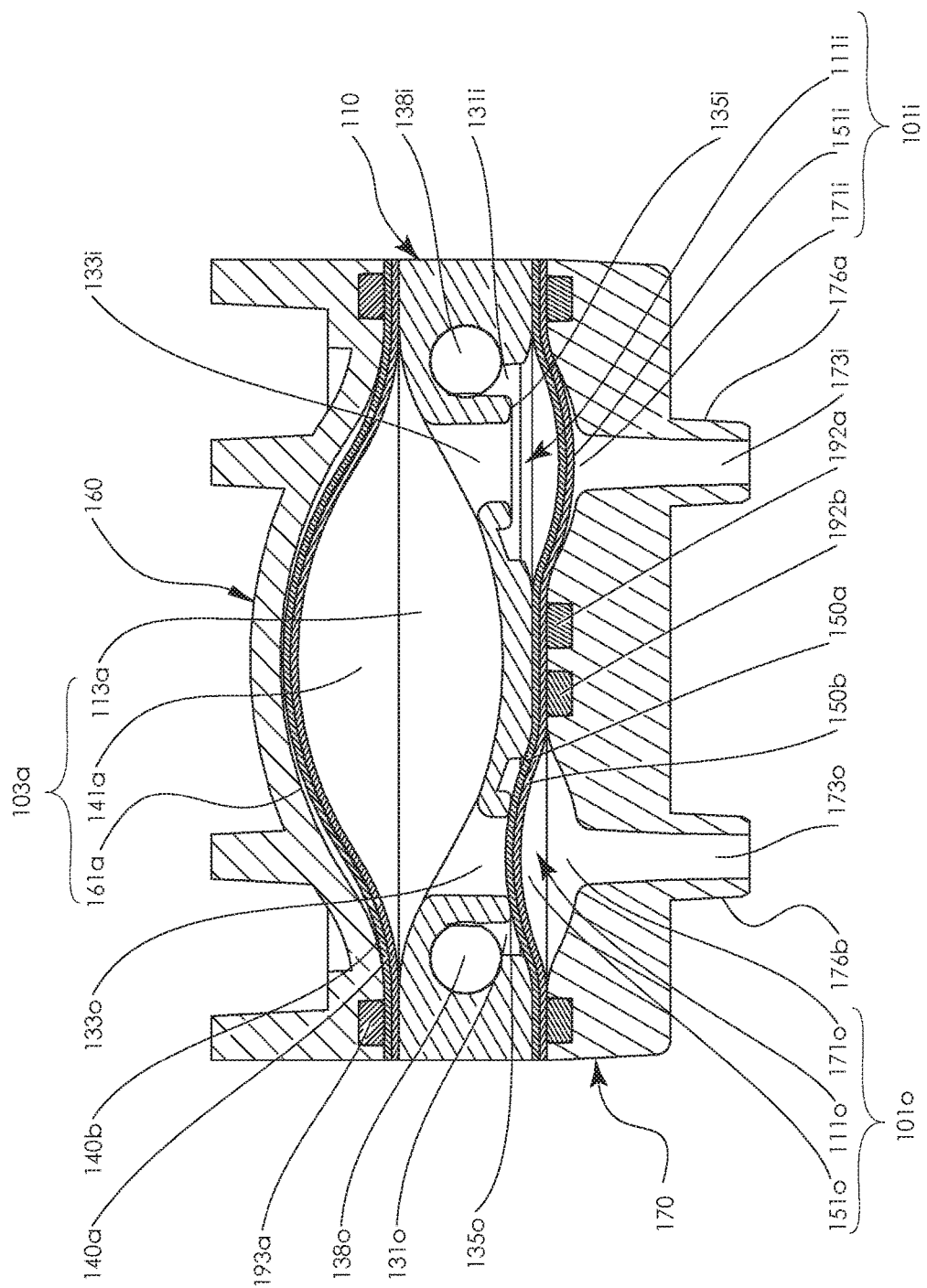
FIG. 9B is a cross-sectional view of the double diaphragm pump of FIG. 1 taken along cutting line 9B-9B in FIG. 9A.
Figure 9C:
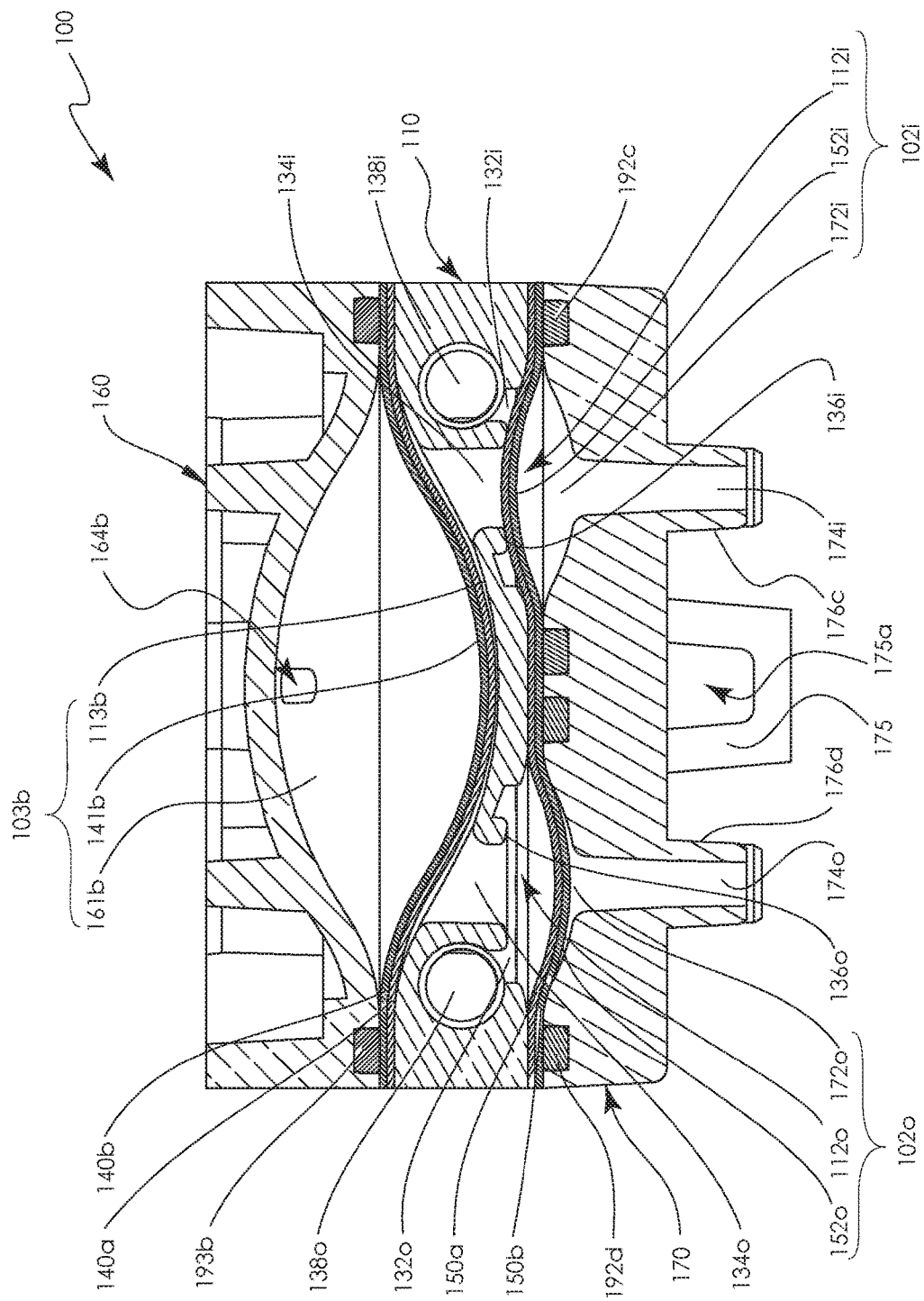
FIG. 9C is a cross-sectional view of the double diaphragm pump of FIG. 1 taken along cutting line 9C-9C in FIG. 9A.

FIG. 1 provides a perspective view of an embodiment of a double diaphragm pump at 100. The pump 100 can comprise a plurality of housing members or housing components, which in some embodiments may be substantially rigid, as discussed below. In some embodiments, the housing members comprise a pump body 110, a chamber plate 160 and a valve plate 170. In some embodiments, the pump 100 further comprises a plurality of diaphragms. For example, in some embodiments, the pump 100 comprises one or more chamber diaphragms 140a, 140b, which can be located between chamber plate 160 and pump body 110, and further comprises one or more valve diaphragms 150a, 150b, which can be located between valve plate 170 and pump body 110. The chamber diaphragms 140a, b and valve diaphragms 150a, b are not identified in FIG. 1 but are shown in FIGS. 2, 9B, and 9C. While these diaphragms may not necessarily extend to the perimeter of pump body 110, chamber plate 160, or valve plate 170, in some embodiments, the media can extend to the perimeter or beyond so that the media protrudes beyond an outer edge of the pump body 110. As further discussed below, in some embodiments, manifold cover plate 190 seals or closes motive fluid passages defined by chamber plate 160.

Figure 4:
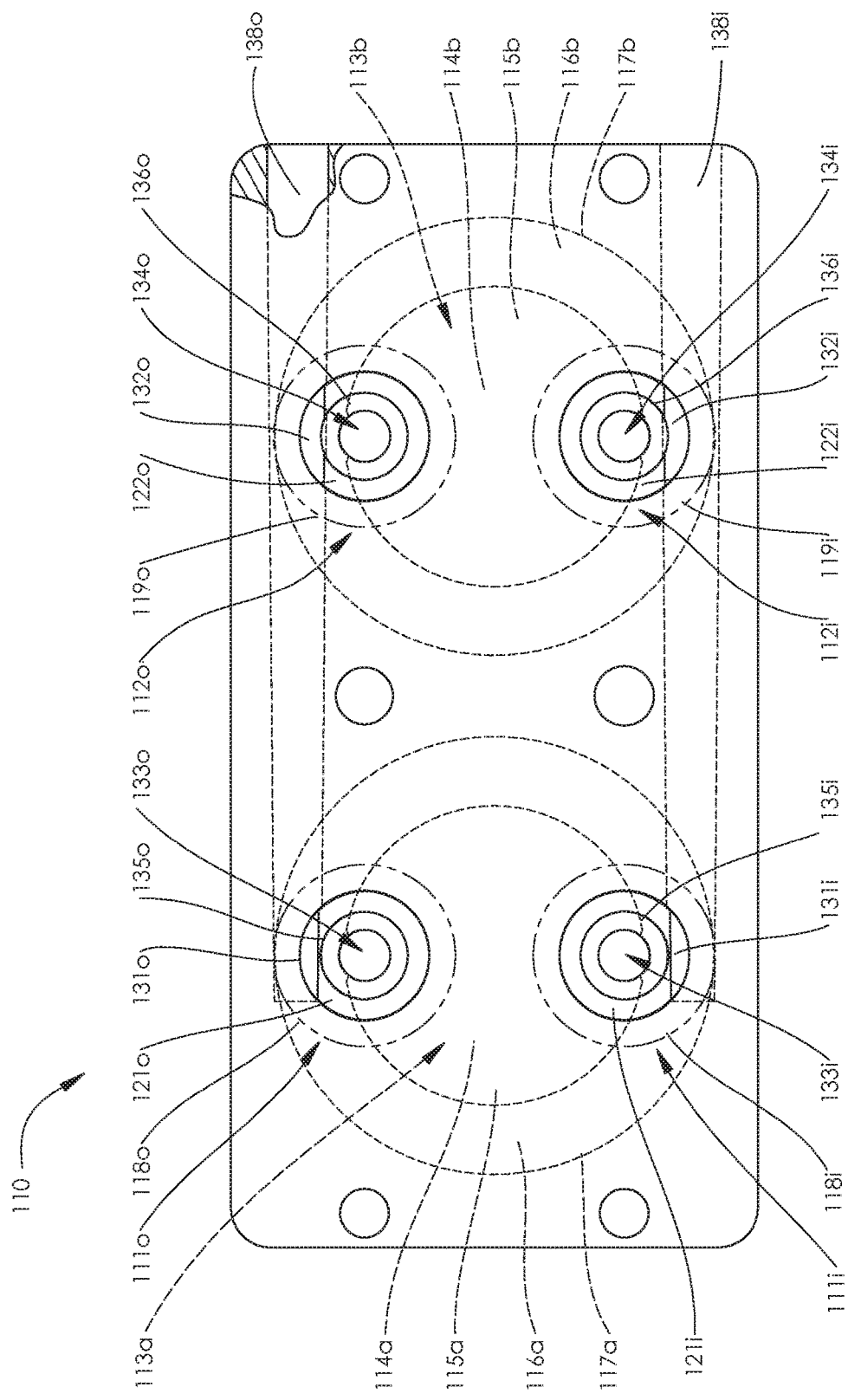
FIG. 4 is a plan view of one side of an embodiment of a pump body with a portion of the interior of the pump body shown in phantom and a portion of an opposite side of the pump body shown in phantom.

FIG. 1 and FIG. 4 show features related to the inlet and outlet lines for the passage of process fluid through the pump body 110. In particular, inlet line 180i is connected with inlet channel 138i and outlet line 180o is connected with outlet channel 138o, as shown. Inlet channel 138i and outlet channel 138o are shown in more detail in FIG. 4, FIGS. 9B-10 and FIG. 16. In the embodiment illustrated in FIGS. 1 and 4, representative connections between inlet line 180i and inlet channel 138i and between outlet line 180o and outlet channel 138o are shown. Similar connections can be made to other external fluid lines or devices. The connection between these components can include solvent bonding, adhesives, mechanical fittings (including barbed nipple tube fittings), or other methods well known in the art.

Figure 10:
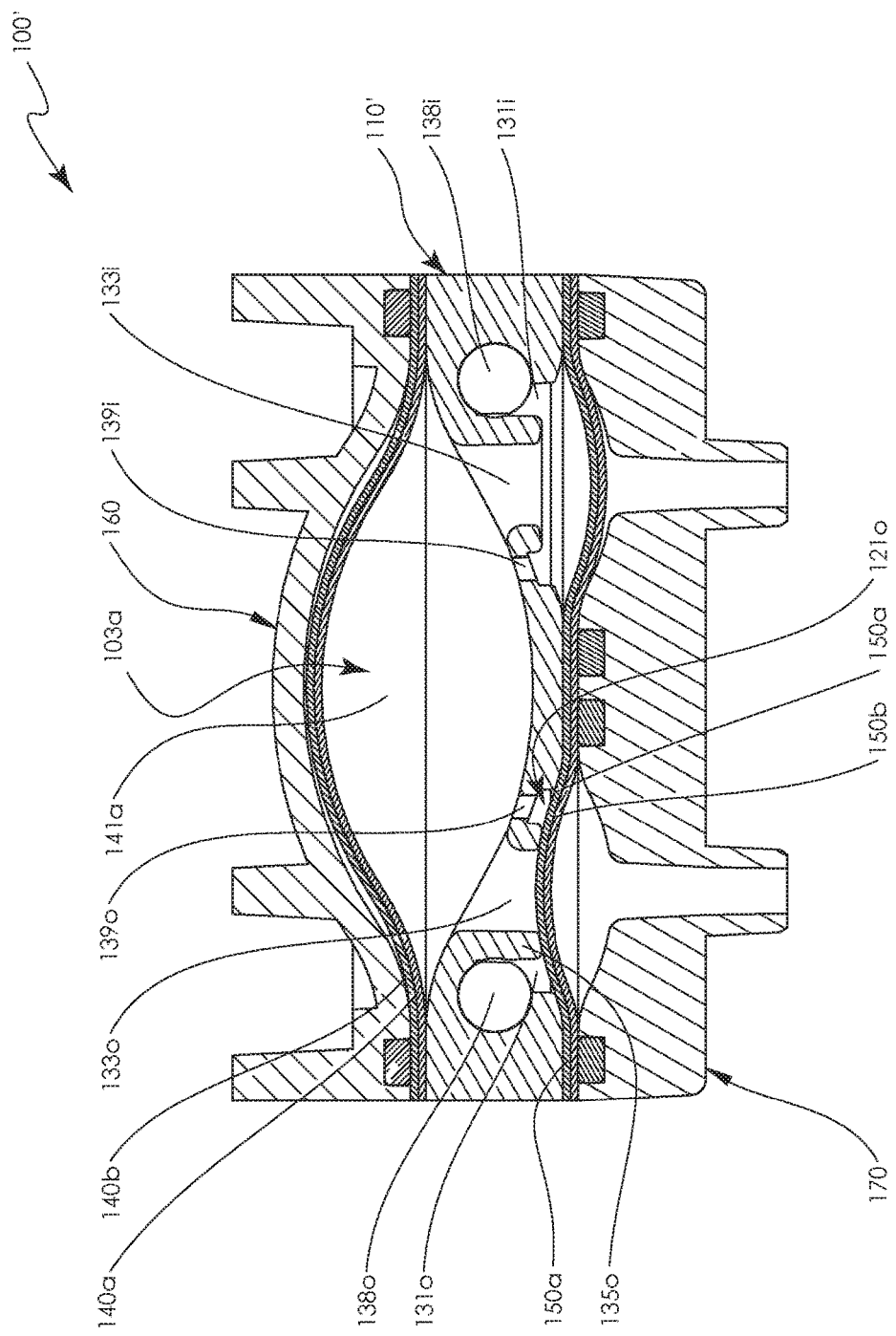
FIG. 10 is a cross-sectional view of another embodiment of the double diaphragm pump of FIG. 1 taken along cutting line 9B-9B in FIG. 9A showing valve bypass passages.

Some of the components which comprise the valves and the pump chambers are shown in FIG. 2, however, the valves and the pump chambers are not identified in FIG. 2, as this figure represents an exploded perspective view of a double diaphragm pump 100. As illustrated in FIGS. 9B-9C and FIG. 10, certain embodiments of the double diaphragm pump 100 can comprise a first inlet valve 101i, first outlet valve 101o, second inlet valve 102i, second outlet valve 102o, first pump chamber 103a, and second pump chamber 103b. FIG. 2 also shows a plurality of valve seals or o-rings 192a-d and chamber seals or o-rings 193a, b, which can be used in some embodiments to assist in sealing valves and pump chambers. For example, in some embodiments, the valve plate 170 comprises grooves 177i, 177o, 178i, and 178o (see FIG. 3) for receiving o-rings 192a-d. Similarly, chamber plate 160 can comprise grooves for receiving o-rings 193a, b.

Other means of sealing the valves and chambers can also be used, including adhesives, heat bonding, and welding. In certain embodiments, the diaphragms 140a, b and 150a, b and pump body 110 can be fabricated with similar materials that will bond together when heated. In some embodiments, fluorinated ethylene propylene (FEP) materials can be used for both of the diaphragms 140a, b, 150a, b and the pump body 110, and heat can be used to bond the diaphragms to the body. Other heat sealable materials that can be used for both of the diaphragms 140a, b, 150a, b and the pump body 110 include polyvinylchloride (PVC), polyurethane (PU), and polypropylene (PP). In some embodiments, an adhesive, such as Scotch Weld Acrylic DP-8005 adhesive manufactured by 3M-Industrial Business, Industrial Adhesives and Tapes Division, St. Paul, Minn., is used to attach the chamber plate 160 assembly posts 169a-d and air bosses 162a, b (see, e.g., FIG. 5) to the valve plate 170 assembly holes 179a-f (see, e.g., FIG. 3). Components of a double diaphragm pump 100, such as the components shown in FIG. 2 can be assembled together in any other suitable manner, such as via mechanical fasteners (for example nuts and bolts, clamps, screws, etc.); adhesives; welding; bonding; or other mechanisms. These mechanisms are all examples of means for maintaining the plates and body together and sealing chambers created between the plates and body.

FIG. 2 provides the best view of the chamber diaphragms 140a, b and valve diaphragms 150a, b. In the illustrated embodiment, each diaphragm 140a, b and 150a, b has a specific region corresponding with a particular chamber. In some embodiments, the regions are preformed or pre-shaped prior to assembly of the pump 100. In some embodiments, a single diaphragm is used between pump body 110 and chamber plate 160 and/or a single diaphragm is used between pump body 110 and valve plate 170. In other embodiments, two or more diaphragms are utilized between one or more sets of neighboring components, which can provide a pump 100 with one or more redundant layers for safety purposes. For example, in the unlikely event that one of the diaphragms were to fail due to a rare manufacturing defect, interaction with a sharp object in the air or fluid flow, cyclic fatigue cracking, or other cause of failure, the pump could safely operate using a redundant diaphragm. In some embodiments, each chamber or valve uses a separate diaphragm or diaphragms that are not integrated into a multi-chamber diaphragm. Additionally, the separate diaphragms can also include preformed or pre-shaped actuation regions. In some embodiments, the actuation regions are configured to move between a natural shape and an inversion of the natural shape without significant stretching, as further discussed below. The actuation regions can be configured to flex, in some embodiments. Methods for forming diaphragms with pre-shaped regions are discussed below with reference to FIGS. 6A, 6B, 7, 8A, and 8B.

In certain embodiments, the preformed actuation regions of chamber diaphragm 140a include first pump chamber region 141a and second pump chamber region 141b. The preformed actuation regions of valve diaphragm 150a include first inlet valve region 151i, first outlet valve region 151o, second inlet valve region 152i, and second outlet valve region 152o. Each media 140a, b and 150a, b can also have holes 142a-f (see FIG. 6A) for manufacturing and assembly, as further discussed below.

With reference to FIGS. 2, 9B, and 9C, first pump chamber 103a is divided by first pump chamber region 141a into first pump chamber cavity 113a and first actuation cavity 161a. Similarly, second pump chamber 103b is divided by second pump chamber region 141b into second pump chamber cavity 113b and second actuation cavity 161b. Each of the valves 101i, 101o, 102i, and 102o is also divided by its respective diaphragm regions. In particular, each of valves 101i, 101o, 102i and 102o comprises an actuation cavity and a valve seat. The valve seats include first inlet valve seat 111i, first outlet valve seat 111o, second inlet valve seat 112i, and second outlet valve seat 112o. The actuation cavities include actuation cavity 171i of first inlet valve 101i, actuation cavity 171o of first outlet valve 101o, actuation cavity 172i of second inlet valve 102i and actuation cavity 172o of second outlet valve 102o. Together, a given valve seat/actuation cavity pair can define a valve chamber through which a diaphragm region can move. For example, with reference to FIG. 9B, the first outlet valve region 151o can move within a valve chamber that is comprised of the first outlet valve seat 111o and the actuation cavity 171o.

The flow paths of the process fluid in some embodiments of the double diaphragm pump 100 are described below with reference to FIG. 4 and FIG. 16. The flow path is also described with reference to FIGS. 9A-10. Before providing a comprehensive overview of the flow path, the components of double diaphragm pump 100 are described below with occasional reference to the flow path. However, it should be understood that a process fluid is pumped into and out of first pump chamber 103a and second pump chamber 103b so that the process fluid enters and exits pump body 110. It should also be understood that the different regions of the diaphragm media are moved by alternating applications of pressure and vacuum to the pump chambers and valves to pump the process fluid into and out of pump chambers 103a and 103b and allow or prevent flow through valves 101i, 101o, 102i, and 102o. The pressure and vacuum can be provided by one or more fluids (also referred to as motive fluids) at differing pressure levels. In many embodiments, the motive fluids used with a pump 100 comprise air. Accordingly, reference throughout this disclosure may be made to "air" when describing the movement of motive fluid or when describing components associated with and/or that contact motive fluid during operation of a pump 100. Such references are not intended to be limiting, but rather, are made only to facilitate the discussion herein. For any such reference, other suitable fluids are also possible, such as, for example one or more liquids and/or gases.

In certain embodiments, different regions of the chamber diaphragms 140a and 140b and valve diaphragms 150a and 150b can be moved by applying pressure of the motive fluid which is greater than the pressure of the process fluid at the process fluid destination, receiver, or return 239 (see FIG. 16) and alternating with application of pressure of the motive fluid which is less than the pressure of the process fluid at the process fluid source 238 (see FIG. 16).

The amount of pressure or vacuum applied can vary significantly depending on the intended use of the pump 100. For example, in some embodiments, the double diaphragm pump 100 delivers a fluid at a pressure in a range of between about 0 mmHg (millimeters of mercury) and about 1500 mmHg, between about 50 mmHg and about 500 mmHg, between about 50 mmHg and about 700 mmHg, or between about 80 mmHg and about 500 mmHg. Similarly, in some embodiments, the double diaphragm pump 100 may receive fluid from a source or generate suction in a range of between about −500 mmHg and about 0 mmHg, between about −250 mmHg and about 0 mmHg, between about −120 mmHg and about 0 mmHg, or at an amount that is less than the fluid pressure at the process fluid source 238.

In some embodiments of the double diaphragm pump 100 that are configured to be used as a blood pump, blood is received into the pump and delivered from the pump in a range between about −250 mmHg and about 500 mmHg. While blood pressure in a patient vasculature system is typically in a range of 0 mmHg to 200 mmHg, depending on the location of blood in the system and condition of the patient, the blood pump 100 may operate at higher pressures and with vacuum assisted suction to overcome pressure losses in the extracorporeal circuit. These pressure losses can occur as blood flows through cannulae, connection lines, blood treatment devices, filters, reservoirs, and connectors. The blood pump may be operated to cause the blood to be drawn from and return to the patient vascular system at safe levels. These safe levels of blood pressure at the fluid source 238 may be above 0 mmHg and the blood pressure at the fluid return 239 may be below 150 mmHg. The blood may also be drawn into the pump without a vacuum source supplied to the pump (e.g., by application of about O mmHg relative pressure via a vacuum source or vent 230). Gravity feed into the pump may also be used to assist in filling the pump chambers. For example, in some embodiments, the process fluid source 238 is at an elevated pressure and at an elevated location from the pump and the resultant blood pressure at the pump causes the pump valves and chambers to vent the motive fluid and actuate the diaphragms when the pressure source 220 is removed (e.g., about 20 mmHg relative to atmosphere and located 24 inches higher in elevation). A motive fluid at a pressure higher than the elevated pressure of the blood entering the pump and also higher than the pressure at the fluid return 239 can be used to operate the pump and expel the process fluid from the pump 100 to deliver blood through an external circuit to the process fluid return 239 at acceptable physiological pressures (e.g., in some cases at about an average pressure of 80 mmHg).

Figure 3:
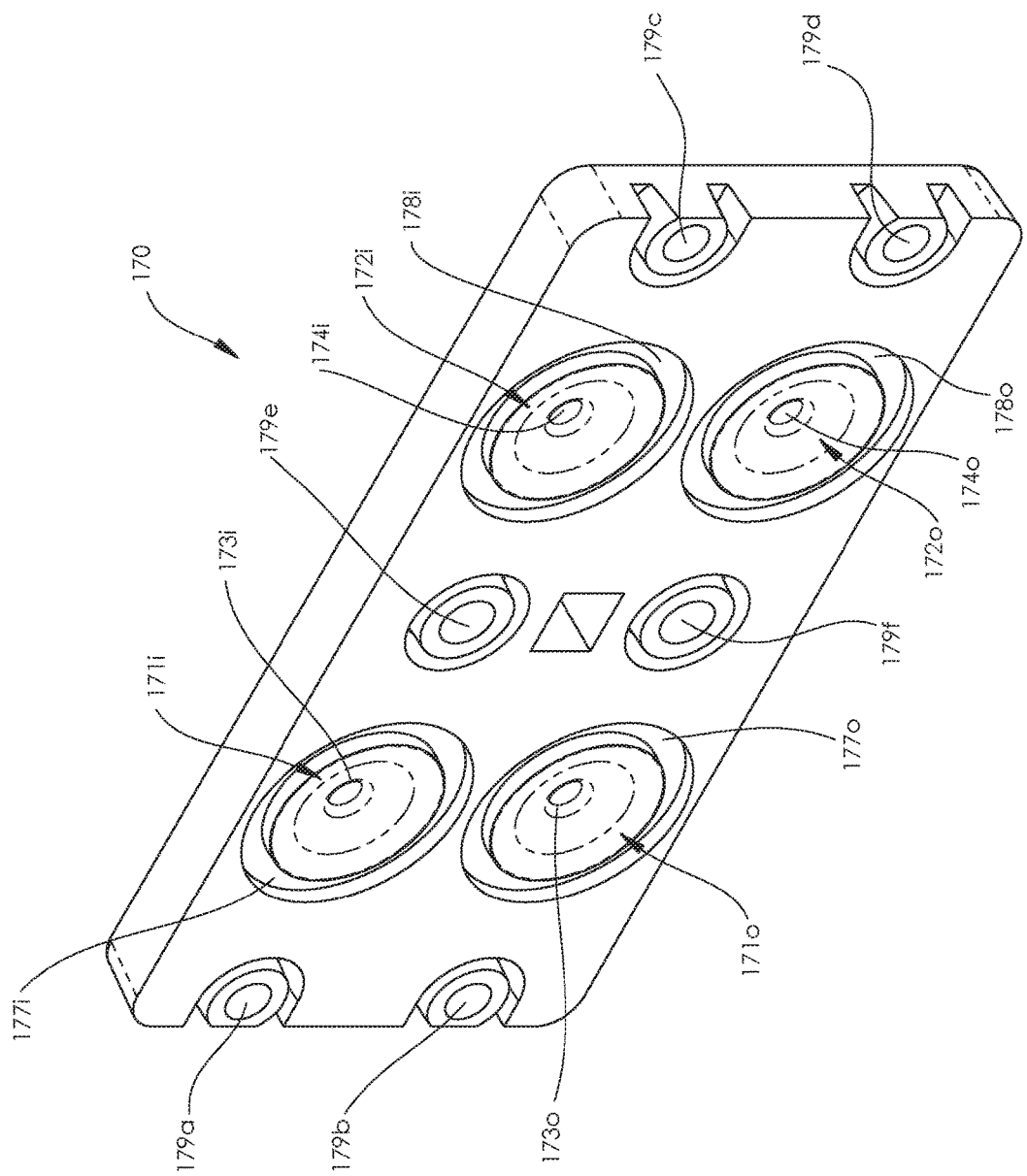
FIG. 3 is a perspective view of an inner side of an embodiment of a valve plate.

FIG. 3 and FIGS. 9B-9C show actuation cavity 171$i$ of first inlet valve 102$i$, actuation cavity 171$o$ of first outlet valve 102$o$, actuation cavity 172$i$ of second inlet valve 102$i$, and actuation cavity 172$o$ of second outlet valve 102$o$. Passages 173$i$, 173$o$, 174$i$, and 174$o$ provide fluid communication to the actuation cavities through the air transfer bosses 176$a$-$d$. The air transfer bosses 176$a$-$d$ may also be referred to as connections, connectors, posts, protrusions, interfaces, passageways. These terms can also be used to describe other bosses described herein.

Figure 5:
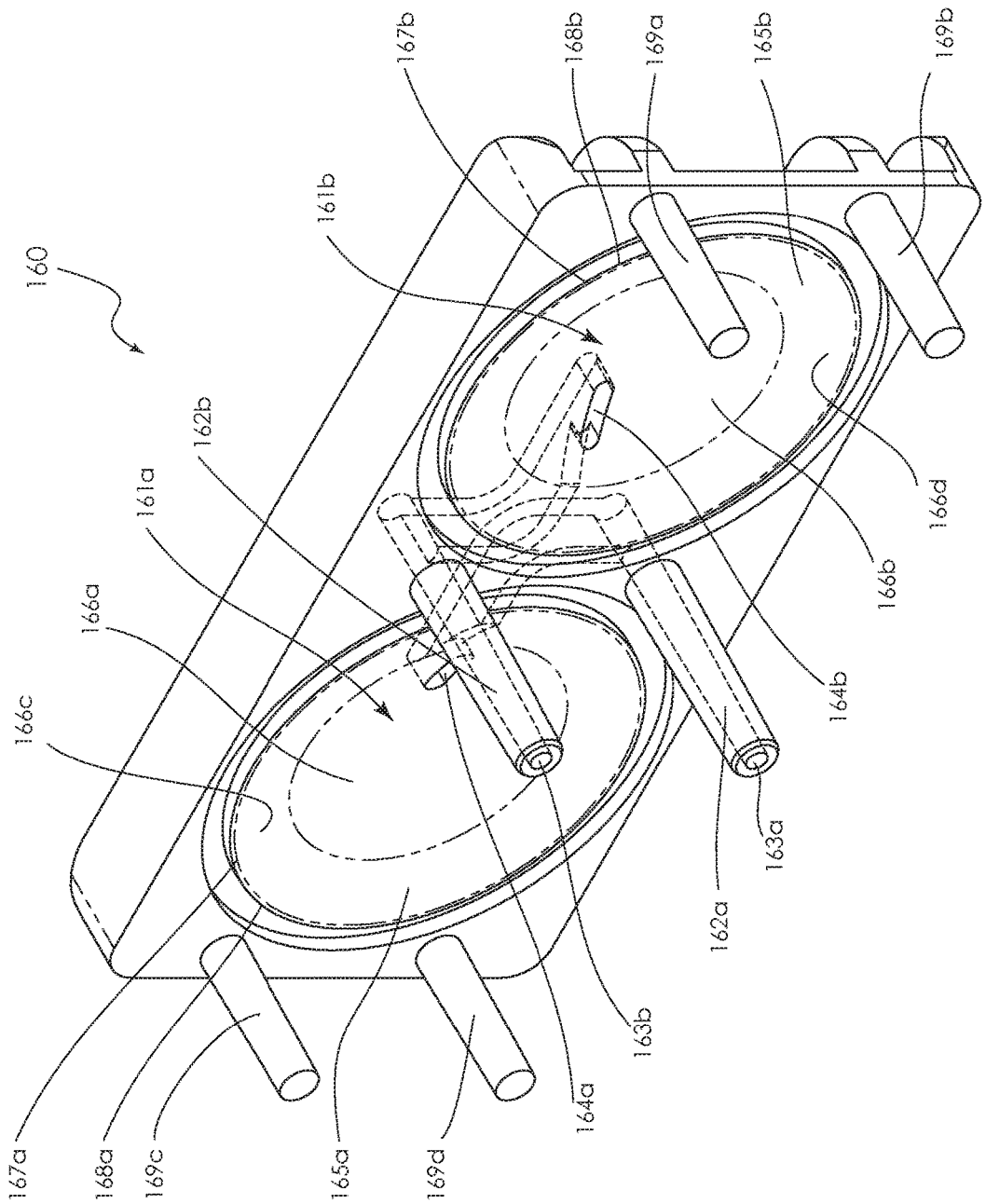
FIG. 5 is a perspective view of the inner side of an embodiment of a chamber plate with interior features thereof shown in phantom.

FIG. 5 shows the chamber plate 160, which can include first chamber actuation cavity 161$a$ and second chamber actuation cavity 161$b$. The chamber plate 160 can include passages 163$a$ and 163$b$. As shown, for example, in FIG. 1, the manifold plate 190 can be sealed over passages 163$a$ and 163$b$. With reference again to FIG. 5, passage 163$a$ provides fluid communication to actuation cavity 161$a$ via opening 164$a$, and passage 163$b$ provides fluid communication to actuation cavity 161$b$ via opening 164$b$.

In certain embodiments, actuation cavities 161$a$, $b$ are defined by cavity surfaces 165$a$, $b$ that extend to outer perimeters 168$a$, $b$, respectively. The cavity surfaces 165$a$, $b$ can include recesses 166$a$, $b$, respectively. An edge of each recess 166$a$, $b$ is shown with dashed lines in the embodiment illustrated in FIG. 5. In some embodiments, one or more of the recesses 166$a$, $b$ are substantially rounded, and may be concavely rounded. The cavity surfaces 165$a$, $b$ can include inclined regions 166$c$, $d$ that extend from the recesses 166$a$, $b$ and outer rims 167$a$, $b$ of the actuation cavities 161$a$, $b$, respectively. In some embodiments, the inclined regions 166$c$, $d$ are also rounded, and may be convexly rounded. In some embodiments, rounded recesses 166$a$, $b$ and rounded inclined regions 166$c$, $d$ can limit the mechanical strain and increase cyclic life induced by limiting the minimum radius of bending curvature of the integrated diaphragm media 140$a$, $b$ in the diaphragm actuation region 141$a$, $b$ between the constrained edge of the diaphragm actuation region and a slope inflection point of the diaphragm actuation region as the diaphragm actuation region 141$a$, $b$ transitions between end-of-stoke positions.

FIG. 4 shows a plan view of a first face or a first side of pump body 110, and illustrates first inlet valve seat 111$i$, first outlet valve seat 111$o$, second inlet valve seat 112$i$ and second outlet valve seat 112$o$. First pump chamber cavity 113$a$ and second pump chamber cavity 113$b$, which are located on the opposite face or side of pump body 110, are shown in phantom. Each valve seat has a groove 121$i$, 121$o$, 122$i$, 122$o$ around a corresponding rim 135$i$, 135$o$, 136$i$, 136$o$. A valve portal 131$i$, 131$o$, 132$i$, 132$o$ provides fluid communication between each valve seat and its corresponding line. For example, inlet channel 138$i$, which is shown in phantom, is in fluid communication with first inlet valve portal 131$i$ and second inlet valve portal 132$i$. Similarly, outlet channel 138$o$, which is also partially shown in phantom and partially shown in the broken section view, is in fluid communication with first outlet valve portal 131$o$ and second outlet valve portal 132$o$.

Chamber passages or channels 133$i$ and 133$o$ provide fluid communication respectively between first inlet valve seat 111$i$ and first pump chamber cavity 113$a$ and between first outlet valve seat 111$o$ and first pump chamber cavity 113$a$ Similarly fluid communication between second inlet valve seat 112$i$ and second pump chamber cavity 113$b$ and between second outlet valve seat 112$o$ and second pump chamber cavity 113$b$ is achieved, respectively, via chamber channels 134$i$ and 134$o$. This configuration permits first inlet valve seat 111$i$ and second inlet valve seat 112$i$ to be in fluid communication with inlet channel 138$i$ and to alternatively receive process fluid. Similarly, first outlet valve seat 111$o$ and second outlet valve seat 112$o$ are in fluid communication with outlet channel 138$o$ and alternatively deliver process fluid.

FIG. 4 also shows other features of the pump chamber cavities 113$a$ and 113$b$. Surfaces of each pump chamber cavity, which can be recessed surfaces, are identified respectively at 114$a$ and 114$b$ with an inclined region for each identified at 115$a$ and 115$b$, respectively. A rim 116$a$, $b$ and a perimeter 117$a$, $b$ are also identified for each of the pump chamber cavities 113$a$, $b$, respectively. The perimeters of the valve seats are also shown in FIG. 4. The perimeter of first inlet valve seat 111$i$ and the first outlet valve seat 111$o$ are respectively shown in phantom and identified as 118$i$ and 118$o$. The perimeter of second inlet valve seat 112$i$ and the second outlet valve seat 112$o$ are respectively identified at 119$i$ and 119$o$.

With continued reference to FIG. 4 and, additionally, with reference to FIGS. 9B and 9C, in certain embodiments, the pump chamber cavities 113$a$, $b$ can define a smooth transition from a face of the pump body 110 to the recessed surfaces 114$a$, $b$. For example, in some embodiments, the perimeters 117$a$, $b$ of the pump chamber cavities 113$a$, $b$ are located at a substantially planar face of the pump body 110. The rims 116$a$, $b$ can be substantially rounded, and can provide a smooth transition from the planar face at the perimeters 117$a$, $b$ to the inclined regions 115$a$, $b$.

Similarly, the valve seats 111$i$, 111$o$, 112$i$, 112$o$ can define a smooth transition from a face of the pump body 110 to a more recessed portion of the pump body 110. For example, the valve seat 111$i$ can smoothly slope inward from the perimeter 118$i$, which can be at a substantially planar first face of the pump body 110, toward a more recessed portion of the valve seat 111$i$ that is closer to an opposite face of the pump body 110.

In certain embodiments, smooth, tangent, or rounded transitions such as just described can limit the mechanical strain by limiting the minimum radius of bending curvature of the diaphragm actuation region between the constrained perimeter of the diaphragm and a slope inflection point in the diaphragm as the diaphragm actuation region transitions between end-of-stoke positions. Reduced mechanical strain can result in a longer lifespan of the chamber diaphragms 140a, b and valve diaphragms 150a, b, in certain embodiments. In some embodiments, the diaphragms are constrained to flex at the smooth or rounded transitions (e.g., to flex over the rounded lips 116a, b). In some embodiments, the amount of strain induced in a flexing diaphragm is inversely related to the radius of curvature in these regions; as a result, longer mechanical life of the diaphragms can be achieved with relatively gradually sloping transition regions. In other embodiments, relatively sharp transitions in these regions can cause the diaphragm to flex across a plastic-like hinge. A diaphragm actuation region could incur high cyclic strain in certain of such embodiments, and might rapidly fail due to cyclic fatigue.

The valve diaphragms 150a, 150b can have additional support as the diaphragms rest on seat rims 135i, 135o, 136i, and 136o in a closed valve position, which can be at a position near a preformed dome height of the valve diaphragm valve regions 151i, 151o, 152i, 152o. If the diaphragm material is too stretchable or if the diaphragm valve regions 151i, 151o, 152i, 152o are formed with excessive dome heights, high strain plastic-like hinges can form on the edges of the seat rims, and may cause high cyclic strain and short cyclic fatigue life. In some embodiments, the diaphragm valves desirably actuate from an open to a closed position at a differential pressure less than that provided by the pressure source 220 and at a differential pressure level less (e.g., less negative) than that provided by the vacuum source 230 (see FIG. 16). This can allow the valves to quickly open and close prior to the pump chamber causing a substantial amount of process fluid to flow back through the closing valves.

In some embodiments, chamber diaphragms 140a, b and valve diaphragms 150a, b have actuation regions, which are pre-shaped or formed prior to assembly of the pump 100, as further discussed below. The actuation regions can protrude from a plane defined by a relatively flat portion of a diaphragm 140a, b, in some embodiments. In further embodiments, the actuation regions naturally protrude and/or are naturally rounded in a convex manner when in a first state or resting state, and can be transitioned to a concave orientation when in a second state or displaced state. The second state can be stable or metastable, in some embodiments, and the actuation regions can define a variety of other shapes in the first and/or the second states. In some embodiments, the actuation regions can be readily transitioned between the first and second states, and the regions can deform, flex, or otherwise change shape by application of a relatively small amount of pressure, as compared with a substantially flat diaphragm without actuation regions which is stretched to conform to the same shape of the first or second state of an actuation region.

Figure 6B:
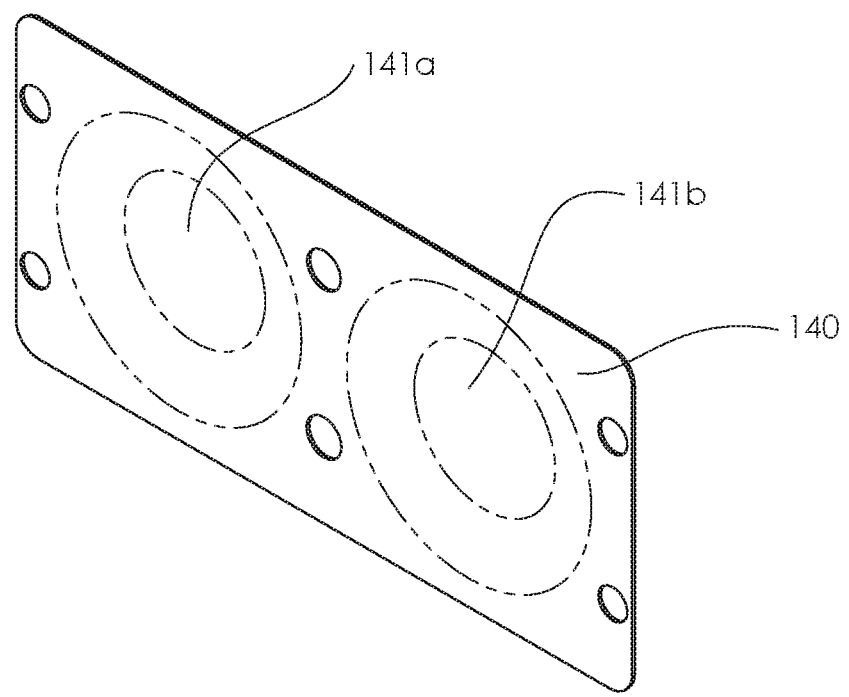
FIG. 6B is a perspective view of the diaphragm media of FIG. 6A after the regions have been formed.
Figure 7:
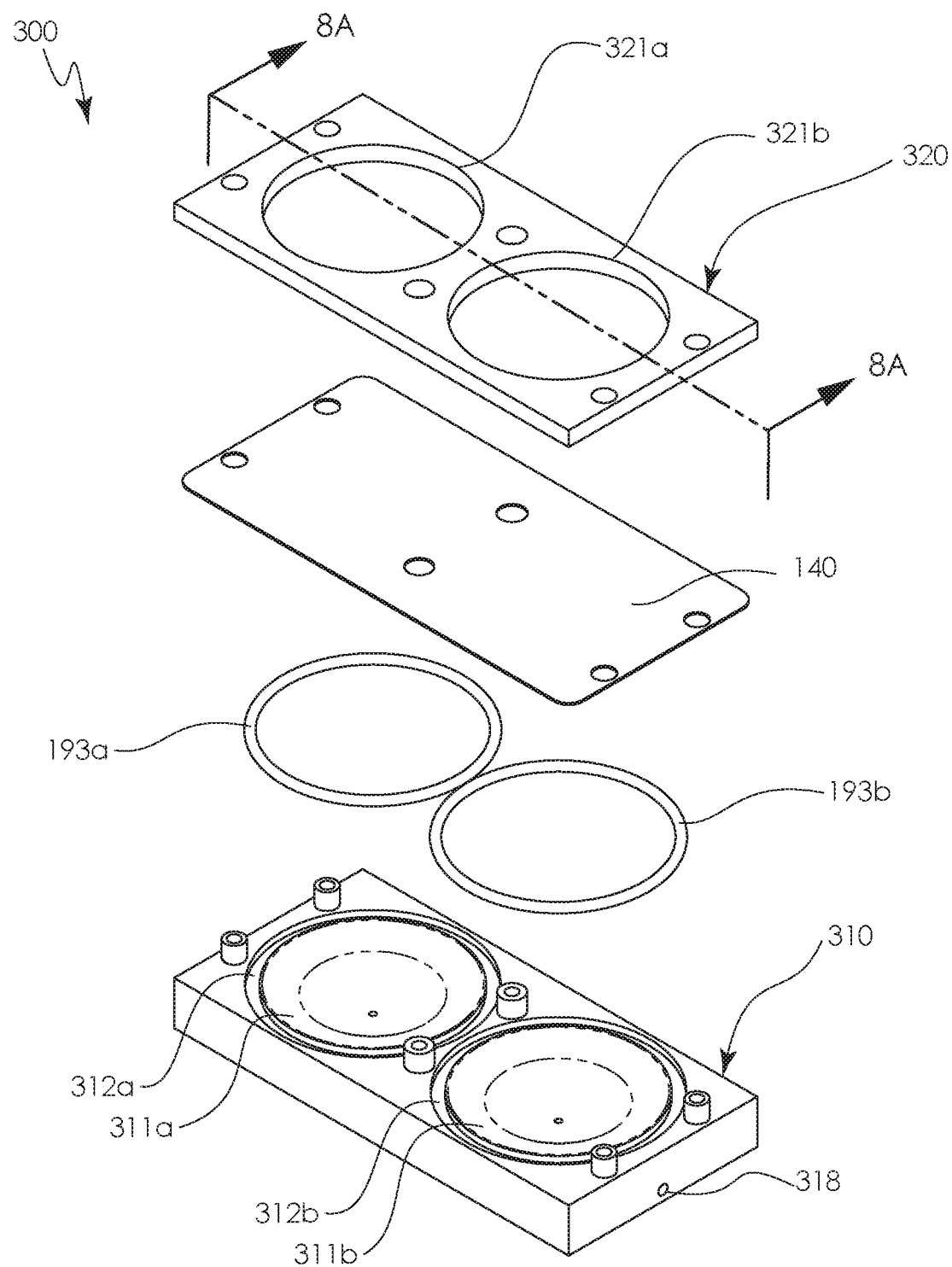
FIG. 7 is an exploded perspective view of an embodiment of a forming fixture used to form the regions in the diaphragm.

FIG. 6B depicts chamber diaphragm 140a after the formation of first pump chamber region 141a and second pump chamber region 141b. Preforming the chamber regions 141a, b of the chamber diaphragms 150a, b and the valve regions 151i, 151o, 152i, 152o of the valve diaphragms 140a, b can enable the valve regions to be seated and the chamber regions to move fluid into and out of the chambers based only on sufficient pressure (positive or negative) for movement of the regions, in some arrangements. Stated otherwise, after these regions of the diaphragm film material have been formed by, for example, heat forming or stretching, the regions can move in response to fluid pressure with low strain as each valve or chamber cycles like a fluid isolating membrane.

In some embodiments, the diaphragm regions are preformed in such a manner that the cord length of the valve regions and the chamber regions remains substantially constant while cycling. In other embodiments, the diaphragm regions stretch by a relatively small amount. One method to quantify diaphragm stretch is the change in cord length as the diaphragm flexes from end-of-stroke positions, where the cord length is the length of a cord if positioned on the surface of the diaphragm such that the cord extends from one point on the perimeter of the formed region and continues through the center point of the region to a second point on the perimeter of the formed region, with the first and second points being opposite from each other relative to the center point. For example, in various embodiments, the cord length can change by less than about 10%, less than about 5%, or less than about 3% during each pump cycle. The cord length can be sufficient to enable the diaphragm regions 150a, b and 151i, 151o, 152i, 152o to flex and pump the fluid in the pump chamber and to flex and controllably seal the fluid flow through the pump valves at the same or substantially the same pressures. By preforming the regions of the diaphragm media in some embodiments, the valve regions can be seated without application of additional pressure, as compared with the pressure used to move the region of the diaphragm within the pump chamber. By controlling the cord length of a diaphragm in certain embodiments, the mechanical cycle life of the diaphragm can be increased by minimizing material strain when flexing from one end-of-stroke condition to the other end-of-stroke condition, and the diaphragm can be capable of reaching the end-of-stroke condition without (or substantially without) the material of the diaphragm stretching. In certain embodiments, since pressure is applied for movement or is applied for movement and at most a nominal amount for stretching the preformed actuation regions, the amount of pressure needed to actuate the diaphragm region is low and the lifespan of the diaphragm media is extended due to the gentler cycling. In some embodiments, since material strain is reduced using thin film materials in the construction of the flexing chamber diaphragms 140a, b and valve diaphragms 150a, b, the material strain caused by in-plane stretching can be controlled by the support of the pump chamber and valve cavities at end-of-stroke conditions, and long mechanical life of the diaphragms can be achieved.

In certain embodiments, higher ratios of the maximum distance between opposing sides of a perimeter or perimeter width (e.g., the diameter of a circumference) of a diaphragm region 141a, b, 151i, 151o, 152i, 152o to a dome height of the region can promote long mechanical cyclic life of the diaphragms 140a, b, 150a, b without material fatigue failure. In some embodiments, the dome height of a region is defined as the maximum distance from a plane defined by a maximum perimeter of the region (e.g., a maximum circumference of the region) to any portion of the diaphragm material that comprises the region along a line normal to the plane. The term "dome height" is a broad term and is not limited to situations in which an actuation region 141a, b, 151i, 151o, 152i, 152o shaped substantially as a rounded dome. For example, a region having a substantially pyramidal configuration could also define a dome height.

In some embodiments, the diaphragm media is reshaped when traveling between end-of-stroke positions and the reshaping can cause the material to strain. With relatively low ratios between the perimeter width and the dome height of a region, the diaphragm material in some embodiments creates relatively sharp folds in order for the dome to move from one end-of-stroke condition to another which can cause relatively high material strain and a relatively short mechanical life for the diaphragm. With relatively high ratios between the perimeter width and the dome height of a region, the size of some embodiments of the double diaphragm pump 100 can be relatively large, which can increase material costs and other costs for manufacturing the pump 100.

In various embodiments, the ratio of the perimeter width to the dome height of the actuation regions 141*a, b* of the chamber diaphragms 140*a, b* is between 4:1 and about 30:1, between about 5:1 and about 20:1, or between about 6:1 and about 10:1. In some embodiments, the ratio is about 8:1. In certain of such embodiments, the actuation regions 141*a, b* have diameters of about 2.7 inches and dome heights of about 0.36 inches. For such embodiments, the actuation regions 141*a, b* can have a stroke volume of about 25 cubic centimeters (cc) when the dome moves from one end-of-stroke position to the other.

In various embodiments, the ratio of the diameter to the preformed dome height of the actuation cavities 171*i*, 171*o*, 172*i*, 172*o* of the valve diaphragms 150*a*, 150*b* is between about 4:1 and about 30:1, between about 5:1 and about 20:1, or between about 6:1 and about 10:1. In some embodiments, the ratio is about 8:1. In certain of such embodiments, the actuation cavities 171*i*, 171*o*, 172*i*, 172*o* have diameters of about 1.12 inches and dome heights of around 0.14 inches. For such embodiments, the actuation cavities 171*i*, 171*o*, 172*i*, 172*o* can have a valve actuation stroke volume of about 1.5 cubic centimeters (cc) when the dome moves from one end-of-stroke position to the other.

In certain embodiments, to actuate the chamber diaphragms 140*a, b* and valve diaphragms 150*a, b* from one end-of-stroke position to another, a certain pressure differential level between the fluid on one side of a diaphragm and the actuation chamber pressure on the other side of the diaphragm is provided to overcome the structural stiffness of the diaphragms. If the structural stiffness of the diaphragms is too high, the pressure used to actuate the regions 141*a, b*, 151*i*, 151*o*, 152*i*, 152*o* may exceed the desired operating pressure of the pump. However, some embodiments also benefit from the structural stiffness of the diaphragms not being too low. For example, in some embodiments, the diaphragms desirably have enough structural rigidity to not plastically deform under the operating pressures and also to bridge over regions of the diaphragms that are not supported at their end-of-stoke positions.

In various embodiments, the differential pressure used to actuate the chamber diaphragms 140*a*, 140*b* and valve diaphragms 150*a*, 150*b* is in a range of between about 5 mmHg and about 200 mmHg, between about 20 mmHg and about 100 mmHg, or between about 30 mmHg and about 60 mmHg. In some embodiments, a relatively small initial pressure differential is sufficient to actuate preformed regions 141*a, b*, from a first end-of-stroke position to a second end-of-stroke position. In some embodiments, a relatively small initial pressure differential is sufficient to actuate preformed regions 151*i*, 151*o*, 152*i*, 152*o* from an open valve position to a closed valve position.

Once a valve is in the closed position, the valve can remain in the closed position so long as the fluid pressure that acts on one side of the associated region to maintain the valve in the closed position exceeds the fluid pressure on the opposite side of the region by an amount greater than the amount of pressure required to actuate the valve. For example, in some embodiments, the region 151*o* can be actuated from the closed valve position illustrated in FIG. 98 to an open valve position when the pressure in the first chamber cavity 113*a* exceeds the pressure in the actuation cavity 171*o* by an amount greater than the pressure required to move the region 151*o* out of the closed orientation. In various embodiments, a valve can be maintained in the closed position when a differential pressure on opposite sides of a diaphragm actuation region is less than about 300 mmHg, less than about 200 mmHg, less than about 100 mmHg, less than about 50 mmHg, less than about 25 mmHg, less than about 10 mmHg, less than about 10 mmHg, or is about 0 mmHg. Similarly, in various embodiments, a valve can be maintained in the open position when a differential pressure on opposite sides of a diaphragm actuation region is less than about 300 mmHg, less than about 200 mmHg, less than about 100 mmHg, less than about 50 mmHg, less than about 25 mmHg, less than about 10 mmHg, less than about 10 mmHg, or is about 0 mmHg.

Some embodiments can include diaphragms 140*a, b*, 150*a, b* that comprise elastomeric material in a flat sheet configuration. Certain of such embodiments, however, can exhibit performance characteristics that are not present or are much less pronounced in some embodiments that include diaphragms 140*a, b*, 150*a, b* having actuation regions 141*a, b*, 151*i*, 151*o*, 152*i*, 152*o*. For example, in some embodiments having a flat sheet configuration, operation of the pump can cause repeated in-plane stretching of diaphragm material as displacement volumes are created, which can cause a diaphragm to fail as a result of low cycle, high strain material fatigue. In some embodiments, the pressure and suction levels needed to stretch the material by an amount sufficient to actuate the valves can exceed the available pressure level in the pressure source 220 and/or the available vacuum level in the vacuum source 230 (see FIG. 16). Therefore, such embodiments might employ higher levels of pressure and vacuum to actuate the valves 101*i*, 101*o*, 102*i*, 102*o* to prevent the fluid pressures created in the pumping chambers 103*a, b* from overcoming the valve actuation pressures.

Further, variation in fluid pressures can be created in the pumping chambers 103*a, b* during a pumping stroke. In certain embodiments that include a sheet-like diaphragm without preformed actuation regions 141*a, b*, 151*i*, 151*o*, 152*i*, 152*o*, the diaphragm stretches to fill and discharge fluid and uses a dynamically changing portion of the pressure supplied to the pump chamber 103*a, b* in the stretching process. The pressure within the pump chamber as the chamber fills with fluid is related to the difference between the pressure supplied by a pressure source and the changing amount of pressure used to actuate and stretch the flat sheet diaphragm in its travel through a stroke. When the pump chamber discharges from a filled state, energy stored in the stretched diaphragm releases and increases the pressure supplied to the pump actuation chamber, which may result in pressure spikes in the outlet line 180*o*. In some embodiments, such pressure spikes can be undesirable. Similarly, when the pump chamber is filled from a discharged state, the energy stored in the stretched diaphragm releases and increases the suction supplied to the pump chamber 103*a, b*, which may result in suction spikes in the inlet line 180*i*. In some embodiments, such suction spikes can be undesirable. Some embodiments that include actuation regions 141*a, b* 151*i*, 151*o*, 152*i*, 152*o* thus can provide inlet line 180*i* and/or outlet line 180*o* pressures that have fewer spikes or fluctuations as a result of the actuation regions 141a, b, 151i, 151o, 152i, 152o transitioning between first and second states.

In certain embodiments, each of the diaphragms 140a, 140b, 150a, 150b is formed from a film having a substantially uniform thickness. The thickness of a diaphragm may be selected based on a variety of factors, such as the material or materials of which the diaphragm is composed, the size of the valve or chamber in which the diaphragm moves, etc. A diaphragm can be configured to separate a motive fluid from the process fluid during all stages of a stroke cycle and can be supported intermittently by surface features of the pump cavities (such as, for example, the seat rims 135i, 135o, 136i, 136o of the inlet and outlet valves 101i, 101o, 102i, 102o and/or the recesses 114a, b, 166a, b of the pump chambers 103a, b) when at an end of a stroke cycle. Accordingly, in some embodiments, the diaphragm media thickness is sufficiently thick to provide a substantially impermeable barrier between the process fluid and the motive fluid and to provide sufficient stiffness to resist substantial deformation when pressed against the surface features of the pump cavities. In some embodiments, the diaphragm thickness is also sufficiently flexible or pliable to transition between open and closed valve positions or between filled and discharged chamber positions with application of relatively small pressure differentials. In some embodiments, a thin diaphragm can have a lower level of mechanical strain when cycled between open and closed valve positions or between filled and discharged chamber positions than can a thicker diaphragm of otherwise like construction. The lower cyclic strain of a thin diaphragm can increase the lifespan of the diaphragm before mechanical failure of the material. In various embodiments, the diaphragm media has a thickness in a range between about 0.001 inches and about 0.060 inches, between about 0.002 inches and about 0.040 inches, between about 0.005 inches and about 0.020 inches, or between about 0.005 and about 0.010 inches.

In certain embodiments, higher ratios of minimum radius of bending curvature of the profile of the flexing portion of a preformed diaphragm to the diaphragm thickness may increase diaphragm cyclic life as the diaphragm transitions from one end-of-stroke position to another. In various embodiments, this ratio is in a range between about 5:1 and about 100:1, between about 10:1 and about 50:1, or between about 20:1 and about 30:1. In one embodiment, the diaphragm has a minimum radius of bending curvature of 0.25 inches and a diaphragm thickness of about 0.010 inches with a resulting ratio of 25:1.

FIG. 6A depicts an embodiment of a chamber diaphragm 140 before the regions 141a, 141b have been preformed or pre-stretched. In the illustrated embodiment, the diaphragm has been cut from a sheet of film. The diaphragm initially has a substantially uniform thickness and is then shaped to yield preformed or pre-stretched regions. FIG. 6B depicts chamber diaphragm 140 as it appears after being formed in forming fixture 300 as shown in FIGS. 7-8B. Other methods of forming actuation regions 141a, 141b in the diaphragm 140 are also possible, and the example described with respect to FIGS. 7-8B is merely provided by way of illustration.

FIGS. 7-8B depict the use of heat and vacuum to shape the regions 141a, b of a diaphragm 140. Many combinations of pressure, vacuum, and heat could also be used separately or together to form the regions in the diaphragms. For example, if only pressure is used, the residual stresses in the diaphragm shapes can cause the diaphragm form to change as the diaphragms are repeatedly cycled. In other embodiments, pressure is used to form the diaphragm regions and then the diaphragms are annealed by heating. For example, in some embodiments, the chamber diaphragms 140a, b are made of FEP film material that has a thickness of about 0.007 inches and a formed region perimeter of about 2.7 inches is overformed to a dome height of about 0.72 inches under pressure, then heated to approximately 60° C. for about 2 hours for a resulting dome height of about 0.36 inches. In a second example of pressure forming, in some embodiments, the chamber diaphragms 140a, b are made of PTFE film material that has a thickness of about 0.010 inches and a formed region diameter of 2.7 inches is overformed to a dome height of about 0.58 inches under pressure, then heated to approximately 60° C. for about 2 hours for a resulting dome height of about 0.36 inches. In various embodiments, the preformed diaphragm regions have a thickness in a range from about 0.001 inches to about 0.060 inches, from about 0.002 inches to about 0.040 inches, from about 0.005 inches to about 0.020 inches, or from about 0.005 to about 0.010 inches.

FIG. 7 depicts first plate 310 and second plate 320 of forming fixture 300 in an exploded view. Because forming fixture 300 is shown being used to produce a chamber diaphragm 140 (such as either of the diaphragms 140a or 140b), the o-rings depicted include o-rings 193a, 193b. First plate 310 can include chamber region recesses 311a, b that are circumscribed by o-ring grooves 312a, b. Plate 320 has portals 321a, b to allow heat to reach areas of the diaphragm that are being formed.

Figure 8A:
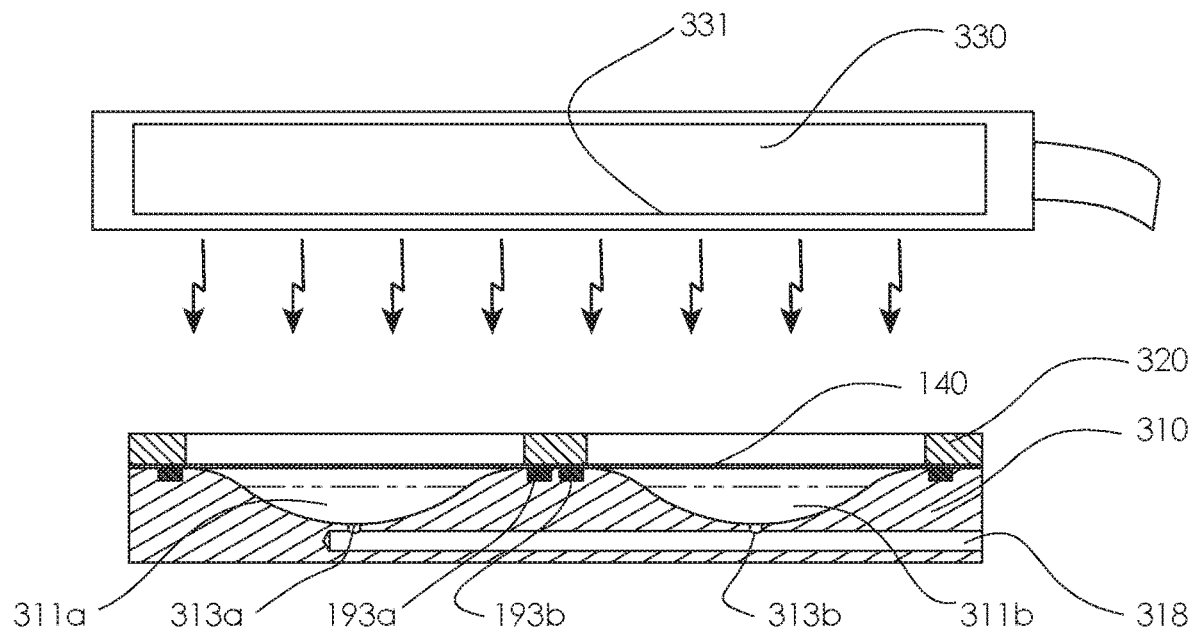
FIG. 8A is a cross-sectional view of a forming fixture after a diaphragm media has been loaded to form the regions in the chamber diaphragm.
Figure 8B:
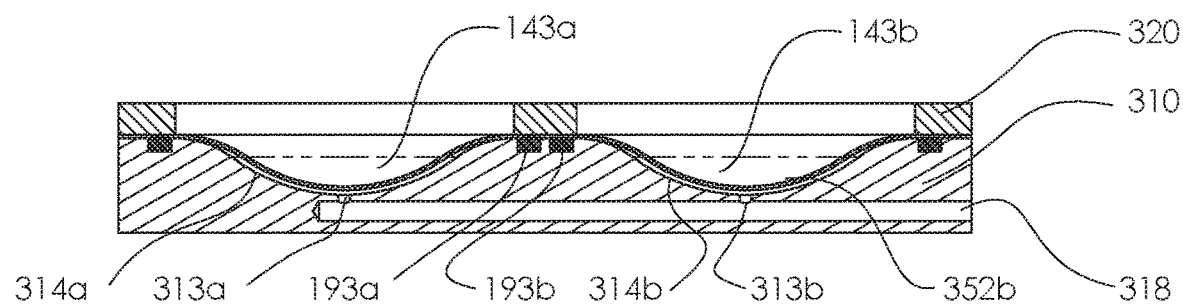
FIG. 8B is a cross-sectional view such as the view in FIG. 8A showing the forming fixture after the regions in the diaphragm media have been formed.

FIG. 8A shows a cross-sectional view of fixture 300 with a diaphragm media 140 between first plate 310 and second plate 320. The fixture 300 can be clamped together with mechanical fasteners or other assembly mechanisms to hold the diaphragm in position and seal the chambers created between the diaphragm and the chamber region recesses 311a, b. A vacuum is placed in fluid communication with these chambers via passage 318, which can include openings 313a, b into the chamber region recesses 311a, b, respectively.

A heater 330 (such as, for example, an infrared heater) is positioned to heat the regions of the diaphragm that are to be pre-shaped. In some embodiments, the diaphragm is substantially planar upon initial positioning between the first plate 310 and the second plate 310. The diaphragm film material can sag to a substantially non-planar configuration as it is heated and is exposed to a pressure differential, and the diaphragm material can conform to the surfaces 314a, b (see FIG. 8B) of the chamber region recesses 311a, b to form first pump chamber region 141a and second pump chamber region 141b. In some embodiments, the first plate 310 acts as a heat sink when regions of the diaphragm sag and come in contact therewith, and can prevent the diaphragm material from reaching a material transition temperature. Thus, in some embodiments, regions are fully formed after contact is made between the sagging portion of the diaphragm media and the first plate 310. FIG. 8B shows the fully formed chamber diaphragm 140 with the infrared heater removed.

In some embodiments, the chamber diaphragms 140a, b are made of FEP film material with a thickness of about 0.007 inches and assembled in a forming fixture 300 that is at a temperature of about 20° C. to about 40° C. In certain of such embodiments, a vacuum of about −10 psi is applied to passage 318 and an infrared heater 330 with a heater surface 331 operating at a temperature of 315° C. is positioned substantially parallel to and about 1.5 inches away from the surface of the flat diaphragm for about 1 minute.

The heater is then removed. In certain embodiments, without being limited by theory, a diaphragm 140 formed via thermoforming techniques retains its shape as it is repeatedly cycled in the pump because internal stresses in the diaphragm material are relieved during the heat forming process.

While FIGS. 7-8B depict the forming of chamber diaphragm 140a and 140b, a forming fixture configured uniquely to form the valve diaphragm regions and similar to forming fixture 300 can be used to form valve regions 151i, 151o, 152i, and 152o in valve diaphragms 150a and 150b.

FIGS. 9B and 9C are transverse cross-sectional views taken along the cutting lines shown in FIG. 9A to show the operation of an embodiment of first inlet valve chamber 101i, first outlet valve chamber 101o, second inlet valve chamber 102i, second outlet valve chamber 102o, first pump chamber 103a, and second pump chamber 103b. FIGS. 9B and 9C also show the operation of first chamber diaphragm region 141a and second chamber diaphragm region 141b of chamber diaphragms 140a, b.

FIG. 9B shows first inlet valve chamber 101i, first outlet valve chamber 101o, and first pump chamber 103a at the end of a fluid draw stroke. In FIG. 9B, the first chamber diaphragm region 141a of chamber diaphragms 140a, b is shown at an end-of-stroke position, where pressure has been applied through passage 173o to first outlet valve chamber 101o and vacuum is supplied through passage 173i to first inlet valve chamber 101i and also through passage 163a, as identified in FIG. 5, to first pump chamber 103a. Pressure in first outlet valve chamber 101o causes outlet valve region 151o of valve diaphragms 150a 150b to move (e.g., flex) and rest on or in close proximity to first outlet valve seat rim 135o, which in some instances can result in a substantially fluid-tight seal. The seal thus formed can substantially prevent fluid communication between first pump chamber 103a and outlet channel 138o via chamber channel 131o.

In some embodiments, suction in first outlet valve chamber 101o causes first inlet valve region 151i of valve diaphragms 150a, 150b to move (e.g., flex) away from first inlet valve seat rim 135i, thereby permitting fluid communication between inlet channel 138i and first pump chamber 103a via chamber channel 131i. Suction provided via passage 163a (see FIG. 5) can simultaneously move first pump chamber region 141a of chamber diaphragms 140a, b away from the pump body 110. In some embodiments, the suction can continue to move chamber region 141a after fluid communication between inlet channel 138i and first pump chamber 103a has been established, and can draw process fluid into the first pump chamber 103a. Process fluid can proceed through inlet line 180i (see, e.g., FIG. 1), through inlet channel 138i, through valve portal 131i, into first inlet valve chamber 101i, through chamber channel 133i, and into first pump chamber 103a.

FIG. 9C shows the second inlet valve chamber 102i, second outlet valve chamber 102o and second pump chamber 103b at the end of a fluid expel stroke. The second chamber diaphragm region 141b of chamber diaphragms 140a, 140b is shown at an end-of-stroke position where pressure has been applied through passage 174i to second inlet valve chamber 101i and through passage 164b (see also FIG. 5) to second pump chamber 103b, and a vacuum has been supplied through passage 174o to second outlet valve chamber 102o. In such an arrangement, pressure in second inlet valve chamber 102i prevents fluid communication between inlet channel 138i and second pump chamber 103b via chamber channel 134i and valve portal 132i by flexing second inlet valve region 152i of chamber diaphragms 150a, 150b to rest on or in close proximity to second inlet valve seat rim 136i. Simultaneously, suction applied to second outlet valve chamber 102o flexes first outlet valve region 152o of chamber diaphragms 150a, 150b away from second outlet valve seat rim 136o and allows fluid communication between second pump chamber 103b and outlet channel 138o via chamber channel 134o and valve portal 132o. Simultaneously, pressure provided to chamber 103b continues to push against second pump chamber region 141b of chamber diaphragms 140a, 140b and expels process fluid through chamber channel 134o into second outlet valve chamber 102o and then through valve portal 132o into outlet channel 138o, which is in fluid communication with outlet line 180o.

In some embodiments, the inlet valves 101i, 102i actively control ingress of process fluid into the first and second pump chambers 103a, b, and the outlet valves 101o, 102i actively control egress of process fluid from the first and second pump chambers 103a, b, respectively. As used herein, the term "actively control" means that the valves 101i, 101o, 102i, 102o can be actuated without dependency on the direction of the flow of process fluid through the pump 100. For example, the actuation medium that controls the transitioning and positioning of the valves 101i, 101o, 102i, 102o can do so independent of the reversal of flow of process fluid through the valve.

In some embodiments a preformed diaphragm region (e.g., 141b, 152i, 152o) defines its natural preformed shape when in an end-of-stroke position. For example, the preformed region 152o shown in FIG. 9C can be in its natural state in the illustrated end-of-stroke position. When in another end-of-stroke position, the preformed region can define an inversion of the natural preformed shape. For example, in some embodiments, the preformed region 152o is in its natural preformed shape when in the end-of stroke position shown in FIG. 9C, and can move to inversion of its natural preformed shape when moved to another end-of-stroke position at or near the seat rim 136o (such as the position of preformed region 151o shown in FIG. 9B). Alternatively, the preformed region 152o can be in its natural preformed shape when in an end-of-stroke position at or near the seat rim 136o and can transition to an inversion of the preformed shape at an opposite end-of-stroke position.

In some embodiments, it can be desirable for a preformed diaphragm region to be in its natural preformed shape when at an end-of-stroke position, as this can reduce strain on the diaphragm region in certain arrangements. In other embodiments, the diaphragm region can pass through its preformed shape before reaching an end-of-stroke position, which may, in some instances, cause the region to stretch in order to reach the end-of-stroke position. In still other embodiments, the diaphragm region may be prevented from achieving its natural preformed shape when operating within a pump chamber or valve chamber.

In some embodiments, it can be advantageous to switch from an expel stroke to a draw stroke before a diaphragm reaches an end-of-stroke condition, such as the position shown in FIG. 9C. Similarly, in some embodiments, it can be advantageous to switch from a draw stroke to an expel stroke before a diaphragm travels to an end-of-stroke condition such as that shown in FIG. 9B. In some embodiments, when the pump chambers are alternately and repeatedly switched between a draw stroke and an expel stroke prior to the chamber diaphragms 140a, 140b reaching an end-of-stroke position during the draw stroke, fluid flow through the inlet line 180i can be substantially constant. In other embodiments in which expel strokes allow the chamber diaphragms 140a, 140b to reach an end-of-stroke position, the pause in displacement of fluid during the duration of time at the end-of-stroke can cause a pulsatile output flow in the outlet line 180o. In some applications it can be advantageous to balance the pump 100 to control the pump chambers to switch from a draw stroke to an expel stroke prior to the chamber diaphragms reaching either end-of-stroke position.

FIG. 10 shows another embodiment of a double diaphragm pump 100' shown in cross-section with a view such as that shown in FIG. 9B. In certain embodiments, the pump 100' is configured to stall if air is drawn into the pump 100' along with the process fluid. In some embodiments, it can be advantageous in blood pumping applications to cause the pump to stall if a significant air volume is drawn into the inlet channel 138i. Such air intake could be due, in some rare instances, to negative suction in the inlet line that entrains air through a leak in a fitting or, in other rare instances, at the connection to a patient or by inadvertent error by the practitioners. The pump body 110' can include bypass channels 139i, 139o that allow continuous or uninterrupted fluid communication between the inlet channel 138i and the first pumping chamber 103a and between the first pumping chamber 103a and the outlet channel 138o, respectively. For example, in the illustrated embodiment, although the diaphragm 150a forms a seal with seat rim 135o, fluid communication is still possible between the first pumping chamber 103a and the outlet channel 138o because the bypass channel 139o provides a fluid path from the pumping chamber 103a to the groove 121o, which is in fluid communication with the outlet channel 138o (compare FIG. 4). The pump body 110' can include similar bypass channels that provide continuous or uninterrupted fluid communication between the inlet channel 138i and the second pumping chamber 103b and between the second pumping chamber 103b and the outlet channel 138o.

The bypass channels 139i, 139o can have flow areas that are much smaller than those defined by the valve portals 131i, 131o and chamber channels 133i, 133o. A volume of air can flow through an opening at a faster rate than a like volume of liquid. Accordingly, in the event of a significant volume of air being introduced into inlet channel 138i along with process fluid, the double diaphragm pump 100 will cause liquid to flow less efficiently through the pump, and air will fill the pump chambers 103a, 103b through the bypass channels 139i, 139o and then return back through the bypass channels and may prevent continually expelling air into the outlet channel 138o and then into the outlet line 180o.

For example, in some embodiments, a mixture of process fluid and air may enter the first chamber 103a from the inlet channel 138i during a fluid draw stroke. As the diaphragms 140a, b move toward the pump body 110' to decrease the volume of the chamber 103a during an expel stroke, air within the chamber 103a may preferentially exit the chamber 103a via the bypass channel 139i and return to inlet channel 138i. This air, and possibly additional air received via the inlet channel 138i, may gather or collect in the chamber 103a and may cycle back and forth through the bypass channels 139i, 139o over the course of repeated intake and expel strokes. Eventually, sufficient air may gather in the chamber 103a to cause the pump 100' to operate less efficiently or to stall. For example, as an increasing volume of air passes through the bybass channel 139o to gather in a chamber 103a, the amount of blood that can be drawn into the chamber 103a and subsequently expelled from the chamber 103a can decrease due to the presence of the air.

With reference again to FIG. 9C, in certain embodiments, the pump 100 comprises a mounting hook 175. In some embodiments, the mounting hook 175 extends from the valve plate 170 in a direction substantially orthogonal to a plane defined by a base surface of the valve plate 170. The mounting hook 175 can define an opening 175a. In some embodiments, the hook 175 extends in substantially the same direction as the bosses 176a-d. The hook 175 and bosses 176a-d are further discussed below.

In some embodiments, the double diaphragm pump 100 is constructed with the inlet and outlet valve chambers 101i, 101o, 102i, 102o and the pump chambers 103a, b located on the same side of the pump body 110. The pump chambers 103a, b can also be located on opposite sides of the pump body 110 while the inlet and outlet valves 101i, 102i, 101o, 102o can be located on the opposite side of the pump body 110 from their associated pump chamber 103a, b. The pump body 110 can be constructed with more than two pump cavities 103a, b, more than two inlet valves 101i, 102i, and more than two outlet valves 112i, 112o to cooperatively work in pumping a single fluid. Also, multiple double diaphragm pumps 100 can be constructed on a single pump body 110. The diaphragms 140a, b, 150a, b can also have more valve regions 151i, 151o, 152i, 152o and pump chamber regions 141a, 141b than those shown in the depicted embodiments.

Components of the double diaphragm pump 100, or portions thereof, that are exposed to a process fluid (such as, for example, blood) can be constructed of any suitable material that is compatible with the process fluid. For example, in some embodiments, the pump 100 comprises any suitable blood-compatible material, whether currently known in the art or yet to be devised. Examples of such candidate materials can include plastic materials, such as polycarbonate (PC), polyvinyl chloride (PVC), polypropylene (PP), polyethylene (PE), polytetrafluoroethylene (PTFE), polyperfluoroalkoxyethylene (PFA), fluorinated ethylene propylene (FEP), and polyurethane (PU). In some embodiments, metal materials can be used, such as stainless steel 316L and/or titanium. In some embodiments, the body 110 is constructed of PC. The body 110 can be substantially rigid and relatively inflexible, in some arrangements.

In certain embodiments, the chamber diaphragms 140a, 140b and valve diaphragms 150a, 150b may be formed from a polymer or an elastomer. In some embodiments, polymers that have high endurance to cyclic flexing may be used, such as, for example, a fluorpolymer, such as polytetrafluoroethylene (PTFE), polyperfluoroalkoxyethylene (PFA), or fluorinated ethylene propylene (FEP). Other nonelastomer film materials may be used, such as PE, PVC, PP. In some embodiments, an elastomeric material such as silicone or polyurethane can be used for the diaphragms 140a, b, 150a, b. In certain of such embodiments, it is preferable that supporting structures be configured so as to prevent plastic hinges (e.g., relatively sharp bends in material where the diaphragm is forced by pressure into contact with features in the actuation cavities) that may cause cyclic failure.

In some embodiments, components of the pump 100 that do not contact a process fluid can be constructed of any of a variety of materials without consideration of possible incompatibilities among the materials and the process fluid. For example, in some embodiments, materials used for the chamber plate 160 and valve plate 170 can be any suitable plastic or metal material. In many embodiments, the chamber plate 160 and the valve plate 170 are substantially rigid and can be relatively inflexible.

The inlet line 180i and outlet line 180o can be made from any suitable material, and can be compatible with the process fluid. In some embodiments, the lines 180i, 180o comprise a blood compatible PVC material containing softening plasticizers, such as Tygon® S-95-E tubing available from Saint Gobain Performance Plastics, Akron, Ohio.

Figure 11:
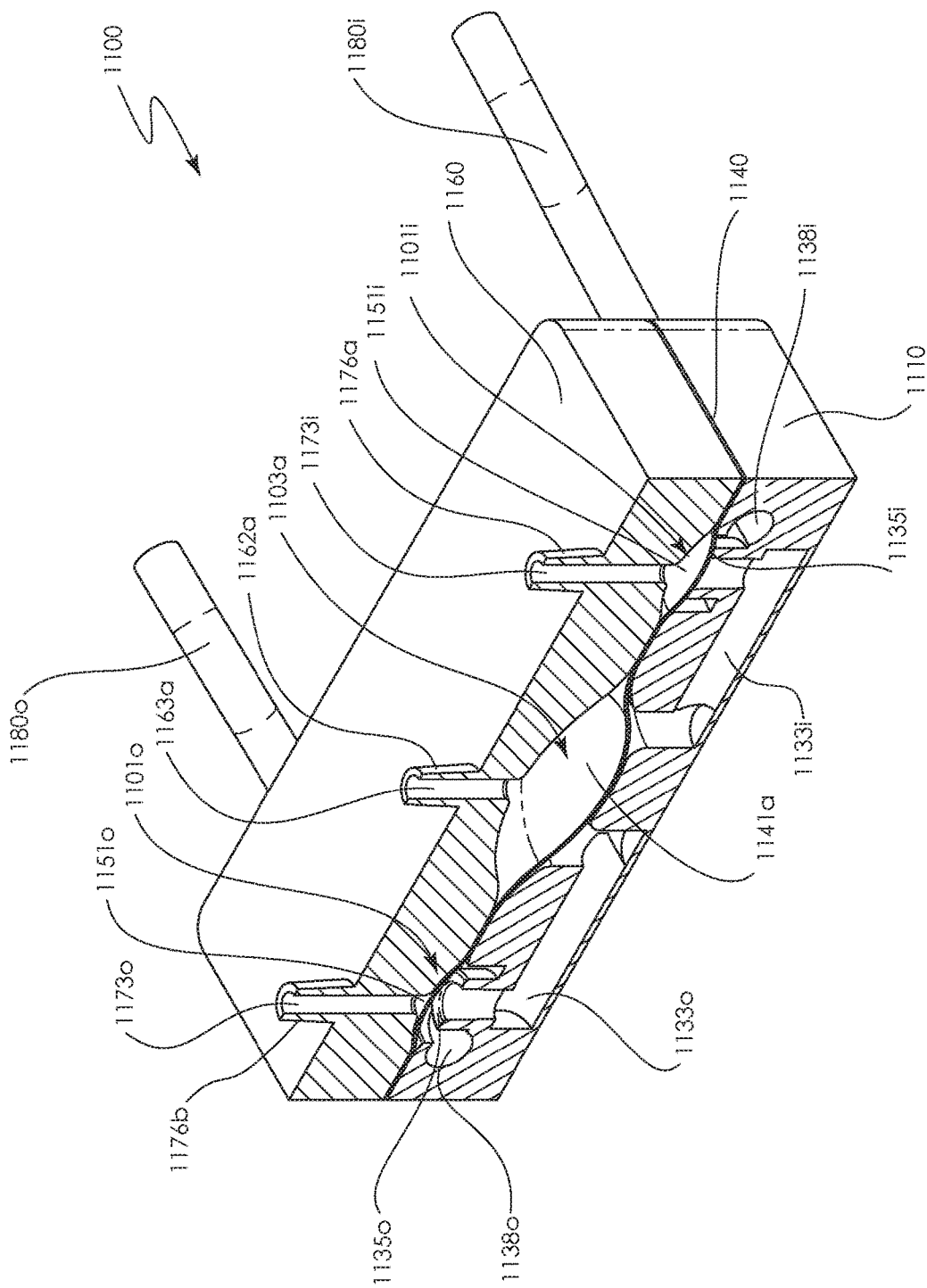
FIG. 11 is a cross-sectional perspective view of another embodiment of a diaphragm pump.

FIG. 11 illustrates an embodiment of a pump 1100. The pump 1100 can include features such as those described above with respect to the illustrated embodiments of the pumps 100 and 100'. Accordingly, features of the pump 1100 are identified with reference numerals incremented by 1000 relative to reference numerals used to identify like features of the pumps 100, 100'.

In certain embodiments, the pump 1100 can be in fluid communication with an inlet line 1180i and an outlet line 1180o. The pump 1100 can comprise a pump body 1110, which can define an inlet channel 1138i in fluid communication with the inlet line 1180i and an outlet channel 1138o in fluid communication with the outlet line 1180o. The pump 1100 can further comprise a chamber plate 1160, which can cooperate with the pump body 1110 to at least partially define a first pump chamber 1103a, a first inlet valve 1101i, and a first outlet valve 1101o. In some embodiments, one or more diaphragms 1140 are included between the pump body 1110 and the chamber plate 1160. The one or more diaphragms 1140 can include one or more diaphragm actuations regions 1141a, 1151i, 1151o configured to move within the first pump chamber 1103a, the first inlet valve 1101i, and the first outlet valve 1101o, respectively.

In some embodiments, the pump body 1110, the chamber plate 1160, and the one or more diaphragms 1140 further define a second pump chamber, a second inlet valve, and a second outlet valve (not shown) such as the illustrated first pump chamber 1103a, first inlet valve 1101i, and first outlet valve 1101o, respectively. The inlet channel 1138i can extend between the first inlet valve 1101i and the second inlet valve, and the outlet channel 1138o can extend between the first outlet valve 1101o and the second outlet valve.

In some embodiments, the first inlet valve 1101i includes a seat rim 1135i and the second inlet valve 1101o includes a seat rim 1135o. The pump body 1110 can define a chamber channel 1133i that provides fluid communication between the seat rim 1135i of the first inlet valve 1101i and the first pump chamber 1103a and can define another chamber channel 1133o that provides fluid communication between the pump chamber 1103a and the seat rim 1135o of the first outlet valve 1101o. In some embodiments, the diaphragm actuation region 1151i is configured to selectively permit fluid communication between the inlet channel 1138i and the chamber channel 1133i. Similarly, the diaphragm actuation region 1151o can be configured to selectively permit fluid communication between the chamber channel 1133o and the outlet channel 1138o.

In some embodiments, the chamber plate 1160 defines a motive fluid passage 1173i in fluid communication with the first inlet valve 1101i, a motive fluid passage 1173o in fluid communication with the first outlet valve 1101o, and a motive fluid passage 1163a a in fluid communication with the first pump chamber 1103a. The motive fluid passages 1173i, 1173o, and 1163a can be at least partially defined by motive fluid transfer bosses 1176a, 1176b, and 1162a, respectively. In some embodiments, the bosses 1176a, 1176b, and 1162a are configured to be connected with a motive fluid control device. In some embodiments, motive fluid is provided to the valves 1101i, 1101o and the pump chamber 1103a to actuate the diaphragm actuation regions 1151i, 1151o, and 1141a, respectively. In some embodiments, such as that illustrated in FIG. 11, motive fluid at a first pressure can be provided to both the first inlet valve 1101i and the first pump chamber 1103a, and motive fluid at a second pressure can be provided to the first outlet valve 1101o.

Figure 12:
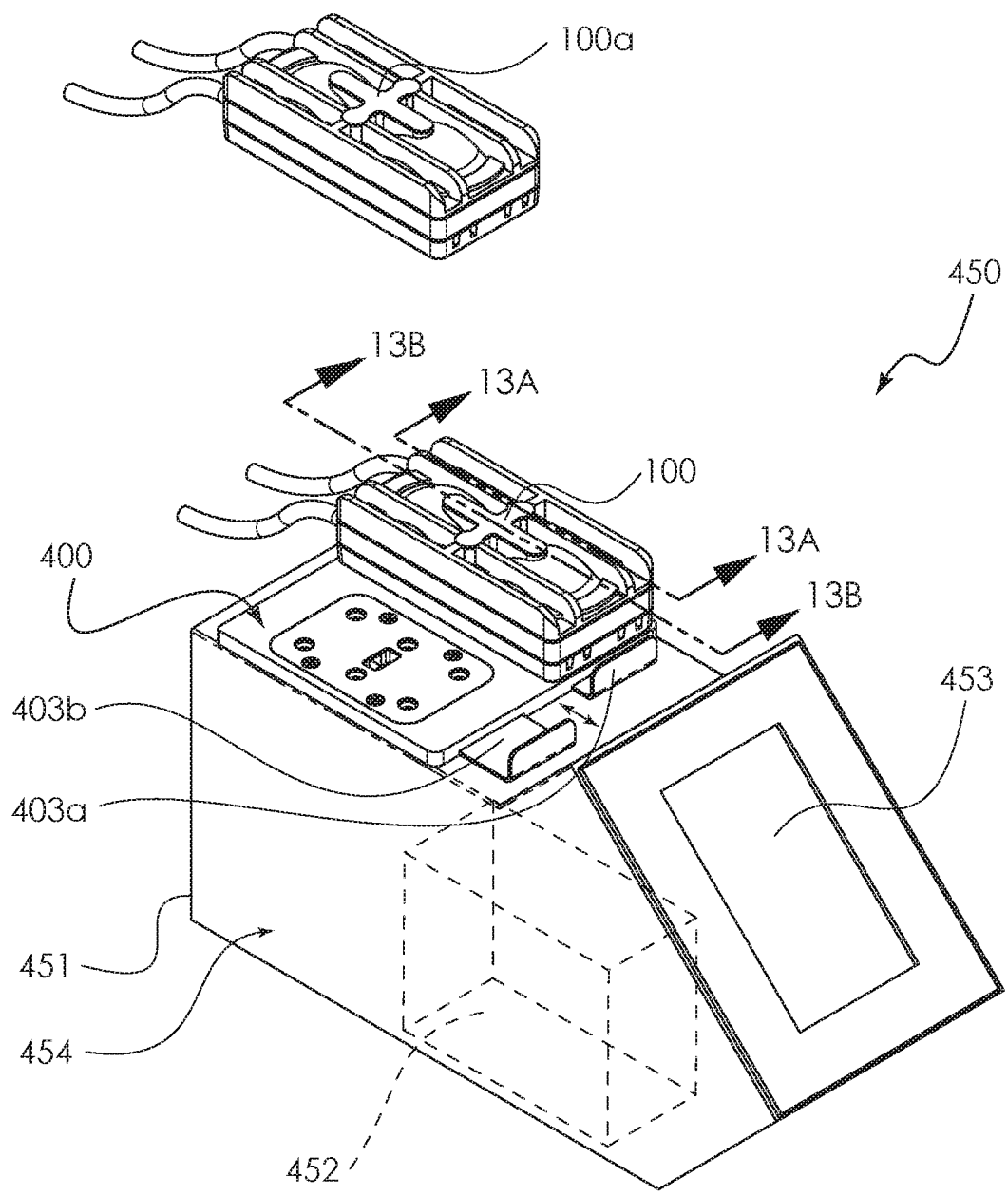
FIG. 12 is a partially exploded perspective view of two double diaphragm blood pumps configured for operative association with a reusable pump control system.
Figure 13A:
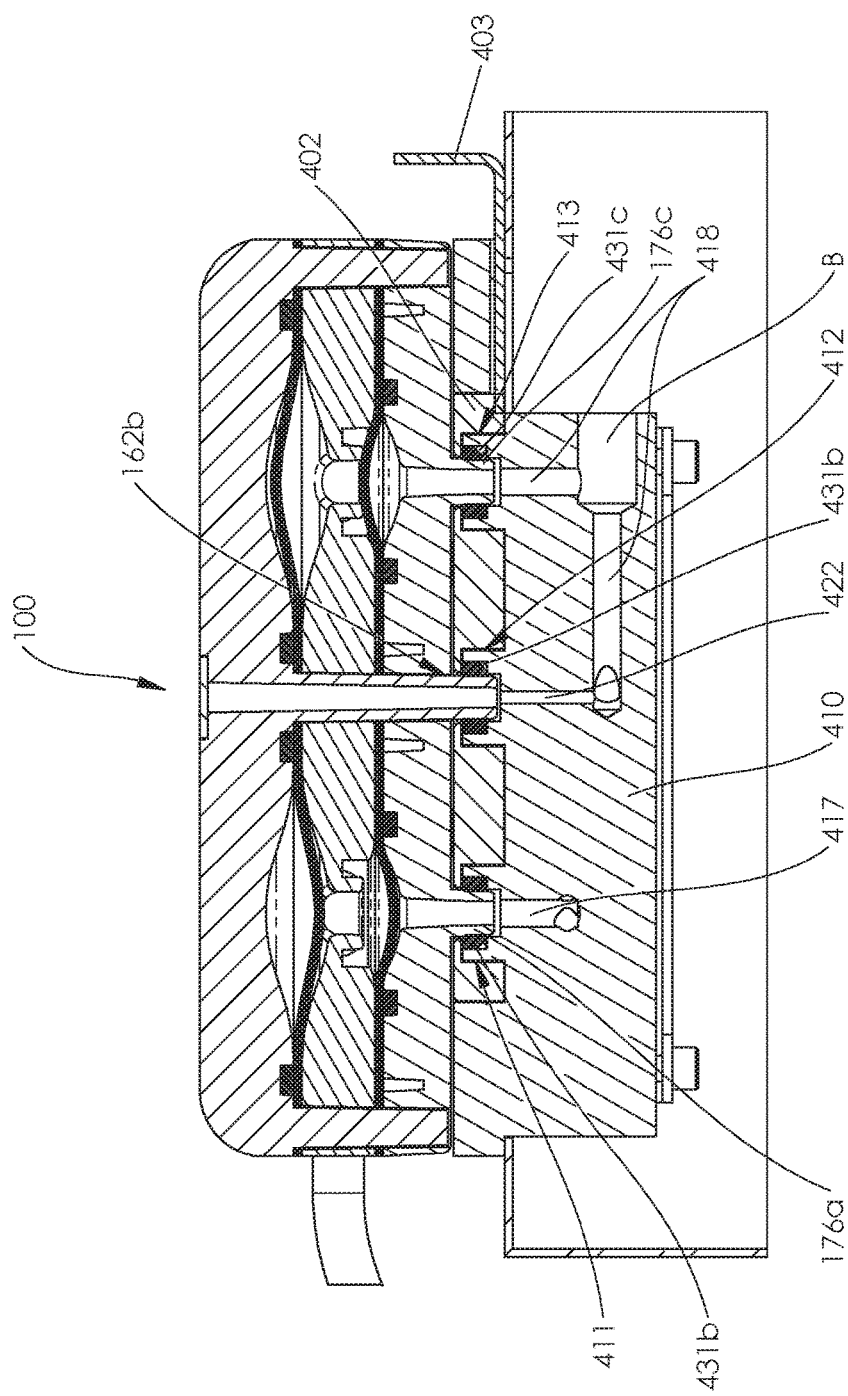
FIG. 13A is a partial cross-sectional view of a double diaphragm pump and manifold taken along cutting line 13A-13A in FIG. 12.
Figure 13B:
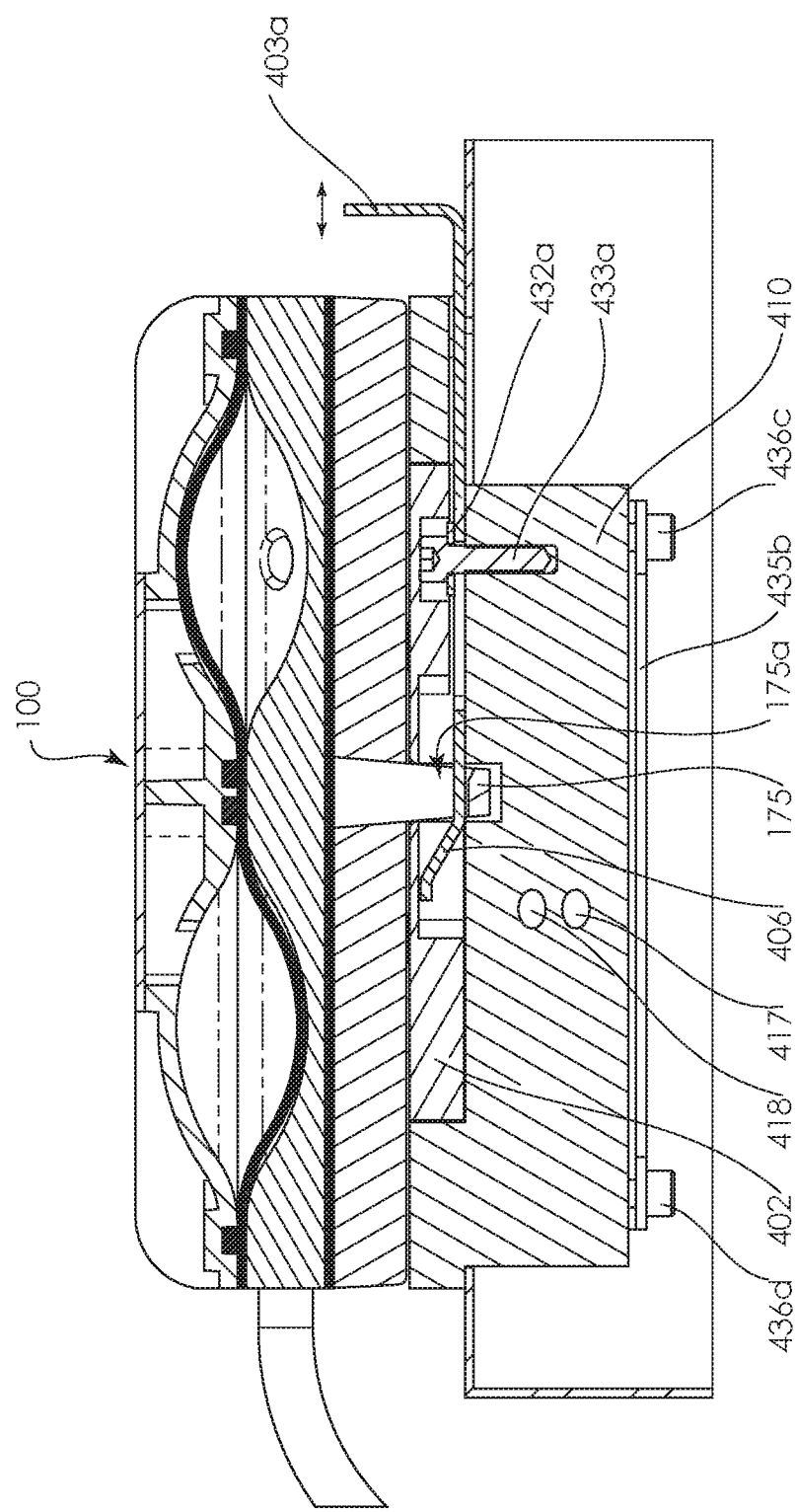
FIG. 13B is a partial cross-sectional view of a double diaphragm pump and manifold taken along cutting line 13B-13B in FIG. 12.

With reference to FIGS. 12-13B, in certain embodiments, a pump assembly 450 can include a reusable control base or pump control system 451 and one or more double diaphragm pumps 100, 100a. The control system 451 and one or more diaphragm pumps 100, 100a can be configured to selectively couple and decouple. In some embodiments, the one or more diaphragm pumps 100, 100a can be used with the control system 451 in a single procedure or a limited number of procedures, removed from the control system 451, and then discarded. Additional diaphragm pumps 100, 100a can replace the discarded diaphragm pumps 100, 100a in one or more additional procedures. Accordingly, in some embodiments, the control system 451 can be used in multiple procedures (whether of the same or different variety) with a plurality of disposable diaphragm pumps 100, 100a.

As further discussed below, in some embodiments, the control system 451 can control the manner in which the pumps 100, 100a operate. The control system 451 can operate a set of pumps 100, 100a in a variety of different modes, depending on the type of procedure involved. In some embodiments, the control system 451 is reconfigurable, such that the manner in which the control system 451 controls the pumps 100, 100a can be altered. The control system 451 can comprise a fluid logic system configured to direct motive fluids from different sources (e.g., motive fluids at different pressure levels) to different portions of each pump 100, 100a, and in further embodiments, can alternate which motive fluids sources are directed to the portions of the pumps 100, 100a.

In certain embodiments, the control system 451 comprises a processor 452, which can comprise any suitable logic processor or controller, and may comprise, for example, an on-board computer. In some embodiments, the processor 452 is configured to run executable computer code, and can include volatile and/or non-volatile memory. In further embodiments, the processor 452 can be configured to communicate with other devices, and may be part of a network.

In some embodiments, the control system 451 includes a user control interface 453. The interface 453 can be of any suitable variety, and can be configured to communicate information to and/or from the processor 452. For example, the interface 453 can include one or more display screens, touch screens, keyboards, mouse controllers, switches, indicators, and/or speakers. In some embodiments, instructions can be provided to the processor 452 via the interface 453. For example, in some embodiments, the processor 452 is capable of operating in a variety of different modes and the interface 453 can be used to select among the available modes. The interface 453 may also be used to program the processor 452 to operate in a new or different mode.

As further discussed below, in some embodiments, the control system 451 comprises one or more pneumatic regulators and/or vacuum generators, which can control the pressure level of a pressure source 220 and/or a vacuum source 230 (see FIG. 16); one or more motive fluid valves 210 (see FIG. 16), which can comprise one or more air valves, and/or other pneumatic control and conditioning devices; and/or other suitable control hardware. In some embodiments, the pressure source and vacuum source can be supplied to the control system by connections to external systems that are configured to supply pressurized gases or suction of gases. In some embodiments, such components and devices can be in communication with and/or controlled by the processor 452 (e.g. the setting of the pneumatic regulators that control the pressure level in a motive fluid source may be controlled by the processor).

With continued reference to FIG. 12, in certain embodiments, the control system 451 comprises an enclosure 454 and a manifold mounting assembly 400. In some embodiments, the enclosure 454 and the manifold mounting assembly 400 cooperate to form a cavity in which one or more components of the control system 451 (e.g., the processor 452, pressure source 220, and/or vacuum source 230) are contained. The manifold mounting assembly 400 can be configured to interface with one or more pumps 100, 100a and to selectively couple the pumps 100, 100a with the system 451. FIG. 12 shows an embodiment of a pump 100 in locked engagement with the manifold mounting assembly 400 and a second pump 100a disengaged from the manifold mounting assembly 400. The illustrated embodiment is particularly suited for use with one or two pumps 100, 100a. In some embodiments, the mounting assembly 400 can be used with more pumps than pumps 100, 100a.

Figure 14:
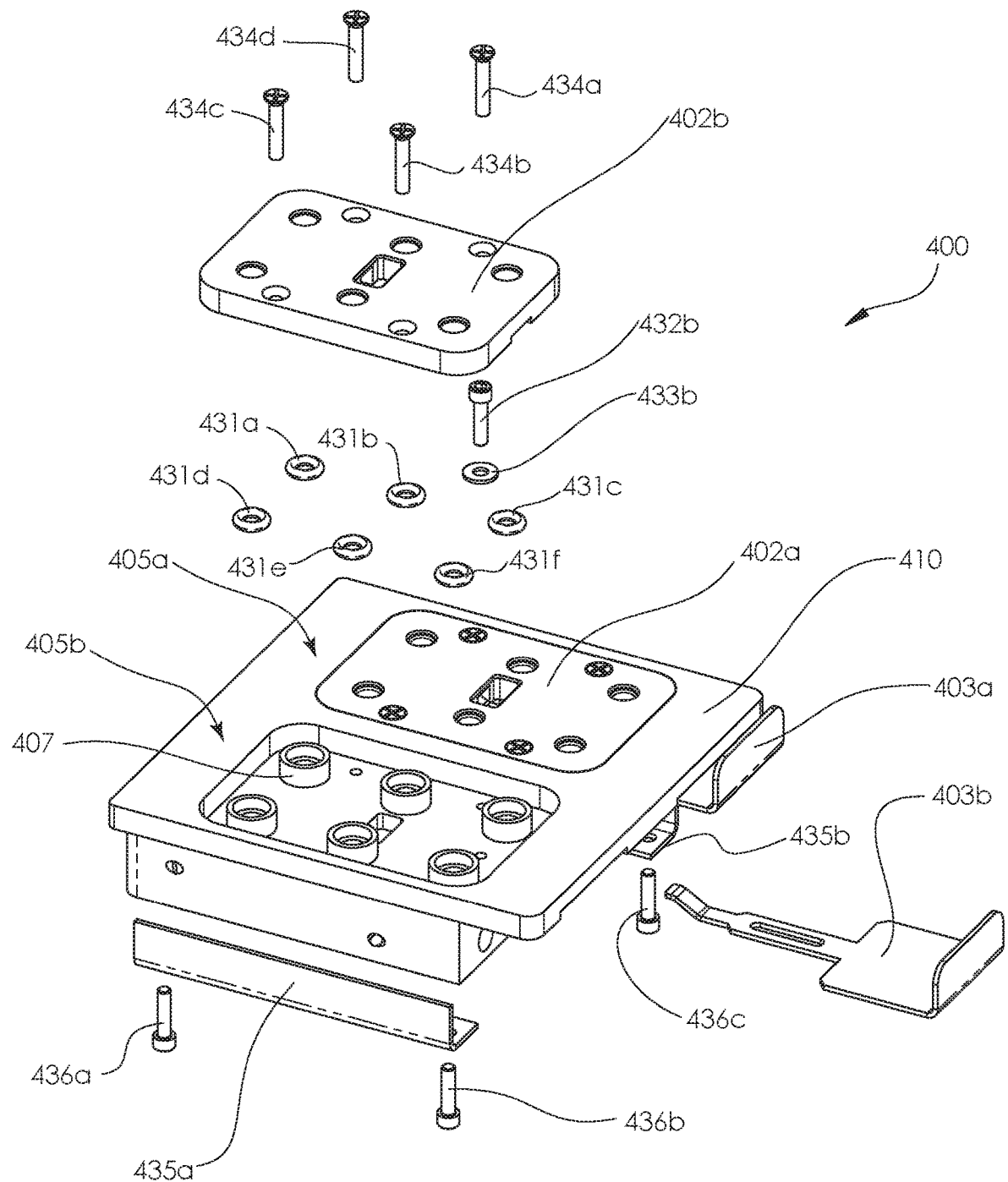
FIG. 14 is a partially exploded perspective view of an embodiment of a manifold mounting assembly.

FIG. 14 illustrates a partially exploded perspective view of an embodiment of the manifold mounting assembly 400. The illustrated embodiment includes two pump mounting areas 405a, b, each of which includes similar components and features. Accordingly, for convenience and not by way of limitation, the following discussion may refer to a feature of one of the pump mounting areas 405a, b without referring to a like feature of the other mounting area, or may refer to like features interchangeably. Other embodiments can include more than two pump mounting areas 405a, b and/or can include pump mounting areas that include dissimilar features.

In certain embodiments, each pump mounting area 405a, b of the manifold mounting assembly 400 comprises a manifold cover 402a, b. The manifold cover 402b can extend over and substantially shield a series of air transfer bosses 407 (see also FIG. 15). The cover 402b can define an opening associated with each air transfer boss 407 of the manifold mounting assembly 400 for receiving an air transfer boss 162a,b or 176a-d of a pump 100a. As further discussed below, the air transfer bosses 162a,b, 176a-d of the pump 100a can extend through the openings and into the air transfer bosses 407. The manifold cover 402b can further define an opening through which a mounting hook 175 can extend (see FIGS. 9C and 13B).

In certain embodiments, each air transfer boss 407 can receive a sealing element, such as an o-ring 431a-e, to facilitate or enable creation of a fluid-tight seal between the air transfer bosses 407 and the air bosses 162a, b, 176a-d of the pump 100a. Once the o-rings 431a-e are in place, the manifold cover 402b can be placed over the air transfer bosses 407 and secured to the manifold mounting assembly 400 via any suitable fastener, such as one or more screws 434a-d. In some embodiments, each o-ring 431a-e is retained between and is in fluid-tight contact with a ridge of an air transfer boss 407 and an underside of the manifold cover 402b.

In some embodiments, the manifold mounting assembly 400 comprises latches 403a, b that interact with the mounting hook 175 (see FIGS. 9C and 13B) of a pump 100 to selectively secure the pump 100 to the manifold mounting assembly 400. As depicted by double-headed arrows in FIGS. 12 and 13B, the latch 403a can move outward or inward relative to a pump 100. In some embodiments, the latch 403 is moved inward relative to the pump 100 and advanced through the mounting hook 175 to secure the pump 100 to the manifold mounting assembly 400, and is moved outward relative to the pump 100 and removed from the opening 175a defined by the hook 175 to permit removal of the pump 100 (see FIG. 13B).

In some embodiments, the latch 403a comprises a catch 406 (see FIG. 13B). The catch can provide leveraged force against the mounting hook 175 as it is slid forward to assist in energizing the radial o-ring seals 431a-f for creating sealed fluid interfaces between pump 100 and manifold mounting assembly 400.

In certain embodiments, a screw 432b and a washer 433b are used in conjunction with a manifold plate 410 to constrain the motion and positioning of latch 403b. For example, in the embodiment illustrated in FIG. 13B, the screw 432a extends through the washer 433a, through an opening in the latch 403b, and into the manifold plate 410. In other embodiments, one or more other mechanisms may be used to selectively attach a pump 100 to the manifold mounting assembly 400. For example, clips, bolts, screws, clamps, or other fasteners could be used.

With reference to FIGS. 13B and 14, in some embodiments, the manifold mounting assembly 400 includes one or more brackets 435a, b and fasteners 436a-d, which can be used to secure the manifold mounting assembly 400 to enclosure 454.

Figure 15:
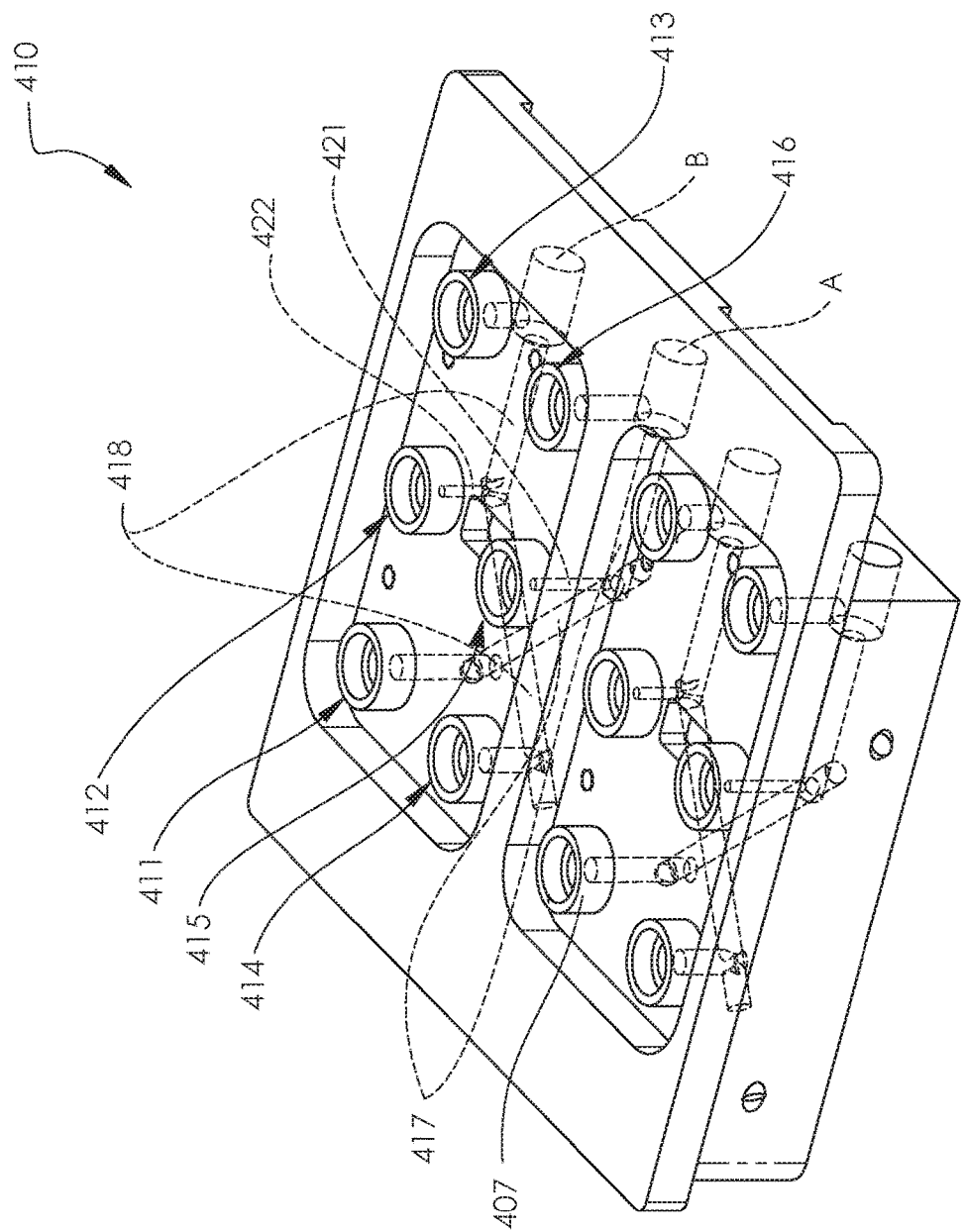
FIG. 15 is a perspective view of an embodiment of a manifold base with a portion of the interior features of the manifold base shown in phantom.

With reference to FIG. 15, in certain embodiments, the manifold mounting assembly 400 includes air passages 417, 418 (see also FIGS. 13A and 13B). In some embodiments, air passage 417 provides fluid communication between a first supply port A and air transfer bosses 411, 415, and 416 and air passage 418 provides fluid communication between a second supply port B and air transfer bosses 412, 413, and 414. As further discussed below, in some embodiments, the supply ports A, B are in fluid communication with a motive fluid control valve 210 (see FIG. 16), which can be configured to selectively permit one or more motive fluids to flow to or from the supply ports A, B.

In some embodiments, when the pump 100 is connected to the control system 451, the air transfer bosses 162a, b, 176a-d of the pump 100 are in fluid communication with the air transfer bosses 411-416 of the manifold mounting assembly 400. For example, in some embodiments, the air transfer bosses 412, 413, and 414 are connected with air transfer bosses 176c, 162b, and 176b of the double diaphragm pump 100 to provide for actuation of the second inlet valve 102i, second pump chamber 103b, and first outlet valve 101o. Similarly, the air transfer bosses 411, 415, and 416, are connected with air transfer bosses 176d, 162a, 176a of the air diaphragm pump 100 to provide for actuation of the first inlet valve 101i, first pump chamber 103a, and second outlet valve 102o.

In some embodiments, the air passages 417, 418 include restrictions 421, 422, respectively. For example, the air passages 417, 418 can include transfer passages to redirect the flow of motive fluid toward the air transfer bosses 411-416 (see FIGS. 13A and 15). In some embodiments the transfer passages associated with air transfer bosses 412 and 415 are smaller than those associated with air transfer bosses 411, 413, 414, and 416. Accordingly, in some embodiments, the restrictions 421, 422 comprise the smaller transfer passages, and can reduce the rate of change in motive fluid pressure in pump chambers 103a, b by restricting air flow through air transfer bosses 412 and 415 as compared with the rate of change in motive fluid pressure in valve chambers by not significantly restricting air flow to or from the bosses 411, 413, 414, and 416. This permits the inlet and outlet valves to open and close rapidly relative to the filling and discharging of the pump chambers. Further, in some embodiments, the volume of the valves 101*i*, 101*o*, 102*i*, 102*o* is also smaller than the volume of the pump chambers 103*a, b*, which can permit the valves to remain open or closed during a substantial portion of a given stroke cycle. In some embodiments, pressure sensors can be placed in fluid communication with the air transfer passages on the pump side of the restrictions 421, 422. The process fluid inlet pressure to the pump and outlet pressure from the pump can be monitored due to the motive fluid pressure at these locations and the process fluid pressure are closely related when the diaphragm regions 141*a, b* are not in an end-of-stroke position during the pump cycle.

In some embodiments, such as the embodiment illustrated in FIGS. 12-15, the control system 451 is capable of actuating the flow control valves 101*i*, 101*o*, 102*i*, 102*o* and the pump chambers 103*a, b* using a single level of pressure in one of the passages 417, 418 and a single level of suction in the other passage 417, 418 during a given stroke or portion of a stroke. Such a configuration can reduce the number of air valves, air regulators, and air control devices (such as those described below) used by the pump control system 451, which can, in some cases, reduce the manufacturing costs, reduce the complexity, decrease the potential probability of mechanical failure, and/or increase the ease of use and/or the reliability of the pump assembly 450.

FIG. 16 depicts a schematic illustration of another embodiment of the pump assembly 450, and includes like reference numerals to identify like features disclosed in other figures of the present disclosure. The pump assembly 450 can comprise a motive fluid logic system 460 configured to control a double diaphragm pump 100. In some embodiments, the motive fluid logic system 460 comprises the control system 451 (see FIG. 12). The logic system 460 can comprise a processor 452 such as described above. In some embodiments, the processor 452 is in communication (e.g., electrical, wireless, or other communication) with a valve controller 212 and can control the operation thereof. As discussed above, in some embodiments, the processor 452 is pre-programmed with one or more operational modes by which it controls the controller 212, and in further embodiments, the processor 452 can be reconfigurable.

In some embodiments, the valve controller 212 is configured to effect transition of a motive fluid valve 210 among a variety of operational states. In some embodiments, the valve controller 212 comprises an electrical actuator (or controller) or a pneumatic actuator (or controller), which can transition the valve 210 among the operational states.

In some embodiments, the valve 210 is configured to operate in two or more positions and may include a resting state, a first state, and a second state. In the illustrated embodiment, the resting, disconnected, closed, or shutoff state of the valve 210 corresponds with the middle rectangular section, the first operational state corresponds with the top rectangular section, and the second operational state corresponds with the bottom rectangular section. In some embodiments, the resting state of the valve 210 substantially prevents fluid communication between the pump 100 and the pressure source 220 and vacuum source 230. The valve 210 can be positioned in this state, for example, during installation and removal of the pump 100 or during a pump "off" condition or pump "shut down" condition.

In some embodiments, the valve 210 provides fluid communication between a pressure source 220 and the supply port A and between a vacuum source 230 and the supply port B when in the first state, and provides fluid communication between the pressure source 220 and the supply port B and between the vacuum source 230 and the supply port A when in the second state. As indicated by the double-headed arrow, in some embodiments, the valve 210 passes through the resting state when transitioning between the first and the second operational states. Other arrangements of the valve 210 are also possible. For example, the first and second operational states of the valve 210 can be positioned adjacent to each other such that the valve 210 does not pass through the resting state in transitioning between the first and second operational states. In other embodiments, multiple motive fluid valves 210 can be used.

The pressure source 220 can comprise any suitable source of motive fluid such as, for example, an air compressor, a pressurized canister, connection to a pressurized air line, etc. Similarly, the vacuum source 230 can comprise any suitable source of motive fluid (or, in some instances, a relative lack thereof), such as, for example, a connection to a rarefied air line or a vacuum generator or an air compressor configured to evacuate or partially evacuate a chamber. In some embodiments, the vacuum source 230 comprises a vent to atmosphere, and the pressure source 220 is pressurized to a level that exceeds that of atmospheric pressure. In some embodiments, the pressure source 220 and/or the vacuum source 230 can comprise one or more pneumatic regulators to help achieve a relatively constant pressure level. As an example, in some embodiments, the pressure source 220 can comprise a first motive fluid, such as compressed air at a first pressure level (e.g., about 300 mmHg (millimeters of mercury)), and the vacuum source 230 can comprise a second motive fluid, such as rarefied air at a second pressure level (e.g., about −200 mmHg vacuum pressure).

In certain embodiments, the pump 100 is in fluid communication with a process fluid source 238, which can comprise any fluid for which pumping is desired. For example, in some medical applications, the process fluid source 238 comprises blood circulating in the vasculature of a patient. Other fluids at a variety of pressures and/or at a variety of viscosity levels are also possible. The pump 100 can further be in fluid communication with the process fluid source 238 via the inlet line 180*i*. The pump 100 can further be in fluid communication with a process fluid destination, discharge, receiver, or return 239 via the outlet line 180*o*. In some embodiments, the process fluid source 238 and the process fluid return 239 are at about the same pressure. In other embodiments, the process fluid source 238 is at a lower pressure than the process fluid return 239. Other arrangements and configurations are also possible.

FIG. 16 illustrates that the motive fluid of pressure source 220 and the vacuum source 230, respectively, are in selective fluid communication with pump 100 via the manifold mounting assembly 400. In certain embodiments, the vacuum source 220 (which may be a vent) can be at a pressure that is less than the process fluid source 238 pressure to allow intake of the process fluid into the pumping chambers, and the pressure source 230 can be at a pressure level that is greater than that of the process fluid return 239. The pressure levels or suction levels can be selectively controlled by pressure regulators (not shown in FIG. 16) or other devices to the desired levels for pumping the process fluid. In various embodiments, the pressure level of motive fluid provided by the pressure source 220 can be between about 0 mmHg and about 1000 mmHg, between about 50 mmHg and about 500 mmHg, or between about 100 mmHg and about 200 mmHg. In various embodiments, the pressure level of motive fluid provided by the vacuum source 230 can be between about −500 mmHg and about 0 mmHg, between about −250 mmHg, or between about −100 mmHg and about −50 mmHg.

In some embodiments, the control valve 210 is alternated between operational states to cyclically apply pressure and vacuum to supply ports A and B prior to the chamber diaphragms 140a, b reaching the end-of-stroke or pump chamber surfaces 114a, 114b and/or the chamber cavity surfaces 165a, b. In certain of such embodiments, the pressure and flow of the process liquid at the process fluid receiver 230 can be maintained at a substantially constant level.

In certain embodiments, as the pump 100 causes fluid to flow from the process fluid source 238 to the process fluid return 239, the flow can be restricted by the capacities of fluid carrying components that may be located between the process fluid source 238 and the inlet line 180i and/or between the outlet line 180o and the process fluid receiver 239. In some embodiments, the pressure levels of the pressure source 220 and/or the vacuum source 230 and/or the operational speed or cycling rate of the valve 210 can be adjusted to achieve a desired flow rate of the process fluid.

In certain embodiments, the pressure levels of the sources 220, 230 and/or the cycling rate (or rates) of the valve 210 can be selectively changed to cause the double diaphragm pump 100 to operate in one or more different desired operating modes. For example, in a first illustrative mode, the valve 210 can switch the first supply port A from being in fluid communication with the pressure source 220 to being in fluid communication with the vacuum source 230 and can substantially simultaneously switch the second supply port B from being in fluid communication with the vacuum source 230 to being in fluid communication with the pressure source 220. The change in supply sources 220, 230 can cause the chamber diaphragms 140a, b to switch stroke direction prior to one of the pump chambers 103a, b being completely filled and prior to the other pump chamber 103a, b being completely emptied. With the pump chambers 103a, b operating opposite from each other (e.g., one chamber 103a draws process fluid from the fluid source 238 while the other chamber 103b expels process fluid to the fluid return 239), the pump 100 can draw process fluid and expel process fluid at a substantially constant rate.

In another mode, the pump 100 can be controlled to provide a substantially constant draw pattern or fill rate and a pulsatile discharge pattern by adjusting the cyclic speed of the control valve 210, the vacuum level of the vacuum source 230, and/or the pressure level of the pressure source 220. For example, in some embodiments, one of the chamber diaphragm regions 141a, b can switch stroke direction prior to completely filling one of the chambers 103a, b with process fluid when the valve 210 transitions from an open state to a closed state, and can completely discharge the contents of the chamber 103a, b and contact one of the chamber cavity surfaces 114a, b for a period of time before the valve 210 transitions from the closed state back to the open state. Likewise, the other chamber diaphragm region 141a, b can reach the end-of-stroke condition when it completely discharges the contents of the other chamber 103a, b and can be in contact with the other chamber cavity surface 114a, b for a period of time prior to the valve 210 transitioning from a closed state to an open state, and can fail to reach the fill end-of-stroke condition of the chamber 103a, b with process fluid prior to the valve 210 transitioning from the open state back to the closed state.

Similarly, in yet another mode, the pump can operate in a pulsatile fill pattern and substantially constant discharge pattern. In certain of such embodiments, one of the chamber diaphragm regions 141a, b can permit one of the chambers 103a, b to completely fill with process fluid and can contact one of the cavity surfaces 165a, b for a period of time before the valve 210 transitions from a substantially full state to a partially emptied state, and can fail to completely discharge the contents of the chamber 103a, b before the valve 210 transitions from the partially emptied state back to the substantially full state. Likewise, the other chamber diaphragm region 141a, b can fail to completely discharge the contents of the other chamber 103a, b before the valve 210 transitions from a partially emptied state to a substantially full state, and can permit the other chamber 103a, b to completely fill with process fluid and can contact the other cavity surface 165a, b for a period of time before the valve 210 transitions from the substantially full state back to the partially emptied state.

Other embodiments of supplying motive fluid to the double diaphragm pump 100 are also possible. For example, in some embodiments, multiple air control valves 210 may be employed. In further embodiments, a common motive fluid supply to one or more of the valves 101i, 101o, 102i, 102o and/or a common motive fluid supply provided to the pump chambers 103a, 103b can instead be replaced with a separate supply of motive fluid to each valve 101, 102 and chamber 103. For example, certain embodiments of the two air transfer passages 417, 418 could be replaced with six separate passages (one for each air transfer boss 411-416).

In some embodiments, the valves 101i, 101o, 102i, 102o and chambers 103a, b can be sequenced electronically to provide operating modes such as those described above. In further embodiments, operating a pump in a flow forward mode and then in a flow reverse mode by changing the sequencing of actuating the valves 101i, 101o, 102i, 102o and chambers 103a, b can also be achieved. In some embodiments, individual control of the pump valves 101i, 101o, 102i, 102o and pump chambers 103a, b can also allow other pump operating modes that can create constant (or substantially constant) and pulsatile flow from the process fluid source 238 to the process fluid receiver 239 (or vice versa). In some embodiments, time delays between allowing fluid communication between motive fluid sources (e.g., sources 220, 230) and one or more of the chambers 103a, b and valves 101i, 101o, 102i, 102o using individual controls can be advantageous. For example, in some embodiments, it can be desirable to actuate one or more of the valves 101i, 101o, 102i, 102o prior to actuating the chambers 103a, b FIG. 17 is a schematic illustration of an embodiment of a cardiopulmonary bypass system 700 that includes multiple double diaphragm blood pumps 100b-f. The system 700 can further include one or more reservoirs 706, blood oxygenators 701, fluid conduits, such as tubing segments 702, 705, catheters 704, 712, cannulae 703, 709, medical fluid sources 711, heat exchangers, and/or filtration units. Certain embodiments of the system 700 include components and sub-systems that are not shown in FIG. 17 for purposes of clarity. However, it will be understood that such components and sub-systems are conventional and readily available from numerous well-known sources. In some embodiments, the system 700 uses cannulae that are either inserted directly into the right atrium of the heart (as illustrated in FIG. 17), to the vena cava, or at another desired location of the patient P. Interconnections between devices or components of the system 700 can include, in some embodiments, segments of surgical tubing. For example, in some embodiments, conventional ⅜ or ¼ inch inner diameter surgical polyvinyl-chloride tubing is used.

In certain embodiments, one or more of the diaphragm blood pumps 100b-f may have separately selectable and controllable pressure levels. For example, in some embodiments, each blood pump 100b-f is connected to a separate pressure source 220 and/or a separate vacuum source 230. In further embodiments, one or more of the pumps 100b-f can include a valve 210 that cycles at a different rate. In some embodiments, one or more of the pumps 100b-f share a common pressure source 220 and/or vacuum source 230. In certain of such embodiments, pneumatic regulators can be placed in line from the main pressure source 220 and vacuum source 230 to create unique pressure and/or suction levels for each pump 100b-f.

In some embodiments, one or more of the diaphragm blood pumps 100b-f may have separate motive fluid control valves 210, and one or more controllers 212 associated with each control valve 210 may operate the pumps 100b-f at different rates, which may be dependent upon the function the pump serves within the cardiopulmonary by-pass system 700. In some embodiments, a single processor 452 controls the one or more valve controllers 212 and the cycle rates or cycle patterns of the one or more valves 210. In other embodiments, multiple processors may provide the pumps 100b-f with different pumping rates and/or modes.

In certain embodiments, the reservoir 706 is supplied with blood flow from the patient P from the venous return catheter 704 via the venous tubing segment 705 and from the interconnections with the diaphragm blood pumps 100c 100d, and may be interconnected with other components of the system 700. Blood can be pumped from the reservoir 706 using a double diaphragm blood pump 100b, through the blood oxygenator 701, and back to the patient P via arterial tubing segment 702 and arterial cannula 703.

In some embodiments, the double diaphragm pump 100b may be operated in a manner that provides pulsatile blood flow to the patient P through the arterial cannula 703. A time delay between the cyclically controlled discharge of the pump chambers 103a, b, such as described above, can cause the pump 100b to create a more physiological "heart-like" flow through the circuit. Many of the components in the system 700 can act to dampen the effect of pulsation created by the pump 100b before the blood is returned to the patient P. In some embodiments, the pump 100b can be controlled to offset these effects. For example, in some embodiments, a processor 452 includes programmed instructions and/or implements one or more algorithms to counteract pulsation dampening provided by the system 700. In some embodiments, the processor 452 can utilize information regarding the amount of dampening provided by the system to dynamically alter operation of the pump 100b and thereby provide a desired pulsatile pumping pattern. For example, in some embodiments, the system 700 includes one or more flow meters or pressure sensors (not shown) that provide information to the processor 452 regarding the pressure and/or the flow rate of blood within the tubing segment 702.

In certain embodiments, the pump 100b operates in a mode that creates a substantially constant flow into the venous return catheter 704 from the patient P and a pulsatile outlet flow out of the arterial cannula 703 and to the patient P. Dampening of the pump-created pulsations in the various reservoirs, tubing segments, and other devices in the circuit may occur. The dampening effects can be offset by controlling the vacuum source 220, pressure source 230, and pump cycle rate to cause the pump 100b to expel fluid at a faster rate than blood is drawn, which can create an end-of-stroke discharge condition during each pump stroke. In other embodiments, the pump 100b can exhibit substantially equivalent discharge and fill times, which can create a substantially constant flow into the venous return catheter 704 from the patient and a substantially constant flow out of the arterial cannula 703 and into the patient P. Pump-created process fluid pressure pulsations can be dampened by the various reservoirs, tubing segments, and other devices in the circuit causing a substantially uniform flow into and out of the extracorporeal circuit.

In certain embodiments, when the diaphragm blood pump 100b is used to effect blood flow both away from patient P, such as via the venous return catheter 704 and into the patient, such as via arterial cannula 703, flow rates through the pump can be in a range of, for example, between about 1.0 and about 7.0 liters per minute, between about 1.0 and about 5.0 liters per minute, between about 1.0 and about 3.0 liters per minute, no more than about 7.0 liters per minute, no more than about 6.0 liters per minute, no more than about 5.0 liters per minute, no more than about 4.0 liters per minute, no more than about 3.0 liters per minute, no less than about 1.0 liters per minute, no less than about 2.0 liters per minute, or no less than about 3.0 liters per minute, depending on the medical procedure involved.

With continued reference to FIG. 17, blood may be removed and recovered from a surgical field via one or more suction devices 713 that can be positioned or manipulated in the surgical field and interconnected to a diaphragm blood pump 100c. Examples of such a suction device that can be suitable for operation with the pump 100c are available, for example, from Medtronic DLP, Inc. of Grand Rapids, Mich.

Blood can also be recovered through the vent catheter 712, which may be placed inside a cavity of the heart or other cavity of a patient to withdraw blood and control the pressure or suction level inside the cavity. In such applications, it can be desirable to operate the pump 100d with near uniform suction by cyclically switching the filling and discharge of the pump chambers 103a, b before the diaphragms reach an end-of-stroke fill position. The recovered blood may be sequestered in a separate reservoir (not shown) and may be selectively returned to the reservoir 706. The recovered blood may also be processed through a system (not shown) configured to clean the blood before it is returned to the reservoir 706. In some embodiments, flow rates through the diaphragm blood pumps 100c, 100d used to effect blood flow from patient P via the suction device 713 and the vent catheter 712 to the reservoir 706 can be in the range of between about 0 and about 1.0 liters/minute, depending on the medical procedure being performed.

As shown in FIG. 17, in some embodiments, a medical fluid source 711 is coupled with a pump 100f. In some embodiments, the medical fluid source 711 comprises cardioplegia fluid, which can be mixed with blood and supplied to the patient P by operation of the diaphragm blood pumps 100e, f. In some embodiments, controlling the cardioplegia fluid mixture and delivery rate (e.g., before returning the mixture to the patient P) can be accomplished by controlling the discharge pressure of one or more of the pumps 100e, f. For example, in some embodiments the pressure level of one or more pressure sources 220 and/or vacuum sources 230 associated with one or more of the pumps 100e, f can be adjusted. In some embodiments, the process fluid discharged from one or more of the pumps 100e, f can be passed through one or more flow restrictors (not shown). In certain embodiments, the rate of flow can be nearly constant at a given pressure difference across the restrictors, even with small changes in fluid conditions, such as temperature and/or viscosity fluctuations.

In some embodiments, one or more flowmeters (not shown) can be included in the outlet fluid lines of one or more of the pumps 100e, *f* and can sense the flow rate of fluid discharged from the pumps 100e, *f*. The one or more flowmeters can provide feedback information regarding the flow rate to one or more processors 452 that control the pumps 100e, *f*. In some embodiments, the pressure level in the pressure source 220 and/or the vacuum source 230 can be adjusted in response to the feedback information to cause the flow rate from the pumps 100e, *f* to increase or decrease to obtain a desired level of mixing and a desired delivery rate of mixed fluid to the patient P. In some embodiments, the cycle rate at which diaphragm actuation regions of a given pump 100e, *f* are actuated can be adjusted to provide increased or decreased fluid flow from that pump 100e, *f*. In certain embodiments, appropriately mixed and/or heated or cooled cardioplegia fluid can be delivered via a tubing segment and cardioplegia cannula 709 to the patient P.

In certain embodiments, the pumps 100b-f can provide desirable pressure levels for the system 700. In some embodiments, the pumps 100b-f may be safer than pumps conventionally used in some of the applications described above, such as roller pumps. For example, if a vascular access connection to the patient P is somehow degraded or a blockage occurs in the system 700 (e.g., via a kink in a portion of tubing), certain embodiments of the pumps 100b-f have limited capability to generate high pressure and/or high suction levels that may damage the blood in the system 700 and/or that might otherwise be hazardous to the patient P. For example, in some embodiments, the pressure sources 220, 230 can be at pressure levels that limit the amount of pressure and/or suction provided to extracorporeal blood within the system 700. In various embodiments, the pressure of extracorporeal blood within the system is within a of between about −250 mmHg and about 500 mmHg, between about −200 mmHg and about 400 mmHg, or between about −100 mmHg and about 300 mmHg. In some embodiments the pressure of extracorporeal blood within the system 700 is no less than about −250 mmHg, no less than about −200 mmHg, no less than about −150 mmHg, no less than about −100 mmHg, no greater than about 500 mmHg, no greater than about 400 mmHg, no greater than about 300 mmHg, or no greater than about 200 mmHg.

Further, some embodiments of the pumps 100b-f do not significantly raise the temperature of blood within the system 700 if a vascular access connection to the patient P is somehow degraded or a blockage occurs in the system 700. In various embodiments, the pumps 100b-f change (e.g., raise) the temperature of extracorporeal blood within the system 700 by no more than about 3° C., no more than about 4° C., no more than about 5° C., or no more than about 6° C.

FIG. 18 is a schematic illustration showing an embodiment of a heart-assist system 750 that comprises a double diaphragm pump 100g. The pump 100g can be attached to an inlet line 180i and an outlet line 180o. In the illustrated embodiment, the inlet line 180i provides fluid communication between the vasculature of the patient P and the pump 100g. In some embodiments, the inlet line 180i is attached to a lower pressure blood vessel, such as a vein or ventricle, via a cannula or an anastomosis attachment 753. Similarly, the outlet line 180o can be attached to a higher pressure blood vessel, such as an artery or aorta, via a cannula or anastomosis attachment 754. In some embodiments, each of the inlet lines 180i and outlet lines 180o comprises a tubing segment. The tubing sections may be percutaneous and can allow the pump 100g to run externally to the patient P.

In some embodiments, the heart-assist system 750 comprises additional components and devices that are known in the art (not shown). For example, in various embodiments, the heart-assist system 750 comprises one or more reservoirs, air bubble traps, filters, and/or other devices.

In various embodiments, the system 750 can provide flow rates to or from the patient P in the range of about 1.0 liters/minute to about 8.0 liters/minute, depending on the amount of heart support needed. In certain embodiments, the pump 100g comprises pump chambers 103a, 103b that each have a volume of between about 15 cubic centimeters and about 50 cubic centimeters, between about 20 cubic centimeters and about 30 cubic centimeters, no more than about 25 cubic centimeters, or about 25 cubic centimeters. In some embodiments, the pump 100g is operated at a rate between about 10 and about 200 cycles per minute, between about 90 and about 130 cycles per minute, between about 100 and about 120 cycles per minute, no more than about 200 cycles per minute, no more than about 150 cycles per minute, no more than about 120 cycles per minute, no less than about 10 cycles per minute, no less than about 50 cycles per minute, no less than about 100 cycles per minute, or about 120 cycles per minute. In various embodiments, the pump 100g can deliver blood to the patient P at a rate between about 2 liters per minute and about 8 liters per minute, between about 3 liters per minute and about 7 liters per minute, or between about 4 liters per minute and about 6 liters per minute. In certain embodiments, the volume of the pump chambers 103a, 103b of a pump 100g and the number of cycles per minute at which the pump 100g operates can be adjusted to provide a desired flow rate. In further embodiments, relatively lower cycles per minute can lengthen the life expectancy of the pump 100g and/or can aid in providing pulsatile blood flow to a patient that mimics a heartbeat.

FIG. 19 schematically illustrates a hemodialysis system that includes an extracorporeal circuit 800. In certain embodiments, the circuit 800 includes a diaphragm pump 100h, a dialyzer 810, and a dialyzing liquid system 820. The circuit 800 can be in fluid communication with a patient P. Blood can be withdrawn from the patient P at a blood source 238 and can be returned to the patient P at a blood receiver 239. Blood can flow through the circuit 800 in the direction of the arrows. In the illustrated embodiment, blood flows from the patient P to a drip chamber 803 via tubing 802, from the drip chamber 803 to the pump 100h via tubing 805, and from the pump 100h to the dialyzer 810 via tubing 807. Blood flows from the dialyzer 810 to a drip chamber 812 via tubing 811, and from the drip chamber 811 to the patient P via tubing 814.

In some embodiments, uptake from the process fluid source 238 and discharge to the process fluid receiver 239 occurs via needles punctured into an artery to vein fistula or graft shunt, or alternatively, from a catheter positioned in a large central vein. In certain embodiments, for the portion of the circuit 800 between the patient P and the pump 100h, blood pressure can be measured and monitored by means of a pressure sensor, such as a piezo-resistive pressure transducer 804a that can be connected to the drip chamber 803, whereby a hydrophobic membrane filter (not shown) serves to prevent contamination of the blood. Similarly, venous reflux pressure in the portion of the circuit 800 between dialyzer 810 and the patient P can be measured by means of a pressure transducer 804b. Pressure sensors can be used at other portions of the circuit 800. For example, in some embodiments, pressure sensors can be used to monitor the pressure levels of blood entering and exiting the pump 100h.

Pressure sensors can also be used to determine the pressure levels of motive fluid provided to the pump 100h.

In certain embodiments, the blood pump 100h effects the flow of blood in the extracorporeal circuit 800. In some embodiments, a heparin pump 808 provides for continuous feed of a desired heparin dose to prevent blood coagulation. The dialyzing liquid system 820 causes dialyzing liquid to flow through the dialyzer 810 and acts as a receiver of excess fluid and toxins removed from the blood that flows through the dialyzer. In some embodiments, the components of the extracorporeal blood circuit 800 are connected with each other via suitable safety devices known in the art or yet to be devised.

In some embodiments, an air detector 825 is included between the dialyzer 810 and the patient P. The air detector 825 can be configured to prevent infusion of blood foam or air, which may have entered the extracorporeal circuit 800, into the patient P. In some embodiments, the air detector 825 recognizes whether air bubbles or microfoam are present in the drip chamber 812 or elsewhere in the circuit 800. The air detector 825 can be in communication with a processor 452 (see, e.g., FIG. 16), which may switch off the blood pump 100f in response to information received from the detector 825.

In other embodiments, the pump 100h may similarly be deactivated in response to other information regarding the circuit 800. For example, the sensors 804a, b may detect an undesirable increase or decrease of the arterial or venous pressure above or below a threshold level. The information can be used to deactivate the pump 100h Similarly, the pump 100h may be deactivated as a result of a blood leak. In some embodiments, the pump 100h may be operatively associated with a control system 451, which may include an interface 453. In some embodiments, the interface 453 can display or otherwise signal information received from sensors within the circuit 800.

In some embodiments, information regarding the pressure of blood in the circuit 800, such as information provided by one or more of the pressure transducers 804a, b, is used to adjust the pressure level of motive fluid delivered to the pump 100h. For example, in some embodiments, the pressure transducers 804a, b, are configured to communicate with a processor 452 (see, e.g., FIG. 12), such as by one or more electrical or wireless connections. The processor 452 can utilize the information thus received to selectively control the pressure levels of motive fluid delivered from motive fluid sources, such as the sources 220, 230, in a manner such as described above (e.g., via one or more pressure regulators) and/or to control cycle rates and stroke durations of the pump 100h. For example, in some embodiments, the pressure levels of the motive fluid from the pressure sources 220, 230 and the cycle rates at which fluid communication is alternately established between distinct sets of valves and pump chambers is adjusted such that substantially constant fluid flow is established from the patient P to the extracorporeal circuit 800 and/or from the extracorporeal circuit 800 to the patient P. In some embodiments, the pump 100h provides pulsatile flow to the dialyzer 810 and essentially constant flow from the patient P to the extracorporeal circuit 800.

In certain embodiments, the pump 100h can provide desirable pressure levels for the extra corporeal circuit 800. In some embodiments, the pump 100h may be safer than conventional dialysis pumps, such as roller pumps. For example, if the vascular access connection to the patient is somehow degraded or a blockage occurs in the extracorporeal circuit 800 (e.g., via a kink in a portion of tubing), certain embodiments of the pump 100h have limited capability to generate high pressure and/or high suction levels that may damage the blood in the circuit 800 and/or that might otherwise be hazardous to the patient P. Further, some embodiments of the pump 100h does not significantly raise the temperature of blood within the circuit under such conditions of connection degradation or blockage.

In some embodiments, the diaphragm blood pump 100f generates two overlapping substantially square wave inflow pressure profiles and outflow pressure profiles during the pumping cycle which can result in a substantially constant blood inflow pressure and/or a substantially constant blood outflow pressure. The inflow and outflow pressures can be set near or within safety limits to provide maximum process fluid flow without triggering pressure limit alarms. The pressure profile generated by conventional roller pumps used in hemodialysis procedures is somewhat sinusoidal and may only operate at the maximum pressure level for a short duration of the pumping cycle. Accordingly, in some embodiments, as compared with such conventional pumps, the pump 100h can achieve higher blood flows at the same peak pressure limits. Higher flow rates can reduce the duration of a given hemodialysis procedure. In some embodiments, the inflow rate and/or the outflow rate of the pump 100h can be controlled or balanced (e.g., via the processor 452) to be substantially continuous with little pulsation of pressures or flow, as compared to some roller pumps that cannot simultaneously control the inflow pressure, outflow pressure, and flowrate. In other embodiments, the pump 100h can be configured to operate in a manner similar to conventional roller pumps, if desired.

Non-limiting examples will now be discussed with reference to FIGS. 20, 21, 22A, and 22B. These examples provide illustrations of performance capabilities of some embodiments, and are not intended to limit the foregoing disclosure in any respect.

Example 1

Figure 20:
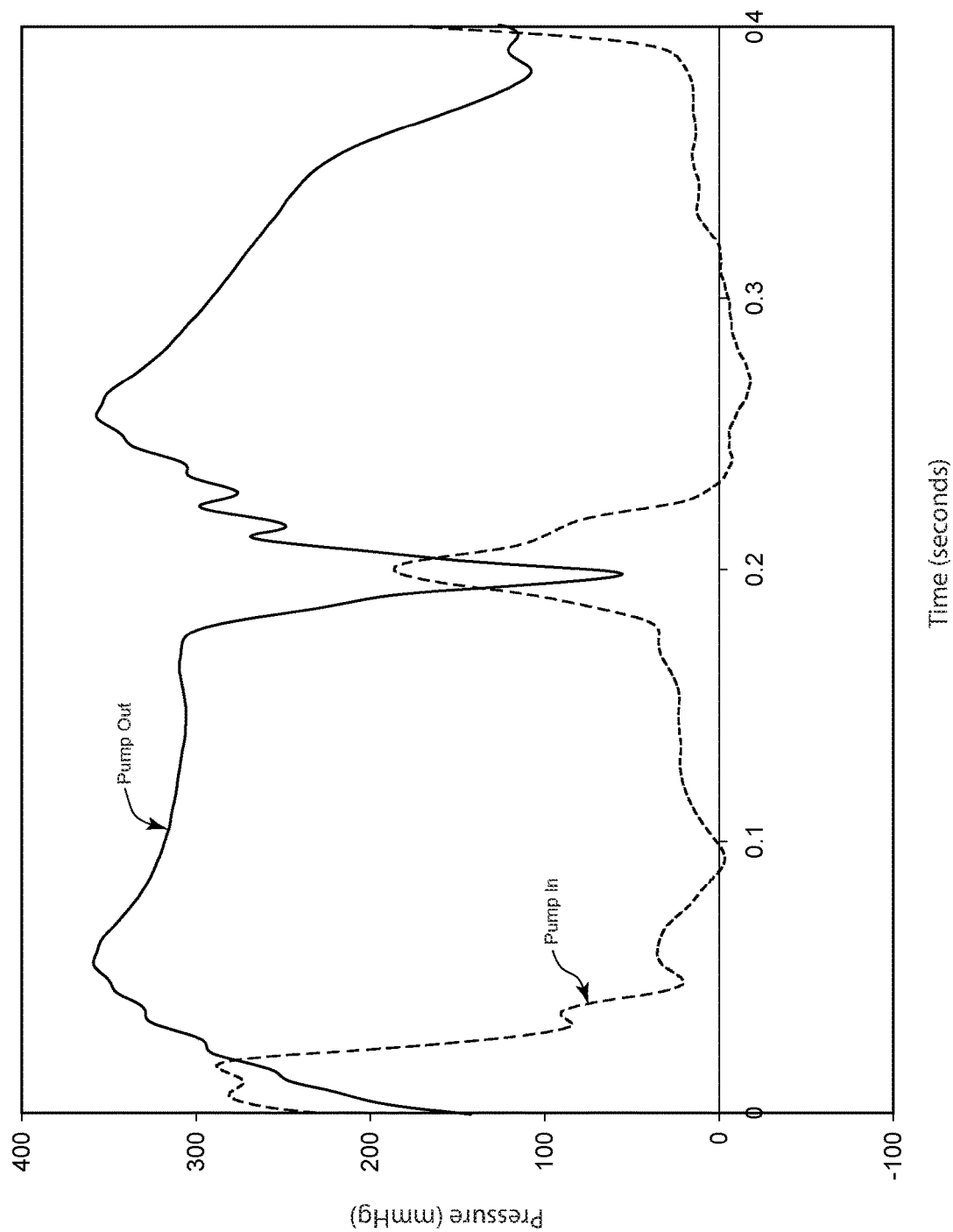
FIG. 20 is a chart showing an example of the pressure over time of blood entering and also of blood exiting an embodiment of a double diaphragm pump of the system depicted in FIG. 17 when configured for relatively constant flow operation.

FIG. 20 is a chart showing an example of pressure over time during a single pump cycle of an embodiment of a pump 100b used in a simulation of a cardiopulmonary bypass system such as the system 700 of FIG. 17. The chart depicts the pressure over time of blood entering the pump 100b (illustrated by the curve "Pump In") and also depicts the pressure over time of blood exiting the pump 100b (illustrated by the curve "Pump Out"). In the illustrated example, the pump 100b was operated in a mode for approximately uniform flow entering an extracorporeal circuit and approximately uniform flow exiting the circuit.

Various operational parameters of the pump 100b of the present example or of other embodiments of the pump 100b can be altered such that the inflow pressure for the extracorporeal circuit and the outflow pressure for the extracorporeal circuit are more uniform than that shown. For example, in some embodiments, the valley of the "Pump Out" line at the time coordinate of 0.2 seconds is relatively more shallow (e.g., has a minimum value of between about 200 and about 300 mmHg) and/or may be relatively more constricted (i.e., span over a shorter time period) Similarly, in some embodiments, the peak of the "Pump In" line at the time coordinate of 0.2 seconds is smaller (e.g., has a maximum valve of between about 0 and about 100 mmHg) and/or may be relatively more constricted.

In some embodiments, the inflow to the pump 100b and outflow from the pump 100b are approximately uniform. As used herein, the term "approximately uniform" when used to describe a flow rate is a broad term and signifies that over a single pump cycle, the maximum flow rate deviates from the average flow rate by no more than about 25% of the average flow rate during the pump cycle.

As discussed above, in some embodiments, flow and pressure pulsations created by a pump 100b can be dampened by the various reservoirs, tubing segments, and other devices in a circuit, and can result in more uniform flow rates and pressures. In certain embodiments, the uptake flow rate at a blood source 238 (e.g., a patient) and/or a delivery flow rate at a blood delivery destination 239 (e.g., a patient) can be essentially constant during a pump cycle. As used herein, the term "essentially constant" when used to describe a flow rate is a broad term and signifies that over a single pump cycle, the maximum flow rate deviates from an average flow rate by no more than about 10% of the average flow rate during the pump cycle. The pump 100b used to create the chart of FIG. 20 comprised two chambers, each having a displacement volume of about 25 milliliters. The chart illustrates the pump 100b as having operated at 200 millisecond per stroke (i.e., 400 millisecond per cycle or 150 cycles per minute). The pressure level in the pressure source 220 was established at 390 mmHg, the level of suction in the suction source was established at −125 mmHg, and the flow rate of blood effected by pump 100b was about 4 to 5 liters per minute. Connections lines 180i and 180o were comprised of plasticized PVC tubing with an inner diameter of 0.375 inches.

Example 2

Figure 21:
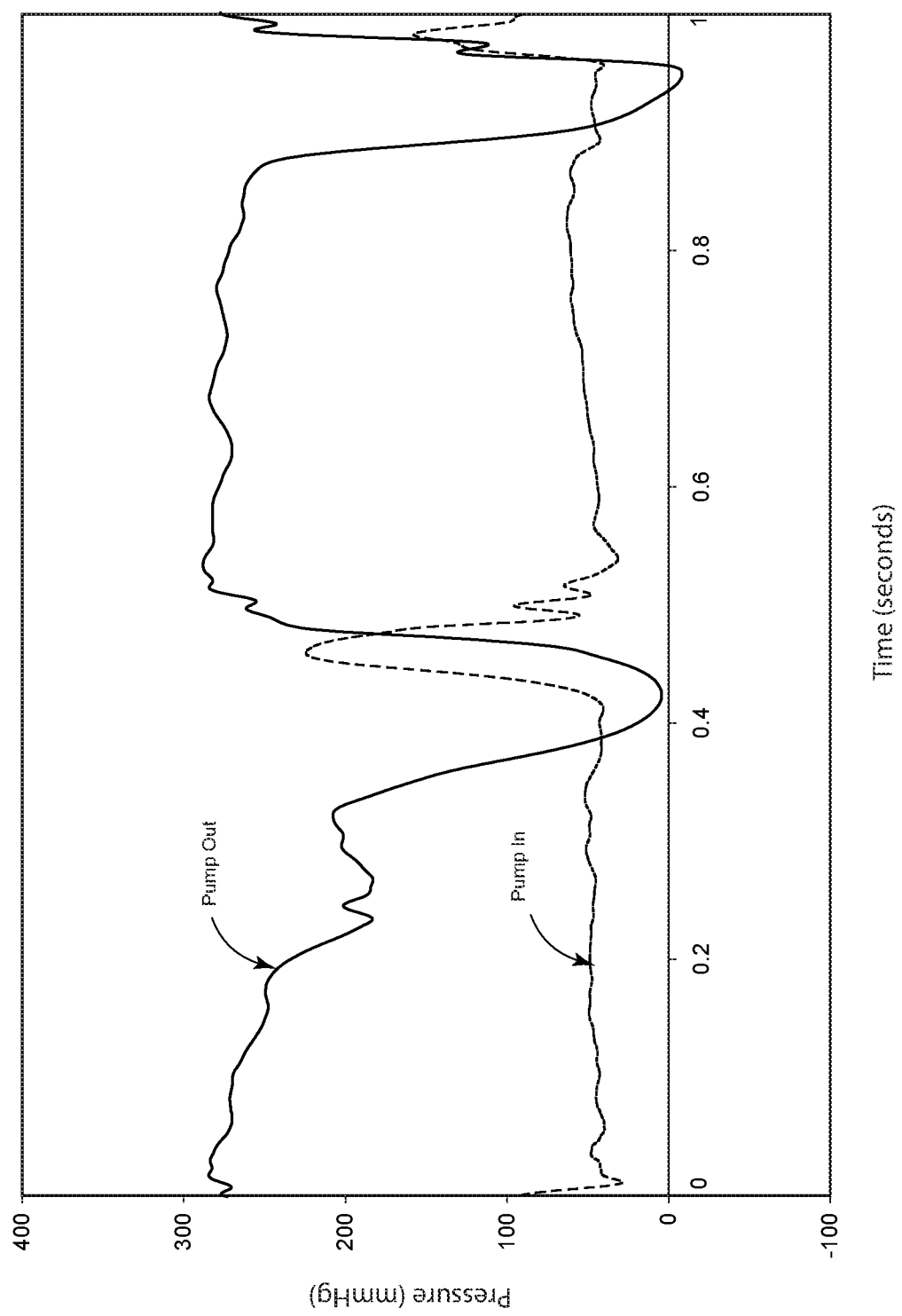
FIG. 21 is a chart showing an example of the pressure over time of blood entering and also of blood exiting an embodiment of a double diaphragm pump of the system depicted in FIG. 18 when the pump is configured for pulsatile outflow operation and relatively constant inflow operation.

FIG. 21 is a chart showing an example of pressure over time during a single pump cycle of an embodiment of a pump 100g used in a simulation of a heart assist system such as the system 750 of FIG. 18. The chart depicts the pressure over time during a single pump cycle of blood entering the pump 100g (illustrated by the curve "Pump In") and also depicts the pressure over time of blood exiting the pump 100g (illustrated by the curve "Pump Out"). The pump 100g was operated in a mode for relatively uniform flow entering an extracorporeal circuit and pulsatile outflow from the circuit.

Various operational parameters of the pump 100g of the present example or of other embodiments of the pump can be altered such that the inflow to the extracorporeal circuit is more uniform than that shown. For example, in some embodiments, the peak of the "Pump In" line at the time coordinate of about 0.45 seconds is smaller (e.g., has a maximum valve of between about 20 and about 80 mmHg) and/or may be relatively more constricted. Similarly, the pulsatile characteristics of the outflow from the extracorporeal circuit may be modified, as briefly discussed below.

The pump 100g used to create the chart of FIG. 21 comprised two chambers with each chamber having a displacement volume of about 25 milliliters. The chart illustrates the pump 100g as having operated at 500 millisecond per stroke (i.e., 1 second per cycle or 60 cycles per minute). The pressure level in the pressure source 220 was established at 300 mmHg and the level of suction in the suction source was established at 0 mmHg. The flowrate of blood effected by pump 100g was around 3 liters per minute. Shorter more pronounced pulse widths can be generated by extending the cycle time or increasing the pressure level in the pressure source 220. The pump was located about 30 inches below the fluid source 238 creating a positive pressure head of about 50 mmHg. Connections lines 180i and 180o were comprised of plasticized PVC tubing with an inner diameter of 0.375 inches. The outlet line 180o inner diameter was further reduced to 0.25 inches inner diameter for simulating a percutaneous access and arterial connection 754. The blood flowing through the connection lines caused pressure drops to and from the pump and the blood was delivered to the blood return 239 at less than 100 mmHg. The blood pump 100g of the illustrated example can create high pressures in the blood to overcome line losses, and as a result, a much smaller lumen can be used to access the vasculature of a patient P.

Example 3A

Figure 22A:
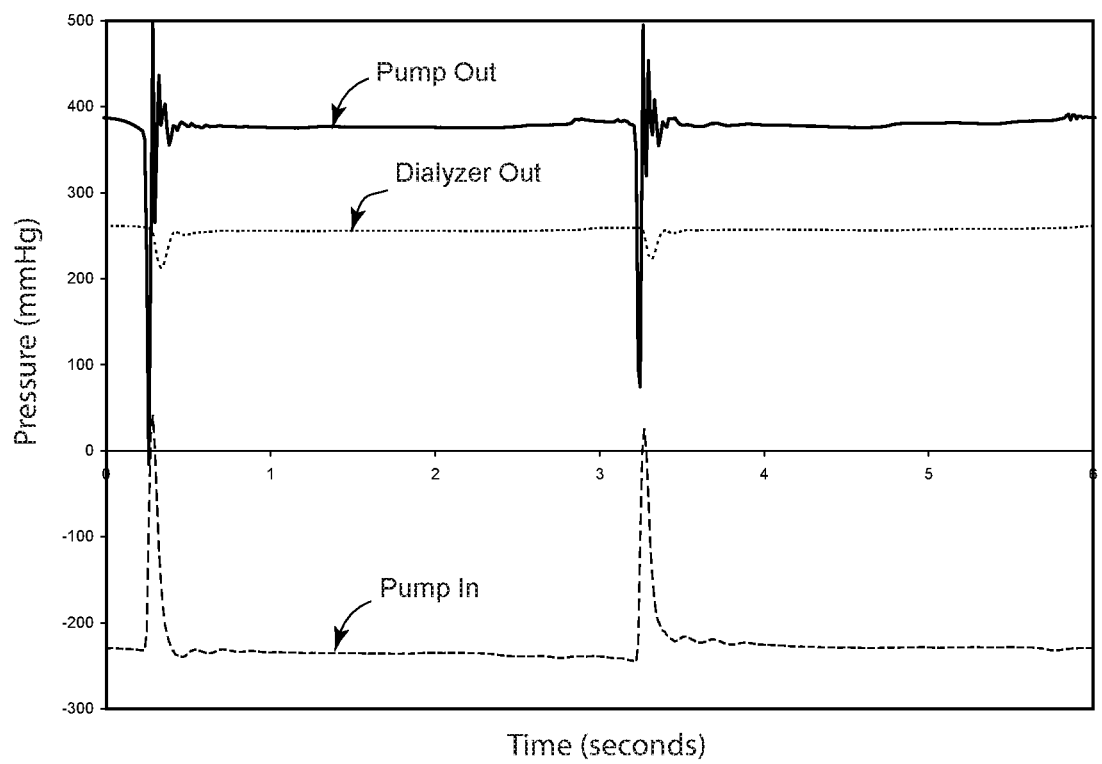
FIG. 22A is a chart showing an example of the pressure over time of blood entering and also of blood exiting an embodiment of a double diaphragm pump of the system depicted in FIG. 19, as well as the pressure over time of blood exiting the dialyzer, when the pump is configured for use in a hemodialysis procedure and controlled for relatively constant inflow operation and relatively constant outflow operation.

FIG. 22A is a chart showing an example of pressure over time during a single pump cycle of an embodiment of a pump 100h used in a simulation of a hemodialysis system such as the system 800 of FIG. 19. The chart depicts the pressure over time during a single pump cycle of blood entering the pump 100h (illustrated by the curve "Pump In"), the pressure over time of blood exiting the pump 100h (illustrated by the curve "Pump Out"), and also depicts the pressure over time of blood exiting the dialyzer 810 (illustrated by the curve "Dialyzer Out"). The pump 100h was operated in a mode for relatively uniform flow entering the circuit and relatively uniform flow exiting the extracorporeal circuit.

The chart illustrates the pump 100h as having operated at 3 seconds per stroke (i.e., 6 seconds per cycle or 10 cycles per minute). The pressure level in the pressure source 220 was established below about 390 mmHg, which caused the dialyzer out pressure to remain below about 250 mmHg, and the level of suction in the suction source was established above about 250 mmHg. The pump 100h used to create the chart of FIG. 22A comprised two chambers with each chamber having a displacement volume of about 25 milliliters. The flowrate of blood effected by pump 100h was about 250 to about 350 milliliters per minute. Connection lines 180i and 180o were comprised of plasticized PVC tubing with an inner diameter of 0.25 inches and connected to a commonly used disposable hemodialysis circuit with 16 gauge hemodialysis needles as the connections to fluid source 238 and fluid return 239. Most of the flow-driven pressure losses in the hemodialysis circuit 800 occurred through the needles and the dialyzer 810.

Example 3B

Figure 22B:
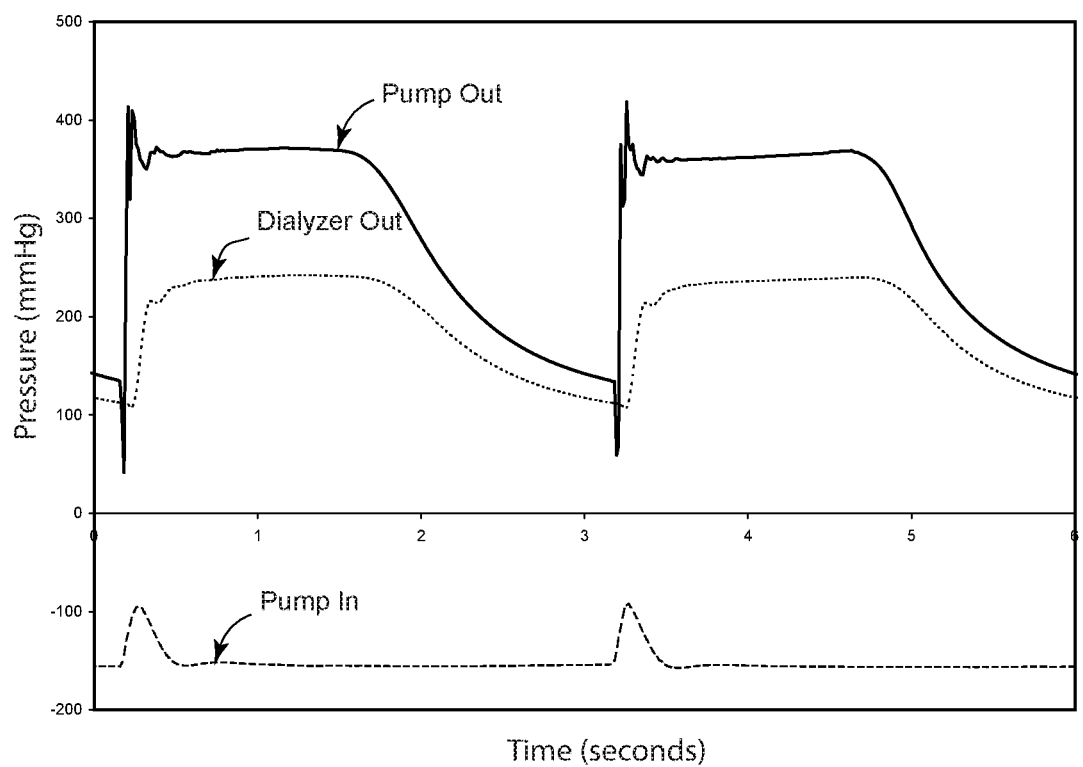
FIG. 22B is a chart showing an example of the pressure over time of blood entering and also of blood exiting the double diaphragm pump in the system depicted in FIG. 19, as well as the pressure over time of blood exiting the dialyzer, when the pump is configured for use in a hemodialysis procedure and controlled for relatively constant inflow operation and pulsatile outflow operation.

FIG. 22B is a chart showing an example of pressure over time during a single pump cycle of an embodiment of a pump 100h used in a simulation of a hemodialysis system such as the system 800 of FIG. 19. The chart depicts the pressure over time during a single pump cycle of blood entering the pump 100h (illustrated by the curve "Pump In"), the pressure over time of blood exiting the pump 100h (illustrated by the curve "Pump Out"), and also depicts the pressure over time of blood exiting the dialyzer 810 (illustrated by the curve "Dialyzer Out"). The pump 100h was operated in a mode for relatively uniform flow entering the circuit and pulsatile flow exiting the extracorporeal circuit.

The pump 100h is illustrated as having operated at 3 seconds per stroke (i.e., 6 seconds per cycle or 10 cycles per minute). Shorter, more pronounced pulse widths can be generated by extending the cycle time or increasing the pressure level in the pressure source 220. The pressure level in the pressure source 220 was established below about 360 mmHg, which caused the dialyzer out pressure to remain below about 250 mmHg, and the level of suction in the suction source was established above about −160 mmHg. The pump 100h used to create the chart of FIG. 22B comprised two chambers with each chamber having a displacement volume of about 25 milliliters. The flowrate of blood effected by pump 100g was about 200 to about 300 milliliters per minute. Connections lines 180i and 180o were comprised of plasticized PVC tubing with an inner diameter of 0.25 inches and connected to a commonly used disposable hemodialysis circuit with 16 gauge hemodialysis needles as the connections to fluid source 238 and fluid return 239. Most of the hemodialysis circuit blood flow pressure losses occurred through the needles and the dialyzer 810. A more pronounced pulsation can be achieved at a given flowrate with a combination of longer cycle times, larger bore needles, and lower flow resistance of the dialyzer.

Various features and structures discussed herein, and equivalents thereof, can provide specific functionalities. By way of illustration, in some embodiments, the first and second pump chambers 103a, b are examples of first and second means for selectively drawing process fluid from a process fluid source (e.g., the fluid source 238) and selectively expelling process fluid to a process fluid delivery destination (e.g., the process fluid delivery destination 239); the first and second inlet valves 101i, 102i are examples of first and second means for selectively permitting process fluid to flow to the first and second means for selectively drawing process fluid from a process fluid source and selectively expelling process fluid to a process fluid delivery destination, respectively; and the first and second outlet valves 101o, 102o are examples of first and second means for selectively permitting process fluid to flow from the first and second means for selectively drawing process fluid from a process fluid source and selectively expelling process fluid to a process fluid delivery destination, respectively.

As used in this specification, including the claims, the term "and/or" is a conjunction that is either inclusive or exclusive. Accordingly, the term "and/or" either signifies the presence of two or more things in a group or signifies that one selection may be made from a group of alternatives.

Without further elaboration, it is believed that one skilled in the art can use the preceding description to utilize the claimed inventions to their fullest extent. The examples and embodiments disclosed herein are to be construed as merely illustrative and not a limitation of the scope of the present disclosure in any way. It will be apparent to those having skill in the art that changes may be made to the details of the above-described embodiments without departing from the underlying principles discussed. In other words, various modifications and improvements of the embodiments specifically disclosed in the description above are within the scope of the appended claims. For example, any suitable combination of features of the various embodiments described is contemplated. Note that elements recited in means-plus-function format are intended to be construed in accordance with 35 U.S.C. § 112 ¶6. The scope of the invention is therefore defined by the following claims.

The invention claimed is:

1. A medical fluid delivery device comprising:
a process fluid body including a first side defining a first process fluid inlet valve seat and a first process fluid outlet valve seat and a second side defining a second process fluid inlet valve seat and a second process fluid outlet valve seat;
a first motive fluid plate coupled with the first side of the process fluid body, the first motive fluid plate defining a first motive fluid inlet valve actuation area and a first motive fluid outlet valve actuation area, wherein the first motive fluid inlet valve actuation area is aligned with the first process fluid inlet valve seat and the first motive fluid outlet valve actuation area is aligned with the first process fluid outlet valve seat;
a second motive fluid plate coupled with the second side of the process fluid body, the second motive fluid plate defining a second motive fluid inlet valve actuation area and a second motive fluid outlet valve actuation area, wherein the second motive fluid inlet valve actuation area is aligned with the second process fluid inlet valve seat and the second motive fluid outlet valve actuation area is aligned with the second process fluid outlet valve seat;
a first inlet valve diaphragm disposed between the first motive fluid inlet valve actuation area and the first process fluid inlet valve seat; and
a first outlet valve diaphragm, separate from the first inlet valve diaphragm, the first outlet valve diaphragm disposed between the first motive fluid outlet valve actuation area and the first process fluid outlet valve seat.

2. The medical fluid delivery device of claim 1, which includes a second inlet valve diaphragm disposed between the second motive fluid inlet valve actuation area and the second process fluid inlet valve seat and a second outlet valve diaphragm, separate from the second inlet valve diaphragm, the second outlet valve diaphragm disposed between the second motive fluid outlet valve actuation area and the second process fluid outlet valve seat.

3. The medical fluid delivery device of claim 1, which includes a process fluid pump chamber cavity in selective fluid communication with one of the process fluid inlet valve seats and one of the process fluid outlet valve seats.

4. The medical fluid delivery device of claim 3, which includes a motive fluid pump actuation area aligned with the process fluid pump chamber cavity.

5. The medical fluid delivery device of claim 4, which includes a pump diaphragm disposed between the motive fluid pump actuation area and the process fluid pump chamber cavity.

6. The medical fluid delivery device of claim 4, wherein the process fluid pump chamber cavity is defined by the process fluid body and the motive fluid pump actuation area is defined by one of the first or second motive fluid plates.

7. The medical fluid delivery device of claim 1, which includes (i) a first process fluid pump chamber cavity in selective fluid communication with the first process fluid inlet valve seat and the first process fluid outlet valve seat and (ii) a second process fluid pump chamber cavity in selective fluid communication with the second process fluid inlet valve seat and the second process fluid outlet valve seat.

8. The medical fluid delivery device of claim 7, which includes a first motive fluid pump actuation area aligned with the first process fluid pump chamber cavity and a second motive fluid pump actuation area aligned with the second process fluid pump chamber cavity.

9. The medical fluid delivery device of claim 8, which includes (i) a first pump diaphragm disposed between the first motive fluid pump actuation area and the first process fluid pump chamber cavity and (ii) a second pump diaphragm disposed between the second motive fluid pump actuation area and the second process fluid pump chamber cavity.

10. The medical fluid delivery device of claim 7, wherein the first and second process fluid pump chamber cavities are located on the first and second sides, respectively, of the process fluid body.

11. The medical fluid delivery device of claim 1, which includes at least one motive fluid source in motive fluid communication with the first and second motive fluid plates.

12. The medical fluid delivery device of claim 1, wherein the process fluid body includes at least one process fluid passageway in fluid communication with at least one of the first or second inlet or outlet process fluid valve seats.

13. The medical fluid delivery device of claim 12, wherein the at least one process fluid passageway is defined by the process fluid body.

14. The medical fluid delivery device of claim 1, wherein at least one of the motive fluid plates includes at least one motive fluid passageway in fluid communication with at least one of its respective first or second inlet or outlet motive fluid valve actuation area.

15. The medical fluid delivery device of claim 14, wherein the at least one motive fluid passageway is located within the at least one first or second motive fluid plate.

16. A medical fluid delivery device comprising:
a process fluid body including a first side defining a first process fluid inlet valve seat and a first process fluid outlet valve seat and a second side defining a second process fluid inlet valve seat and a second process fluid outlet valve seat;
a first motive fluid plate coupled with the first side of the process fluid body, the first motive fluid plate defining a first motive fluid inlet valve actuation area and a first motive fluid outlet valve actuation area, wherein the first motive fluid inlet valve actuation area is aligned with the first process fluid inlet valve seat and the first motive fluid outlet valve actuation area is aligned with the first process fluid outlet valve seat;
a second motive fluid plate coupled with the second side of the process fluid body, the second motive fluid plate defining a second motive fluid inlet valve actuation area and a second motive fluid outlet valve actuation area, wherein the second motive fluid inlet valve actuation area is aligned with the second process fluid inlet valve seat and the second motive fluid outlet valve actuation area is aligned with the second process fluid outlet valve seat;
a process fluid pump chamber cavity in selective fluid communication with one of the process fluid inlet valve seats and one of the process fluid outlet valve seats; and
a motive fluid pump actuation area aligned with the process fluid pump chamber cavity and in selective fluid communication with one of the motive fluid inlet valve actuation areas and one of the motive fluid outlet valve actuation areas.

17. The medical fluid delivery device of claim 16, wherein the process fluid pump chamber cavity is defined by the process fluid body and the motive fluid pump actuation area is defined by one of the first or second motive fluid plates.

18. The medical fluid delivery device of claim 16, wherein the process fluid pump chamber is a first process fluid pump chamber, the motive fluid pump actuation area is a first motive fluid pump actuation area, and which includes a second process fluid pump chamber cavity in selective fluid communication with the other one of the process fluid inlet valve seats and the other one of the process fluid outlet valve seats, and a second a motive fluid pump actuation area aligned with the second process fluid pump chamber cavity and in selective fluid communication with the other one of the motive fluid inlet valve actuation areas and the other one of the motive fluid outlet valve actuation areas.

19. The medical fluid delivery device of claim 16, wherein one of the first or second process fluid pump chambers is located on the first side of the process fluid body and the other of the first or second process fluid pump chambers is located on the second side of the process fluid body.

20. The medical fluid delivery device of claim 19, wherein the second process fluid pump chamber is located on the first side of the process fluid body and the first process fluid pump chamber is located on the second side of the process fluid body.

21. A medical fluid delivery device comprising:
a process fluid body including a first side defining a first process fluid valve seat and a second process fluid valve seat and a second side defining a third process fluid valve seat and a fourth process fluid valve seat;
a first motive fluid plate coupled with the first side of the process fluid body, the first motive fluid plate defining a first motive fluid valve actuation area and a second motive fluid valve actuation area, wherein the first motive fluid valve actuation area is aligned with the first process fluid valve seat and the second motive fluid valve actuation area is aligned with the second process fluid valve seat;
a second motive fluid plate coupled with the second side of the process fluid body, the second motive fluid plate defining a third motive fluid valve actuation area and a fourth motive fluid valve actuation area, wherein the third motive fluid valve actuation area is aligned with the third process fluid valve seat and the fourth motive fluid valve actuation area is aligned with the fourth process fluid outlet valve seat;
a first valve diaphragm disposed between the first motive fluid valve actuation area and the first process fluid valve seat;
a second valve diaphragm, separate from the first valve diaphragm, the second valve diaphragm disposed between the second motive fluid valve actuation area and the second process fluid valve seat;
a third valve diaphragm disposed between the third motive fluid valve actuation area and the third process fluid valve seat; and
a fourth valve diaphragm, separate from the third valve diaphragm, the fourth valve diaphragm disposed between the fourth motive fluid valve actuation area and the fourth process fluid valve seat.

22. The medical fluid delivery device of claim 21, wherein at least one of (i) the first process fluid valve seat, the first motive fluid valve actuation area, and the first valve diaphragm, (ii) the second process fluid valve seat, the second motive fluid valve actuation area, and the second valve diaphragm, (iii) the third process fluid valve seat, the third motive fluid valve actuation area, and the third valve diaphragm, or (iv) the fourth process fluid valve seat, the fourth motive fluid valve actuation area, and fourth valve diaphragm, form a pump inlet valve chamber or a pump outlet valve chamber.

23. The medical fluid delivery device of claim 21, wherein at least one of (i) the first process fluid valve seat, (ii) the second process fluid valve seat, (iii) the third process fluid valve seat, or (iv) the fourth process fluid valve seat, is in fluid communication with a process fluid pump chamber cavity.

24. The medical fluid delivery device of claim 23, wherein the process fluid pump chamber cavity is provided by the process fluid body.

25. The medical fluid delivery device of claim 21, wherein at least one of (i) the first motive fluid valve actuation area, (ii) the second motive fluid valve actuation area, (iii) the third motive fluid valve actuation area, or (iv) the fourth motive fluid valve actuation area, is in fluid communication with a motive fluid pump actuation area.

26. The medical fluid delivery device of claim 25, wherein the motive fluid pump actuation area is provided by one of the first or second motive fluid plates.

* * * * *